(12) United States Patent
Imai et al.

(10) Patent No.: US 7,737,158 B2
(45) Date of Patent: Jun. 15, 2010

(54) PROCESSES FOR REGULATING BLOOD GLUCOSE IN A MAMMAL

(75) Inventors: Shin-ichiro Imai, St. Louis, MO (US); Javier R. Revollo, St. Louis, MO (US)

(73) Assignee: Washington University, St. Louis, MO (US)

( * ) Notice: Subject to any disclaimer, the term of this patent is extended or adjusted under 35 U.S.C. 154(b) by 488 days.

(21) Appl. No.: 11/542,790

(22) Filed: Oct. 3, 2006

(65) Prior Publication Data

US 2007/0082373 A1 Apr. 12, 2007

Related U.S. Application Data

(60) Provisional application No. 60/725,572, filed on Oct. 11, 2005.

(51) Int. Cl.
*A61K 31/44* (2006.01)
(52) U.S. Cl. .................................................. 514/279
(58) Field of Classification Search ........................ None
See application file for complete search history.

(56) References Cited

FOREIGN PATENT DOCUMENTS

| JP | 2005-213206 | | 8/2005 |
|----|-------------|----|--------|
| WO | 2005/072767 | A1 | 8/2005 |
| WO | 2006/041624 | A2 | 4/2006 |

OTHER PUBLICATIONS

Revollo et al, Nampt/PBEF/Visfatin regulates insulin secretion in beta cells as a systemic NAD biosynthetic enzyme. Cell Metab. Nov. 2007;6(5):363-75.*
Araki, T., et al., "Increased Nuclear NAD Biosynthesis and SIRT1 Activation Prevent Axonal Degeneration," Science, Aug. 13, 2004, pp. 1010-1013, vol. 305, American Association for the Advancement of Science.
Arner, P., "Editorial: Visfatin—A True or False Trail to Type 2 Diabetes Mellitus," The Journal of Clinical Endocrinology & Metabolism, Jan. 2006, pp. 28-30, vol. 91, No. 1.
Bailey, S. D., et al., "Common Polymorphisms in the Promoter of the Visfatin Gene (PBEF1) Influence Plasma Insulin Levels in a French-Canadian Population," Diabetes, Oct. 2006, pp. 2896-2902, vol. 55.
Berndt, J., et al., "Plasma Visfatin Concentrations and Fat Depot-Specific mRNA Expression in Humans," Diabetes, Oct. 2005, pp. 2911-2916, vol. 54.
Bordone, L., et al., "Sirt1 Regulates Insulin Secretion by Repressing UCP2 in Pancreatic β Cells," PLoS Biology, Feb. 2006, pp. 0210-0220, vol. 4, No. 2.
Chen, M-P., et al., "Elevated Plasma Level of Visfatin/Pre-B Cell Colony-Enhancing Factor in Patients with Type 2 Diabetes Mellitus," The Journal of Clinical Endocrinology & Metabolism, Jan. 2006, pp. 295-299, vol. 91, No. 1.
Denu, J. M. "Linking Chromatin Function with Metabolic Networks: Sir2 Family of NAD+ -Dependent Deacetylases," TRENDS in Biochemical Sciences, Jan. 2003, pp. 41-48, vol. 28, No. 1.
Haider, D. G., et al., "The Release of the Adipocytokine Visfatin is Regulated by Glucose and Insulin," Diabetologia, May 31, 2006, pp. 1909-1914, vol. 49.
Hasmann, M., et al., "FK866, A Highly Specific Noncompetitive Inhibitor of Nicotinamide Phosphoribosyltransferase, Represents a Novel Mechanism for Induction of Tumor Cell Apoptosis," Cancer Research, Nov. 1, 2003, pp. 7436-7442, vol. 63.
Imai, S-I., et al., "Transcriptional Silencing and Longevity Protein Sir2 is an NAD-Dependent Histone Deacetylase," Nature, Feb. 17, 2000, pp. 795-800, vol. 403.
Khan, J. A., et al., "Molecular Basis for the Inhibition of Human NMPRTase, A Novel Target for Anticancer Agents," Nature Structural & Molecular Biology, Jul. 2006, pp. 582-588, vol. 13, No. 7.
Kim, M-K., et al., "Crystal Structure of Visfatin/Pre-B Cell Colony-Enhancing Factor 1/Nicotinamide Phosphoribosyltransferase, Free and in Complex with the Anti-Cancer Agent FK-866," J. Mol. Biol., 2006, pp. 66-77, vol. 362.
Kitani, T., et al., "Growth Phase-Dependent Changes in the Subcellular Localization of Pre-B-Cell Colony-Enhancing Factor," FEBS Letters, May 13, 2003, pp. 74-78, vol. 544.
Martin, P. R., et al., "Identification of a Plasmid-Encoded Gene from *Haemophilus ducreyi* Which Confers NAD Independence," Journal of Bacteriology, Feb. 2001, pp. 1168-1174, vol. 183, No. 4.
Moynihan, K. A., et al., "Increased Dosage of Mammalian Sir2 in Pancreatic β Cells Enhances Glucose-Stimulated Insulin Secretion in Mice," Cell Metabolism, Aug. 2005, pp. 105-117, vol. 2.
Pagano, C., et al., "Reduced Plasma Visfatin/Pre-B Cell Colony-Enhancing Factor in Obesity is not Related to Insulin Resistance in Humans," The Journal of Clinical Endocrinology & Metabolism, Aug. 2006, pp. 3165-3170, vol. 91, No. 8.
Picard, F., et al., "Sirt1 Promotes Fat Mobilization in White Adipocytes by Repressing PPAR-γ," Nature, Jun. 17, 2004, pp. 771-776, 921, vol. 429.
Revollo, J. R., et al., "The NAD Biosynthesis Pathway Mediated by Nicotinamide Phosphoribosyltransferase Regulates Sir2 Activity in Mammalian Cells," The Journal of Biological Chemistry, Dec. 3, 2004, pp. 50754-50763, vol. 279, No. 49.
Rodgers, J. T., et al., "Nutrient Control of Glucose Homeostatis Through a Complex of PGC-1α and SIRT1," Nature, Mar. 3, 2005, pp. 113-118, vol. 434.
Rongvaux, A., et al., "Pre-B-Cell Colony-Enhancing Factor, Whose Expression is Up-Regulated in Activated Lymphocytes, is a Nicotinamide Phosphoribosyltransferase, A Cytosolic Enzyme Involved in NAD Biosynthesis," Eur. J. Immunol., 2002, pp. 3225-3234, vol. 32.
Rongvaux, A., et al., "Reconstructing Eukaryotic NAD Metabolism," BioEssays, 2003, pp. 683-690, vol. 25, No. 7.
Samal, B., et al., "Cloning and Characterization of the cDNA Encoding a Novel Human Pre-B-Cell Colony-Enhancing Factor," Molecular and Cellular Biology, Feb. 1994, pp. 1431-1437, vol. 14, No. 2.
Sethi, J. K., et al., "Visfatin: The Missing Link Between Intra-Abdominal Obesity and Diabetes?," TRENDS in Molecular Medicine, Aug. 2005, pp. 344-347, vol. 11, No. 8.
Stephens, J. M., et al., "An Update on Visfatin/Pre-B Cell Colony-Enhancing Factor, An Ubiquitously Expressed, Illusive Cytokine That is Regulated in Obesity," Current Opinion in Lipidology, 2006, pp. 128-131, vol. 17.
van der Veer, E., et al., "Pre-B-Cell Colony-Enhancing Factor Regulates NAD+-Dependent Protein Deacetylase Activity and Promotes Vascular Smooth Muscle Cell Maturation," Circulation Research, Jun. 9, 2005, pp. 25-34, vol. 97.
Wang, T., et al., "Structure of Nampt/PBEF/Visfatin, A Mammalian NAD+ Biosynthetic Enzyme," Nature Structural & Molecular Biology, Jul. 2006, pp. 661-662, vol. 13, No. 7.

* cited by examiner

*Primary Examiner*—Sheridan Swope
(74) *Attorney, Agent, or Firm*—Senniger Powers LLP

(57) ABSTRACT

The present invention relates to processes for regulating the blood glucose concentration of a mammal.

5 Claims, 41 Drawing Sheets

NIH3T3

FIG. 15A
FIG. 15B
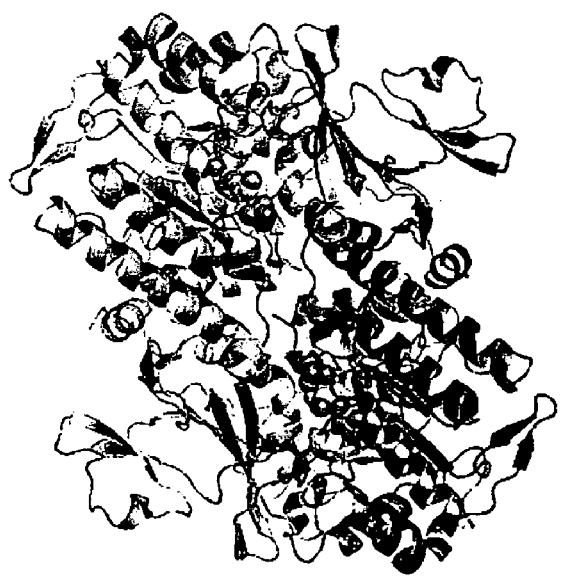
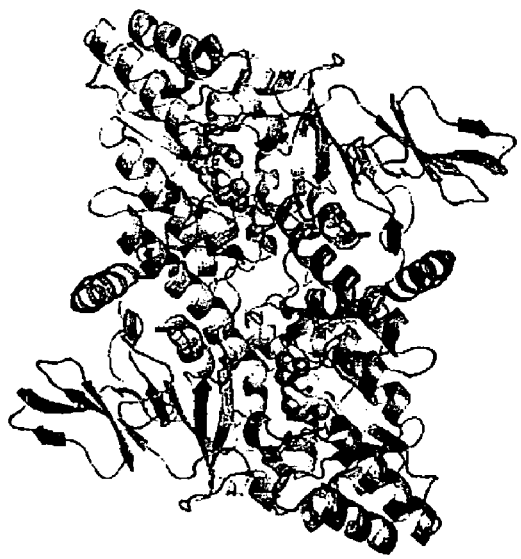
Nampt + NMN
Npt + NaMN

CELL EXTRACT

CULTURE SUPERNATANT

PROCESSES FOR REGULATING BLOOD GLUCOSE IN A MAMMAL

CROSS REFERENCE TO RELATED APPLICATIONS

This application claims the benefit of U.S. Provisional Patent Application Ser. No. 60/725,572, filed Oct. 11, 2005, the entire content of which is hereby incorporated herein by reference.

FIELD OF THE INVENTION

The present invention generally relates to processes for regulating the blood glucose concentration of a mammal. The present invention also generally relates to a polypeptide useful in nicotinamide adenine dinucleotide (NAD) biosynthesis.

BACKGROUND OF THE INVENTION

Nicotinamide adenine dinucleotide (NAD) and its derivative compounds are known as essential coenzymes in cellular redox reactions in all living organisms. Several lines of evidence have also shown that NAD participates in a number of important signaling pathways in mammalian cells, including poly(ADP-ribosyl)ation in DNA repair (Menissier de Murcia et al., EMBO J., (2003) 22, 2255-2263), mono-ADP-ribosylation in the immune response and G protein-coupled signaling (Corda and Di Girolamo, EMBO J., (2003) 22, 1953-8), and the synthesis of cyclic ADP-ribose and nicotinate adenine dinucleotide phosphate (NAADP) in intracellular calcium signaling (Lee, Annu. Rev. Pharmacol. Toxicol., (2001) 41, 317-345). Recently, it has also been shown that NAD and its derivatives play an important role in transcriptional regulation (Lin and Guarente, Curr. Opin. Cell. Biol., (2003) 15, 241-246). In particular, the discovery of Sir2 NAD-dependent deacetylase activity (e.g., Imai et al., Nature, (2000) 403, 795-800; Landry et al., Biochem. Biophys. Res. Commun., (2000) 278, 685-690; Smith et al., Proc. Natl. Acad. Sci. USA, (2000) 97, 6658-6663) drew attention to this new role of NAD.

The Sir2 family of proteins consumes NAD for its deacetylase activity and regulates transcription by deacetylating histones and a number of other transcription regulators (see FIG. 1). Because of this absolute requirement for NAD, it has been proposed that Sir2 proteins function as energy sensors that convert the energy status of cells to the transcriptional regulatory status of genes (Imai et al., Nature, (2000) 403, 795-800; Imai et al., Cold Spring Harbor Symp. Quant. Biol., (2000) 65, 297-302). Sir2 proteins produce nicotinamide and O-acetyl-ADP-ribose in addition to the deacetylated protein substrates in their deacetylation reaction (Moazed, Curr. Opin. Cell. Biol., (2001)13, 232-238; Denu, Trends Biochem. Sci., (2003) 28, 41-48; see also FIG. 1), and nicotinamide is eventually recycled into NAD biosynthesis. Unlike other NAD-dependent biochemical reactions, the NAD-dependent deacetylase activity of the Sir2 family of proteins is generally highly conserved from bacteria to mammals (Frye, Biochem. Biophys. Res. Commun., (2000) 273, 793-798), suggesting that the connection between NAD and Sir2 proteins is ancient and fundamental. In mammals, the Sir2 ortholog, Sirt1/Sir2α, has been shown to regulate metabolism in response to nutrient availability (Bordone and Guarente, Nat. Rev. Mol. Cell Biol., (2005) 6, 298-305). In adipocytes, Sirt1 triggers lipolysis and promotes free fatty acid mobilization by repressing PPAR-γ, a nuclear receptor that promotes adipogenesis (Picard et al., Nature, (2004) 429, 771-776). In hepatocytes, Sirt1 regulates the gluconeogenic and glycolytic pathways in response to fasting by interacting with and deacetylating PGC-1α, a key transcriptional regulator of glucose production in the liver (Rodgers et al., Nature, (2005) 434, 113-118). Additionally, Sirt1 promotes insulin secretion in pancreatic β cells in response to high glucose partly by repressing Ucp2 expression and increasing cellular ATP levels (Moynihan et al., Cell Metab., (2005) 2, 105-117). While little is known about the regulation of NAD biosynthesis in mammals, NAD biosynthesis may play a role in the regulation of metabolic responses by altering the activity of certain NAD-dependent enzymes such as Sirt1 in a variety of organs and/or tissues.

The NAD biosynthesis pathways have been characterized in prokaryotes by using *Escherichia coli* and *Salmonella typhimurium* (Penfound and Foster, Biosynthesis and recycling of NAD, in *Escherichia coli* and *Salmonella:* Cellular and Molecular Biology, p. 721-730, ed. Neidhardt, F. C., 1996, ASM Press: Washington, D.C.) and recently in yeast (Lin and Guarente, Curr. Opin. Cell. Biol., (2003) 15, 241-246; Denu, Trends Biochem. Sci., (2003) 28, 41-48). In prokaryotes and lower eukaryotes, NAD is synthesized by the de novo pathway via quinolinic acid and by the salvage pathway via nicotinic acid (see FIG. 2) (Penfound and Foster, id.) In yeast, the de novo pathway begins with tryptophan, which is converted to nicotinic acid mononucleotide (NaMN) through six enzymatic steps and one non-enzymatic reaction (Lin and Guarente, Curr. Opin. Cell. Biol., (2003) 15, 241-246). Two genes, BNA1 and QPT1, have been characterized in this pathway in yeast. At the step of NaMN synthesis, the de novo pathway converges with the salvage pathway (see FIG. 2). The salvage pathway begins with the breakdown of NAD into nicotinamide and O-acetyl-ADP-ribose, which is mainly catalyzed by the Sir2 proteins in yeast. Nicotinamide is then deamidated to nicotinic acid by a nicotinamidase encoded by the PNC1 gene. Nicotinic acid phosphoribosyltransferase (Npt), encoded by the NPT1 gene, converts nicotinic acid to NaMN, which is eventually converted to NAD through the sequential reactions of nicotinamide/nicotinic acid mononucleotide adenylyltransferase (encoded by NMA1 and/or NMA2) and NAD synthetase (encoded by QNS1).

It has been shown that the NAD salvage pathway plays an important role in regulating Sir2 activity in yeast (Lin et al., Nature, (2002) 418, 344-348; Anderson et al., J. Biol. Chem., (2002) 277, 18881-18890; Anderson et al., Nature, (2003) 423, 181-185). For example, increased dosage of NPT1 increases Sir2-dependent transcriptional silencing and extends the life span of yeast mother cells (Anderson et al., J. Biol. Chem., (2002) 277, 18881-18890). Consistent with this finding, deletion of NPT1 causes a loss of Sir2-dependent silencing (Sandmeier et al., Genetics, (2002) 160, 877-889). Additional copies of other salvage pathway genes, PNC1, NMA1, and NMA2, have also been shown to increase telomeric and rDNA silencing (Anderson et al., J. Biol. Chem., (2002) 277, 18881-18890), while deletions of the de novo pathway genes, BNA1 or QPT1, have also been shown to have no effect on silencing at these loci (Sandmeier et al., Genetics, (2002) 160, 877-889). It has also been shown that PNC1 may be induced by different types of stress, including caloric restriction, and plays a critical role in regulating Sir2 activity in yeast (Anderson et al., Nature, (2003) 423, 181-185). These findings suggest that the regulation of NAD biosynthesis may play a role in Sir2-mediated transcriptional silencing and longevity control in yeast.

In vertebrates, NAD biosynthesis is markedly different from that of yeast and invertebrates (see FIG. 3). It is known that mammals predominantly use nicotinamide rather than nicotinic acid as a precursor for NAD biosynthesis (Magni et al., Adv. Enzymol. Relat. Areas Mol. Biol., (1999) 73, 135-182). Despite significant numbers of studies about NAD biosynthesis in the 1950's and 1960's, mammalian NAD biosynthesis enzymes have been generally poorly characterized. For example, it was not until 2001 that human nicotinamide/ nicotinic acid mononucleotide adenylyltransferase (Nmnat), an enzyme required to convert NMN and NaMN to NAD in the nucleus (Hogeboom et al., J. Biol. Chem., (1952) 197, 611-620), was finally isolated and fully characterized (Emanuelli et al., J. Biol. Chem., (2001) 276, 406-412; Schweigler et al., FEBS Lett., (2001) 492, 95-100). Other critical enzymes in mammalian NAD biosynthesis pathways have yet to be characterized, thus the regulation of NAD biosynthesis is still relatively poorly understood in mammals.

Nampt has very ancient origins as an NAD biosynthesis enzyme. The entire pyridine nucleotide salvage cycle containing Nampt, Nmnat, and Sir2 homologues has been shown to exist even in the vibriophage (Miller et al., J. Bacteriol., (2003) 185, 5220-5233). Despite its ancient origins, Nampt has a relatively peculiar phylogenetic distribution. No other organisms between bacteria and vertebrates have obvious homologs of Nampt, except for one sponge species, and the homology of Nampt proteins between bacteria and vertebrates is unusually high (Revollo et al., J. Biol. Chem., (2004) 279, 50754-50763). Interestingly, the organisms that do not have Nampt homologs, such as yeast, worms, and flies, typically have nicotinamidase (Pnc1) homologs (Ghislain et al., Yeast, (2002) 19, 215-324.). It is likely that the organisms that have nicotinamidase use nicotinic acid as a precursor for NAD biosynthesis, while the organisms that have Nampt use nicotinamide as the main precursor for NAD biosynthesis. Because no obvious homologues of Pnc1 have been found in vertebrates (Rongvaux et al., Bioessays, (2003) 25, 683-690), the presence of Nampt, which allows a more direct pathway for NAD biosynthesis from nicotinamide (see FIG. 2), distinguishes the NAD biosynthesis in vertebrates from that in yeast and invertebrates.

The gene encoding human Nampt was originally isolated as a presumptive cytokine named pre-B cell colony-enhancing factor (PBEF) (Samal et al., Mol. Cell. Biol., (1994) 14, 1431-1437), although the PBEF function has never been reproduced. Since then, other groups have also shown that PBEF is indeed mammalian Nampt (Revollo et al., J. Biol. Chem., (2004) 279, 50754-50763; Rongvaux et al., Eur. J. Immunol., (2002) 32, 3225-3234; van der Veer et al., Circ. Res., (2005) 97, 25-34). Recently, Nampt/PBEF has been re-identified as a "new visceral fat-derived hormone" named visfatin (Fukuhara et al., Science, (2005) 307, 426-430). Fukuhara et al. report that visfatin is enriched in the visceral fat of both humans and mice and that its plasma levels increase during the development of obesity. Fukuhara et al. report that visfatin exerts insulin-mimetic effects in cultured cells and lowers plasma glucose levels in mice by binding to and activating the insulin receptor. However, the physiological relevance of visfatin is still in question because its plasma concentration is 40 to 100-fold lower than that of insulin. Additionally, Fukuhara et al. did not describe any connections between visfatin and Nampt. In Nampt/visfatin-deficient heterozygous mice, impaired glucose tolerance was observed, and Fukuhara et al. described that this phenotype is due to the insufficient insulin-mimetic function of visfatin. Alternatively, however, it is possible that the phenotype is actually due to insufficient NAD biosynthesis in the heterozygous mice, resulting in relatively insufficient activity of critical NAD-dependent enzymes involved in the regulation of glucose metabolism, such as Sirt1. Fukuhara et al. did not examine this possibility, nor did they report insulin levels of the mice during intraperitoneal glucose tests. Additionally, it has recently been reported that certain common polymorphisms in the promoter of the Nampt/PBEF/visfatin gene are associated with fasting insulin levels in a perfect linkage disequilibrium, but not with type 2 diabetes, in a French-Canadian population (Bailey et al., Diabetes, (2006) 55, 2896-2902.

Although a number of papers have been published since this first report of visfatin, the results are contradictory; the physiological relevance of visfatin, therefore, is still in question (Sethi et al., Trends. Mol. Med., (2005) 11, 344-347; Arner, J. Clin. Endocrinol. Metab., (2006) 91, 28-30; Stephens et al., Curr. Opin. Lipidol., (2006) 17, 128-131). For example, one study reported that plasma visfatin concentrations correlate with BMI and percent body fat but not with visceral fat mass or waist-to-hip ratio (Berndt et al., Diabetes, (2005) 54, 2911-2916). Another study reported that plasma visfatin is reduced in human obesity and is not related to insulin resistance (Pagano et al., J. Clin. Endocrinol. Metab., (2006) 91, 3165-3170). On the other hand, still another study reported that increasing plasma visfatin levels are independently and significantly associated with type 2 diabetes even after adjusting known biomarkers (Chen et al., J. Clin. Endocrinol. Metab., (2006) 91, 295-299). Accordingly, it is important to understand whether the NAD biosynthesis function or the insulin-mimetic function is more physiologically relevant in the regulation of glucose metabolism in mammals. It would also be desirable to provide processes and materials useful in NAD biosynthesis and/or the regulation of glucose metabolism in mammals.

SUMMARY OF THE INVENTION

Among the various aspects of the present invention is the provision of processes for regulating the concentration of blood glucose in a mammal. The processes include administering to a mammal a blood glucose concentration-regulating amount of a compound selected from various compounds useful in nicotinamide adenine dinucleotide (NAD) biosynthesis. In one specific aspect of the present invention, a process is described for increasing the concentration of blood glucose in a mammal including administering to a mammal a blood glucose concentration-increasing amount of a compound selected from the group consisting of nicotinamide; salts, derivatives, and prodrugs thereof; and combinations thereof. In another specific aspect of the present invention, a process is described for decreasing the concentration of blood glucose in a mammal including administering to a mammal a blood glucose concentration-decreasing amount of a compound selected from the group consisting of nicotinamide mononucleotide (NMN); salts, derivatives, and prodrugs thereof; and combinations thereof.

Briefly, therefore, the present invention is directed to a process for regulating the concentration of blood glucose in a mammal, the process comprising administering to a mammal a blood glucose concentration-regulating amount of a compound selected from nicotinamide, nicotinamide mononucleotide (NMN), nicotinamide adenine dinucleotide (NAD); salts and prodrugs thereof; and combinations thereof.

Another aspect of the present invention is a recombinant or transformed host cell. The host cell comprises a nucleotide sequence encoding SEQ ID NO: 1; a nucleotide sequence encoding SEQ ID NO: 7; a nucleotide sequence encoding a polypeptide capable of catalyzing the conversion of nicotinamide to nicotinamide mononucleotide (NMN), the an amino acid sequence of the polypeptide comprising the amino acid sequence of SEQ ID NO: 1; a nucleotide sequence encoding a polypeptide capable of catalyzing the conversion of nicotinamide to nicotinamide mononucleotide (NMN), the an amino acid sequence of the polypeptide comprising the amino acid sequence of SEQ ID NO: 7; a nucleotide sequence encoding a polypeptide capable of catalyzing the conversion of nicotinamide to nicotinamide mononucleotide (NMN), the polypeptide having an amino acid sequence with at least about 65% homology to SEQ ID NO: 1 and conservative amino acid substitutions; or a nucleotide sequence encoding a polypeptide capable of catalyzing the conversion of nicotinamide to nicotinamide mononucleotide (NMN), the polypeptide having an amino acid sequence with at least about 65% homology to SEQ ID NO: 7 and conservative amino acid substitutions.

Another aspect of the present invention is a purified polypeptide or protein capable of catalyzing the conversion of nicotinamide to nicotinamide mononucleotide (NMN). The purified polypeptide or protein is selected from the group consisting of SEQ ID NO: 1; SEQ ID NO: 7; a polypeptide capable of catalyzing the conversion of nicotinamide to nicotinamide mononucleotide (NMN), the an amino acid sequence of the polypeptide comprising the amino acid sequence of SEQ ID NO: 1; a polypeptide capable of catalyzing the conversion of nicotinamide to nicotinamide mononucleotide (NMN), the an amino acid sequence of the polypeptide comprising the amino acid sequence of SEQ ID NO: 7; a polypeptide capable of catalyzing the conversion of nicotinamide to nicotinamide mononucleotide (NMN), the polypeptide having an amino acid sequence with at least about 65% homology to SEQ ID NO: 1 and conservative amino acid substitutions; and a polypeptide capable of catalyzing the conversion of nicotinamide to nicotinamide mononucleotide (NMN), the polypeptide having an amino acid sequence with at least about 65% homology to SEQ ID NO: 7 and conservative amino acid substitutions.

Other objects and features will be in part apparent and in part pointed out hereinafter.

BRIEF DESCRIPTION OF THE DRAWINGS

FIG. 4A depicts a gel upon which His-tagged recombinant polypeptides of mouse Nampt and Nmnat, produced in *E. coli*, were purified to homogeneity (see Example 1). FIG. 4B shows the scheme of the NAD biosynthesis reactions in the enzyme-coupled fluorometric assay (see Example 2). The in vitro-synthesized NAD was converted to NADH by alcohol dehydrogenase (ADH), and the fluorescence of the resulting NADH was measured by a fluorometer. PRPP and PPi are phosphoribosyl pyrophosphate and inorganic pyrophosphate, respectively. FIG. 4C is a graph showing production of NADH (pM) as a function of time (min) measured in the enzyme-coupled fluorometric assay using purified Nampt and Nmnat recombinant polypeptides (see Example 2). Filled squares indicate the reaction with nicotinamide, PRPP and ATP. Open squares and triangles indicate reactions without nicotinamide and PRPP, respectively. FIG. 4D depicts high performance liquid chromatography elutions of the products of mouse Nampt reaction (see Example 2). Elution times for each chemical were confirmed by running standards in the same HPLC conditions.

FIG. 5A is a Western blot depicting the distribution of Nampt in C57BL/6 mouse tissues (see Example 4). WAT and BAT are white adipose tissue and brown adipose tissue, respectively. FIG. 5B is a Western blot depicting the fasting-induced increase of Nampt in BAT of fed and fasted C57BL/6 mice (see Example 4). FIG. 5C depicts a bar graph quantifying the Western blot results shown in FIG. 5B. The single asterisk indicates $p<0.05$.

In FIG. 6A intracellular Nampt and extracellular (e.g., secreted) Nampt were analyzed in cell extracts and culture supernatant during differentiation of HIB-1B brown preadipocytes (see Example 5). In the upper panel of FIG. 6A, confluent cultures of HIB-1B cells were differentiated and cell extracts were prepared and analyzed at the indicated days. In the middle panel of FIG. 6A, culture supernatant collected at the indicated days was analyzed. In the lower panel of FIG. 6A, differentiated HIB-1B cells were cultured in media without serum from day 6 to day 8, and the culture supernatant was collected and analyzed at day 8. In FIG. 6B Nampt was analyzed during differentiation of 3T3-L1 white preadipocytes (see Example 5). The cell extract from Nampt-overexpressing fibroblasts (Nampt1) was loaded as a reference in each analysis. eNampt and iNampt are an intracellular version of Nampt and an extracellular version of Nampt, respectively.

In FIG. 7A mouse NIH3T3 fibroblast cell lines overexpressing Nampt (Nampt1) and FLAG®-tagged Nampt (Nampt-FLAG®) were established (see Example 5). Intracellular Nampt and extracellular (e.g., secreted) Nampt were analyzed in cell extract and culture medium, respectively, by Western blotting with an anti-Nampt antibody. FLAG®-tagged Nampt was also confirmed with an anti-FLAG® antibody (data not shown). In FIG. 7B, human HEK293 embryonic kidney and mouse Hepa1-6 hepatocyte cell lines overexpressing Nampt and Nampt-FLAG® were established (see Example 5). Intracellular Nampt was detected in cell extract. FLAG®-tagged Nampt was also confirmed in both cell lines (data not shown). For HEK293 cells, extracellular Nampt was analyzed in culture medium. Closed and open arrowheads indicate Nampt and FLAG®-tagged Nampt, respectively.

In FIG. 9A, the concentration of the extracellular version of Nampt in the overnight HIB-1B culture supernatant is estimated as ~100 ng/ml by comparing the amount of the extracellular version of Nampt in the supernatant to standards of the purified His-tagged Nampt protein (see Example 7). In FIG. 9B the HIB-1B culture supernatant was fractionated with Phenyl hydrophobic and then Q anion exchange columns (see Example 7). The band indicated by an arrow was analyzed by nano-LC-FT-MS and confirmed to contain the Nampt protein. In FIG. 9C fractions after each Phenyl and Q column were examined by Western blotting with an anti-Nampt polyclonal antibody (see Example 7). Fractions indicated by brackets were combined for further purification or analysis.

FIG. 12A is a Western blot depicting enzyme expression of two Nampt-, one Nmnat- and one Sir2α-overexpressing NIH3T3 lines and two neomycin-resistant controls (see Example 3). FIG. 12B depicts total cellular NAD levels in enzyme-overexpressing and nicotinamide-treated NIH3T3 cells as well as original NIH3T3 and neomycin-resistant controls. The averages and standard deviations were calculated from three to four independent assays and compared with one-way ANOVA and the Bonferroni multiple comparison test (see Example 3). Only Nampt-overexpressing cell lines (Nampt 1 and 2) show statistically significant increases in total cellular NAD levels. A triple asterisk indicates P<0.001. A double asterisk indicates P<0.01 or 0.001.

FIG. 14A shows establishment of NIH3T3 cell lines overexpressing Nmnat and Sir2α proteins fused to GFP at their C-termini (Nmnat-GFP and Sir2α-GFP). An NIH3T3 cell line expressing GFP protein only was also established. FIG. 14B depicts transient expression in NIH3T3 cells of the Nampt polypeptide fused to GFP at its C-terminus (Nampt-GFP) and the control GFP protein. Live GFP-positive cells were examined and photographed under a fluorescent microscope. Nampt-GFP was mainly localized in cytoplasm, as described in Kitani et al., FEBS Lett., (2003) 544, 74-78.

FIG. 15 is a comparison of the crystal structures of mouse nicotinamide phosphoribosyltransferase (Nampt) bound to nicotinamide mononucleotide (NMN) and *T. acidophilum* nicotinic acid phosphoribosyltransferase (Npt) bound to nicotinic acid mononucleotide (NaMN). See Wang et al., Nat. Struc. Mol. Bio., (2006) 13, 661-662. The crystal structure clearly shows that Nampt is a dimeric type II phosphoribosyltransferase. Although Nampt bears no substantial sequence identity/homology to other phosphoribosyltransferases, Nampt shows a remarkable topological similarity to the dimeric nicotinic acid phosphoribosyltransferase. The Nampt dimer has two active sites lying at the dimer interface, where two NMN molecules bind. Interactions between NMN and the two Nampt monomers also support the notion that the dimerization is critical for its enzymatic activity (see Wang et al., supra; see also Examples 13 and 15 and FIG. 19C).

In FIG. 17A, the Nampt-FLAG® protein was detected in both cell extracts and culture supernatants, while the Dhfr-FLAG® protein was detected only in cell extracts, suggesting that the production of extracellular Nampt is not due to cell lysis or death. In FIG. 17B, the Nampt-FLAG® and Ppl/prolactin (Ppl)-FLAG® proteins were detected in both cell extracts and culture supernatants. In FIG. 17C, while the Prl-FLAG® secretion was inhibited by brefeldin A (BFA), the extracellular Nampt was not inhibited by BFA, suggesting that the extracellular Nampt secretion is due to a non-classical secretory pathway. (See Example 14).

FIG. 18A shows the detection of Nampt-FLAG® and Dhfr-FLAG® in cell extracts and supernatants of CHO cells. FIG. 18B shows the detection of Nampt-FLAG® and Ppl/Prl-FLAG® in cell extracts and culture supernatants. FIG. 18C shows the effect of brefeldin A (BFA) in Nampt-FLAG® and Prl-FLAG® secretion. (See Example 14).

FIG. 19A is a scheme of the insertion site of the exon-trap β-geo construct of the Nampt genomic locus. The β-geo construct was inserted 127 bp downstream of the exon 8 of the Nampt gene. Arrows labeled A, B, C, D, E, and F indicated genotyping PCR primers. FIG. 19B is an image of a gel showing representative results of genotyping PCR reactions. The fatty acid binding protein 1 (Fabp1) gene provided a positive control. Fig. C is an image showing that the β-geo insertion truncates the C-terminal portion of Nampt and produced a ~190 kDa fusion protein between Nampt (amino acid 1-363) and β-geo. This fusion protein lacks Gly 384 and Arg 392, both of which contribute to the catalytic site of Nampt, and therefore should be enzymatically deficient. (See Example 15).

FIG. 21A is a graph showing body weight of Nampt$^{+/-}$ and Nampt$^{+/+}$ mice at 8 weeks of age. +/+ males (n=7), +/− males (n=12), +/+ females (n=15), +/− females (n=9). FIG. 21B is a graph showing fasted glucose levels. +/+ males (n=6), +/− males (n=10), +/+ females (n=13), +/− females (n=9). FIG. 21C is a graph showing intraperitoneal glucose tolerance tests (IPGTTs). Nampt$^{+/+}$ (n=18) and Nampt$^{+/-}$ (n=13) females were injected with PBS and fasted for 12-14 hrs. Dextrose (3 g/kg body weight) was injected intraperitoneally, and blood glucose levels were measured. A single asterisk indicates P<0.05, and a double asterisk indicates P<0.01. FIG. 21D is a graph of plasma insulin levels in Nampt$^{+/+}$ and Nampt$^{+/-}$ female mice at 0 and 30 min time points in IPGTTs shown in FIG. 21C. A double asterisk indicates P<0.05. FIG. 21E is a graph of insulin tolerant tests (ITTs). Nampt$^{+/+}$ (n=13) and Nampt$^{+/-}$ (n=9) females were injected with human insulin (0.75 U/kg body weight) after fasting for 4 hrs, and blood glucose levels were measured. FIG. 21F is a graph showing insulin secreted (ng/ml/hr) from Nampt$^{+/+}$ and Nampt$^{+/-}$ islets at the indicated glucose concentrations (n=4). See Example 17.

FIG. 22A is a graph showing IPGTTs after NMN administration. The same Nampt$^{+/+}$ (n=11) and Nampt$^{+/-}$ (n=8) individuals that were used for IPGTTs shown in FIG. 21C were injected with NMN (500 mg/kg body weight) ~14 hrs prior to IPGTTs. FIG. 22B is a graph showing plasma insulin levels at 0 and 30 min time points in IPGTTs shown in FIG. 22A. FIG. 22C is a graph showing that the injection of the recombinant Nampt protein (1000 pmole) into wild-type mice causes no decrease in blood glucose levels (n=3), contrary to the results described by Fukuhara et al. (Science, (2005) 307,426-430). See Example 18.

ABBREVIATIONS AND DEFINITIONS

Figure 1:
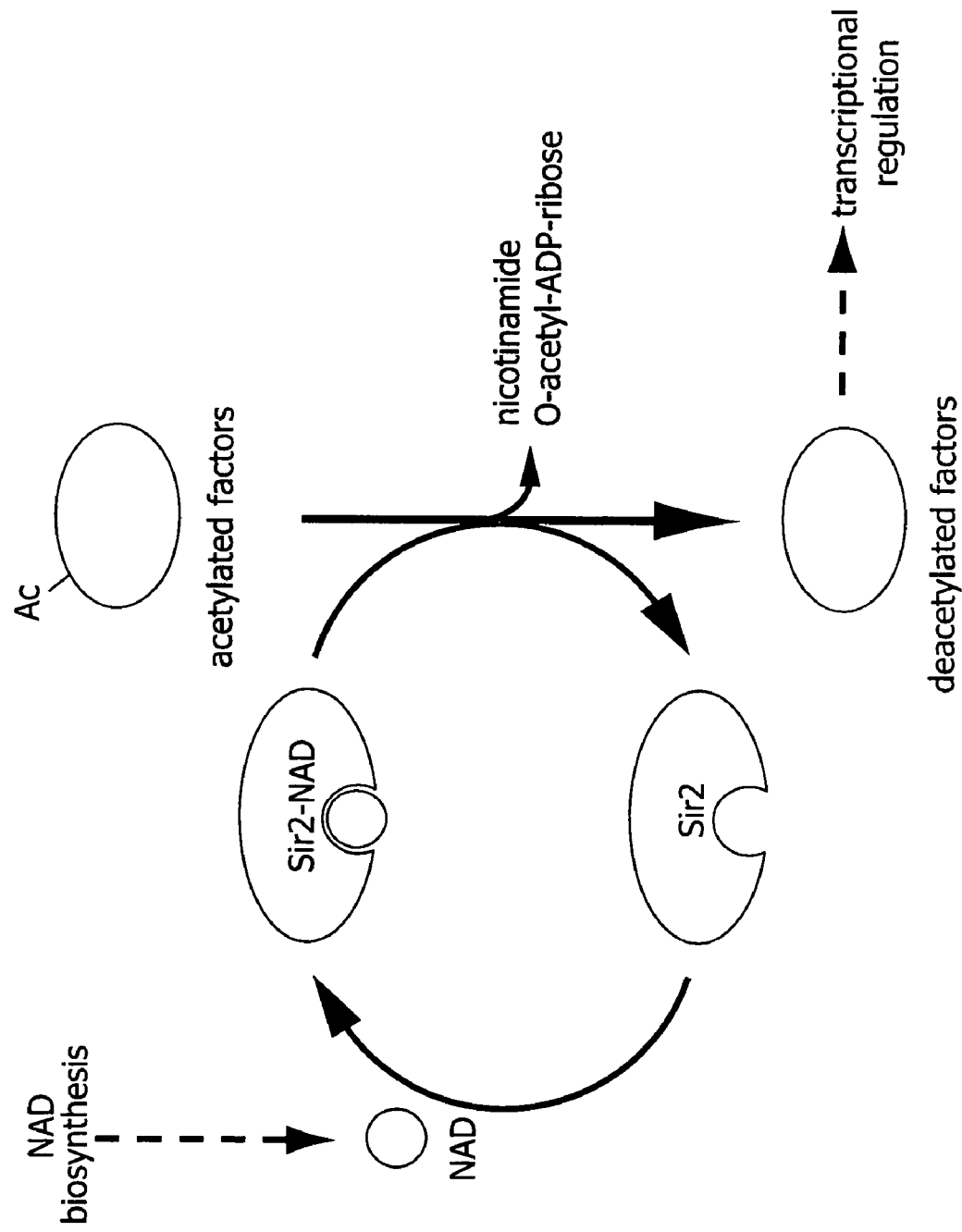
FIG. 1 is a schematic representation of the NAD-dependent deacetylation reaction of Sir2. Sir2 proteins couple deacetylation of protein substrates to cleavage of the high-energy bond between ADP-ribose and nicotinamide in NAD. The acetyl group (Ac) is transferred to ADP-ribose, forming O-acetyl-ADP-ribose. Sir2 proteins deacetylate histones and a variety of transcriptional regulatory factors.
Figure 2:
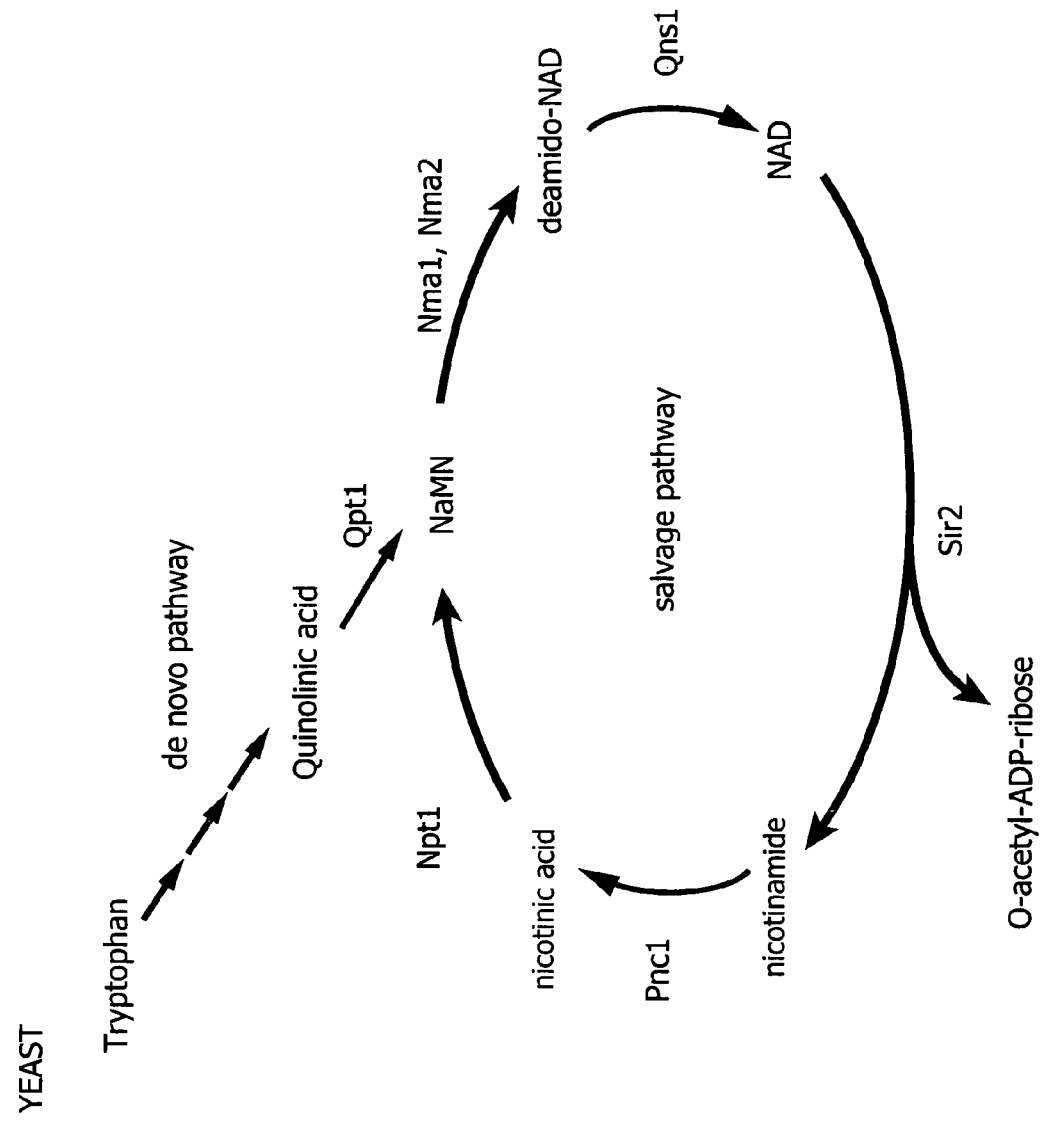
FIG. 2 is a schematic representation of the de novo and salvage NAD biosynthesis pathways in the budding yeast *Saccharomyces cerevisiae*; Pnc1, Npt1, Nma1 and Nma2, Qns1, and Qpt1 are nicotinamidase, nicotinic acid phosphoribosyltransferase, nicotinic acid mononucleotide adenylyltransferase 1 and 2, NAD synthetase, and quinolinic acid phosphoribosyltransferase, respectively. This pathway is also conserved in *C. elegans, Drosophila*, and other invertebrates.

The following definitions and methods are provided to better define the present invention and to guide those of ordinary skill in the art in the practice of the present invention. Unless otherwise noted, terms are to be understood according to conventional usage by those of ordinary skill in the relevant art.

The term "amino acid" includes naturally occurring amino acids as well as non-naturally occurring amino acids, including amino acid analogs and derivatives. The latter includes molecules containing an amino acid moiety. One skilled in the art will recognize that reference herein to an amino acid includes, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids. For all the amino acid sequences disclosed herein, it is understood that equivalent nucleotides and amino acids can be substituted into the sequences without affecting the function of the sequences. Such substitution is within the ability of a person of ordinary skill in the art.

The term "nucleic acid" as used herein generally refers to a molecule or strand of DNA, RNA, or derivatives or analogs thereof including one or more nucleobases. Nucleobases include purine or pyrimidine bases typically found in DNA or RNA (e.g., adenine, guanine, thymine, cytosine, and/or uracil). The term "nucleic acid" also includes oligonucleotides and polynucleotides. Nucleic acids may be single-stranded molecules, or they may be double-, triple- or quadruple-stranded molecules that may include one or more complementary strands of a particular molecule.

As used herein, "polynucleotide" and "oligonucleotide" are used interchangeably and mean a polymer of at least two nucleotides joined together by phosphodiester bonds and may consist of either ribonucleotides or deoxyribonucleotides.

The term "polypeptide" when used herein refers to two or more amino acids that are linked by peptide bond(s), regardless of length, functionality, environment, or associated molecule(s). Typically, the polypeptide is at least four amino acid residues in length and can range up to a full-length protein. As used herein, "polypeptide," "peptide," and "protein" are used interchangeably.

As used herein, "sequence" means the linear order in which monomers occur in a polymer, for example, the order of amino acids in a polypeptide or the order of nucleotides in a polynucleotide.

As used herein, "transfect," "transfection," and "transfecting" refer to the delivery or transfer and uptake of nucleic acids into cultured cells. It will be understood by one of skill in the art that the terms "transfect," "transfection," and "transfecting" encompass both the "stable" and the "transient" transfection of cultured cells. In transient transfection, for example, recombinant nucleic acid is introduced into a cell to obtain the temporary expression of the target gene. Because the nucleic acid is typically not stably integrated into the chromosome of the host cell, the nucleic acid is eventually degraded or catabolized by nucleases, or is diluted by cell division. Alternatively, in stable or permanent transfection, the cells are co-transfected with an additional gene that provides some selection advantage, allowing the few cells that happen to have the desired gene incorporated into its genome to be selected and proliferated over a period of time until the culture substantially consists of only the cells that permanently express the desired gene. As between stable and transient transfection methods, therefore, the initial delivery or transfer and uptake of nucleic acid, is essentially the same. See, e.g., Sambrook et al. (2001) "Molecular Cloning, A Laboratory Manual," 3d ed., Cold Spring Harbor Laboratory Press.

Various embodiments of the present invention rely on altering biological material using molecular techniques. Molecular techniques refers to procedures in which DNA is manipulated in a test tube during at least one stage of the process, such as the direct manipulation of DNA or the use of shuttle host such as bacterium. Additional examples of molecular techniques include, for example, methods of using PCR to multiply a nucleic acid of interest for introduction and expression in a mammal or mammal cell via expression vectors or direct introduction of the nucleic acid; methods of using nucleic acid libraries to determine, isolate, introduce, and express a nucleic acid of interest into a mammal or mammalian cell via expression vectors or direct introduction of the nucleic acid; isolation of nucleic acid segments, concatemerization of said nucleic acid segments into a larger nucleic acid, introduction, and expression of the same in a mammal or mammalian cell via expression vectors or direct introduction of the nucleic acid; and isolation of mRNA from a gene, creation of cDNA from the mRNA by reverse transcription, and introduction and expression of the same in a mammal or a cell via expression vectors or direct introduction of the nucleic acid. Such methods are well known in the art and are described in, for example, Sambrook et al. (2001) "Molecular Cloning, A Laboratory Manual," 3d ed., Cold Spring Harbor Laboratory Press.

DETAILED DESCRIPTION OF THE INVENTION

In accordance with the present invention, provided are processes for regulating the concentration of blood glucose in a mammal. For example, the concentration of blood glucose can be increased as compared to a previously determined level according to the processes described herein. Alternatively, the concentration of blood glucose may be decreased as compared to a previously determined level according to the processes described herein. By way of further example, the concentration of blood glucose may be maintained at a previously determined level according to the processes described herein. Also provided are processes for increasing the concentration of blood glucose in a mammal. Further provided is a novel polypeptide useful in nicotinamide adenine dinucleotide (NAD) biosynthesis and processes for producing the novel polypeptide.

Biochemical Characterization of NAMPT and NMNAT

Figure 3:
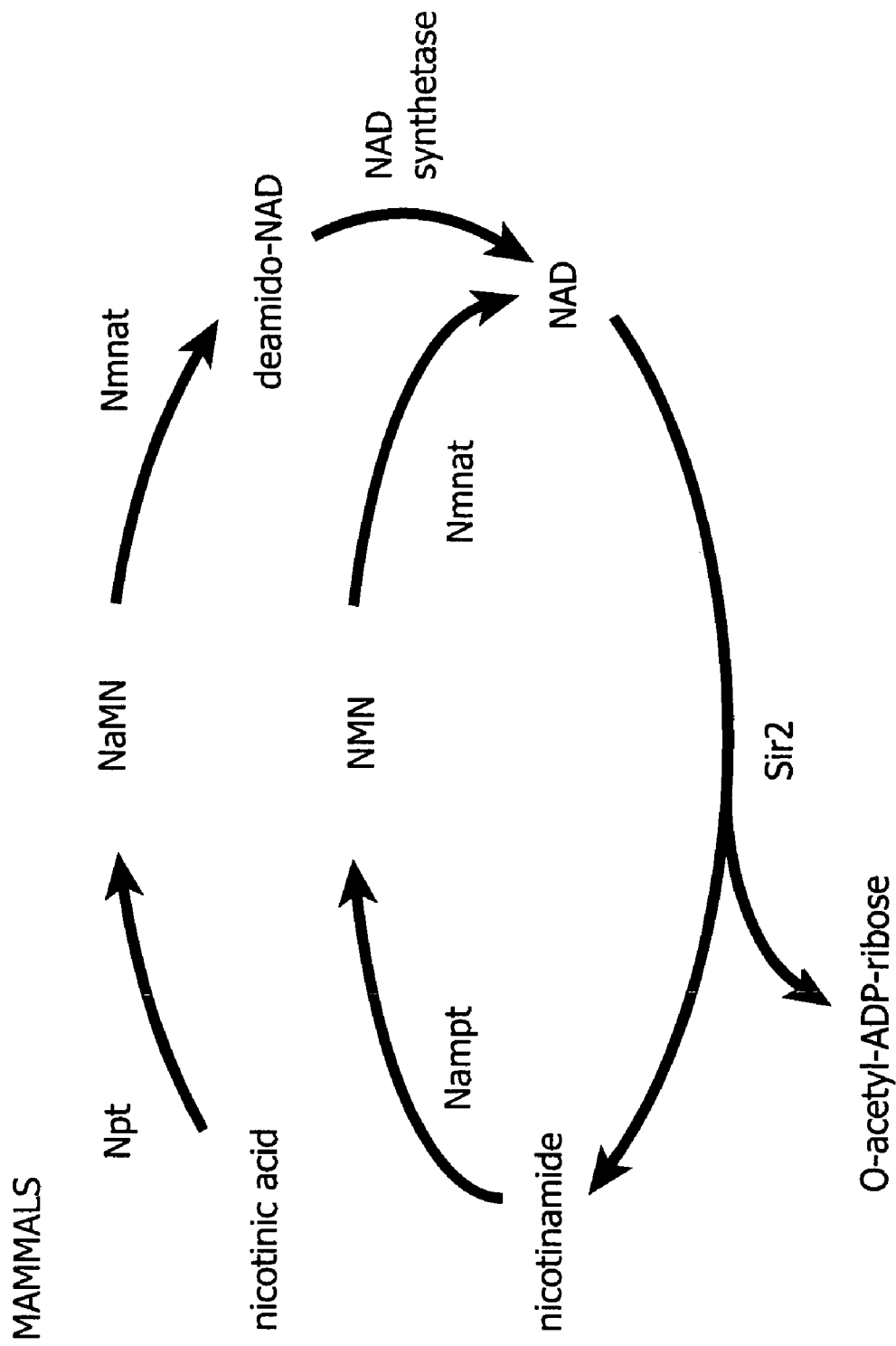
FIG. 3 is a schematic representation of the NAD biosynthesis pathways from nicotinamide and nicotinic acid in mammals. The de novo pathway from tryptophan is not shown in this scheme. These pathways, including the de novo pathway, are conserved throughout vertebrates. Nicotinamide is the main precursor for NAD biosynthesis in mammals. Npt, Nampt, and Nmnat are nicotinic acid phosphoribosyltransferase, nicotinamide phosphoribosyltransferase, and nicotinamide/nicotinic acid mononucleotide adenylyltransferase, respectively. Multiple enzymes break NAD down to nicotinamide and ADP-ribose, but only Sir2 is shown here. NaMN and NMN are nicotinic acid mononucleotide and nicotinamide mononucleotide, respectively.

Mammals predominantly use nicotinamide to synthesize NAD (see, e.g., FIG. 3). As noted above, this NAD biosynthesis pathway starting from nicotinamide is catalyzed by two enzymes, Nampt and Nmnat. PCT Publication No. WO 2006/041624, hereby incorporated by reference herein, describes reconstituting this NAD biosynthesis pathway in vitro with His-tagged recombinant Nampt and Nmnat enzymes (see, e.g., FIG. 4A; Example 1) and developing an enzyme-coupled fluorometric assay (see, e.g., FIG. 4B, Example 2), which provides an important tool to measure Nampt activity. In particular, the enzyme-coupled fluorometric assay may be utilized to measure the enzymatic activity of various compounds useful in NAD biosynthesis.

In the enzyme-coupled reaction, NAD is converted to NADH by alcohol dehydrogenase, and the fluorescence of NADH is detected in a fluorometer. As disclosed in PCT Publication No. WO 2006/041624, no NAD was produced in the absence of nicotinamide or PRPP, the substrates of Nampt (FIG. 4C; see also Example 2). PCT Publication No. WO 2006/041624 also described an HPLC-based assay to directly detect NMN, the product of the Nampt reaction with nicotinamide (FIG. 4D; see also Example 2). According to the results described therein, Nampt failed to catalyze the synthesis of nicotinic acid mononucleotide from nicotinic acid and PRPP, confirming the substrate specificity of this enzyme (see also Revollo et al., *J. Biol. Chem.*, (2004) 279, 50754-50763). Using the enzyme-coupled fluorometric assay, the kinetic parameters of purified recombinant mouse Nampt and Nmnat were determined for nicotinamide and NMN, respectively (Table 1).

TABLE 1

KINETIC PARAMETERS OF PURIFIED RECOMBINANT MOUSE NAMPT AND NMNAT

| Enzyme | Substrate | $K_m$ (µM) | $V_{max}$ (mmol/min/mg) | $k_{cat}$ (sec$^{-1}$) | catalytic efficiency ($k_{cat}/K_m$, M$^{-1}$sec$^{-1}$) |
|---|---|---|---|---|---|
| Nampt | Nicotinamide | 0.92 | 0.021 | 0.020 | $2.17 \times 10^4$ |
| Nmnat | NMN | 20.1 | 31.4 | 20.0 | $9.95 \times 10^5$ |

As illustrated in Table 1, Nampt shows very high affinity for its substrate, nicotinamide ($K_m$=0.92 µM), while the catalytic efficiency of Nampt is ~46-fold less than that of Nmnat, suggesting that the reaction of Nampt is the rate-limiting step in the synthesis of NAD from nicotinamide. These findings strongly suggest that Nampt plays a critical role as the rate-limiting component in mammalian NAD biosynthesis starting from nicotinamide. The enzyme-coupled fluorometric assay may therefore be useful in determining the enzymatic activity of purified polypeptides useful in NAD biosynthesis, and in particular, polypeptides corresponding to an extracellular version of Nampt, described in further detail below (see also Example 11).

Effects of NAD Biosynthesis on Glucose Metabolism and Compounds Useful in NAD Biosynthesis It is believed that Nampt may synthesize NMN in blood circulation (i.e., extracellularly) and affect glucose metabolism. For example, NMN (produced from nicotinamide) may trigger a physiological response that affects the metabolism of glucose in the blood. By way of further example, compounds useful in NAD biosynthesis such as, for example, nicotinamide, nicotinamide mononucleotide (NMN), Nampt, or NAD itself, may be administered to a mammal in some manner (such as by injection or ingestion (e.g., as vitamin B3)). The compounds useful in NAD biosynthesis may then be distributed to the organs and/or tissues of the mammal through blood circulation. Where nicotinamide is the NAD biosynthesis compound that is administered, for example, it can permeate the cells of the mammal, e.g., by diffusion and/or transport, and be converted to NMN by an intracellular version of Nampt, and then to NAD by Nmnat. Concurrently or substantially concurrently, a significant fraction of nicotinamide may be converted to NMN by an extracellular version of Nampt in blood or other extracellular compartment. NMN produced by this method could also be distributed to various organs and/or tissues through blood circulation and transported into cells. Once NMN is transported into the cell, it can be rapidly converted to NAD by Nmnat which, as noted above, is a more enzymologically efficient reaction than nicotinamide to NMN by Nampt. The distribution of NMN through blood circulation, for example, may be particularly important for organs and/or tissues that do not have sufficient levels of the intracellular version of Nampt to synthesize NAD from nicotinamide, such as the brain and pancreas. Those organs may be more susceptible to alterations in Nampt activity and, therefore, to alterations in plasma NMN levels. Accordingly, plasma NMN levels may be an important biomarker for metabolic complications such as type 2 diabetes. Through the synthesis of NMN from nicotinamide in intracellular and extracellular compartments, both extracellular and intracellular versions of Nampt may be useful in regulating NAD biosynthesis at a systemic level.

NAD biosynthesis may also play a role in blood glucose metabolism by altering the activity of NAD-dependent enzymes, such as the mammalian Sir2 ortholog, Sirt1. For example, researchers have demonstrated that Sirt1 promotes insulin secretion in pancreatic β cells in response to high glucose (Moynihan et al., Cell Metab., (2005) 2, 105-117), and it has also been reported that Sirt1 regulates glucose production in the liver (Rodgers et al., Nature, (2005) 434, 113-118), and fat mobilization in adipose tissues (Bordone et al., Nat. Rev. Mol. Cell Biol., (2005) 6, 298-30). Accordingly, Sirt1 may be an important mediator that connects NAD biosynthesis to glucose metabolism regulation and, consequently, the regulation of the concentration of blood glucose in a mammal.

Regulating Blood Glucose Concentration

One aspect of the present invention is a process for regulating the concentration of blood glucose in a mammal. As utilized herein, regulating the concentration of blood glucose refers to any increase, decrease, and/or maintenance in or of the concentration of blood glucose as compared to a previously determined level.

Blood glucose concentration-regulating compounds described in further detail below may be administered to a mammal in need of such treatment. For example, the mammal may require an increase in blood glucose concentration. Alternatively, the mammal may require a decrease in blood glucose concentration. Or, the mammal may require maintenance of blood glucose concentration above, at, or below a particular level or within a particular range (e.g., through a series of increases and/or decreases, or through no increases or decreases). The blood glucose concentration-regulating compounds may also be administered to a mammal as a prophylactic measure; that is, the mammal is in need of treatment to prevent or delay the occurrence or onset of a medical condition such as, for example, type 1 or type 2 diabetes.

The ability to regulate the concentration of blood glucose in a mammal according to the processes described herein (e.g., by administering to a mammal a blood glucose regulating amount of a compound selected from nicotinamide, nicotinamide mononucleotide (NMN), nicotinamide adenine dinucleotide (NAD); salts, derivatives, and prodrugs thereof; a purified polypeptide useful in NAD biosynthesis; and combinations thereof) may be advantageous in the treatment and/or prevention of a variety of complications, diseases, and/or illnesses. In general, the present invention may be utilized to treat a variety of acute, intermediate stage, and chronic conditions that may be affected by systemic NAD biosynthesis either directly or indirectly.

For example, the regulation of blood glucose concentration may be effective in the treatment and/or prophylaxis of such medical conditions as brain ischemia-induced hypoglycemia, hypoglycemic brain injury caused by, e.g., congenital hyperinsulinism in children, and/or other conditions that severely reduce blood glucose levels. Alternatively, the regulation of blood glucose concentration may be effective in counteracting the effects of the injection of an excessive amount of insulin, or an insufficient dietary or vitamin intake (e.g., deficiencies in vitamin B3 (niacin, which is derived from nicotinic acid and nicotinamide) can result in pellagra, the classic niacin deficiency disease, characterized by bilateral dermatitis, diarrhea, and dementia).

Further, regulation of blood glucose concentration may be effective in the treatment and/or prophylaxis of hypoglycemia, hyperglycemia, impaired glucose tolerance, impaired fasting glucose, and type 1 and type 2 diabetes.

The regulation of blood glucose concentration according to the methods described herein may also be advantageous in counteracting the effects of blood glucose concentration-decreasing drugs such as acetaminophen, alcohol, anabolic steroids, clofibrate, disopyramide, gemfibrozil, monoamine oxidase inhibitors (MAOIs), pentamidine, or sulfonylurea medications (such as glipizide, glyburide, and glimepiride).

Other conditions having a less direct connection (or at least not an apparent connection) to NAD biosynthesis, such as dementia, may also be beneficially treated and/or prevented by blood glucose regulation.

The increase, decrease, and/or maintenance of blood glucose concentration can be quantified, for example, by percentage above, below, or in between one or more previously determined levels, or can be quantified by a particular blood glucose concentration or a range thereof.

For example, the blood glucose concentration may be increased to at least about 5% above a previously determined level; to at least about 10% above a previously determined level; to at least about 25% above a previously determined level; to at least about 50% above a previously determined level; to at least about 75% above a previously determined level; to at least about 100% above a previously determined level; to at least about 150% above a previously determined level; or to at least about 200% above a previously determined level. By way of another example, the blood glucose concentration may be decreased to at least about 5% below a previously determined level; to at least about 10% below a previously determined level; to at least about 25% below a previously determined level; to at least about 50% below a previously determined level; to at least about 75% below a previously determined level; to at least about 100% below a previously determined level; to at least about 150% below a previously determined level; or to at least about 200% below a previously determined level. By way of yet another example, the blood glucose concentration may be maintained (e.g., by a series of increases and/or decreases, or by no increases and/or decreases) at a concentration that is no more than 50% greater or 50% less than a previously determined level; e.g., no more than 40% greater or 40% less; no more than 30% greater or 30% less; no more than 20% greater or 20% less; no more than 10% greater or 10% less; or no more than 5% greater or 5% less.

Alternatively, the blood glucose concentration may be maintained (e.g., by a series of increases and/or decreases, or by no increases and/or decreases) at, above, or below a particular blood glucose concentration or within a desired range of blood glucose concentrations. For example, the blood glucose concentration may be maintained at a concentration of greater than about 60 mg/dL; greater than about 70 mg/dL; greater than about 100 mg/dL; greater than about 110 mg/dL; or greater than about 125 mg/dL. Alternatively, the blood glucose concentration may be maintained at a concentration of less than about 200 mg/dL; less than about 175 mg/dL; less than about 150 mg/dL; less than about 125 mg/dL; less than about 110 mg/dL; or less than about 100 mg/dL. By way of another example, the blood glucose concentration may be maintained at a concentration of from about 60 mg/dL to about 140 mg/dL; from about 90 mg/dL to about 130 mg/dL; from about 100 mg/dL to about 125 mg/dL; or from about 110 mg/dL to about 125 mg/dL.

Blood Glucose Concentration-Regulating Compounds

As noted above, blood glucose concentration-regulating compounds that may be utilized include nicotinamide, nicotinamide mononucleotide (NMN), nicotinamide adenine dinucleotide (NAD); salts, derivatives, and prodrugs thereof; a purified polypeptide useful in NAD biosynthesis; and combinations thereof.

Nicotinamide, which corresponds to Formula (1),

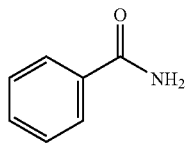

(1)

is one of the two principal forms of the B-complex vitamin niacin. The other principal form of niacin is nicotinic acid; nicotinamide, rather than nicotinic acid, however, is the major substrate for nicotinamide adenine dinucleotide (NAD) biosynthesis in mammals, as discussed in detail herein. Nicotinamide, in addition to being known as niacinamide, is also known as 3-pyridinecarboxamide, pyridine-3-carboxamide, nicotinic acid amide, vitamin B3, and vitamin PP. Nicotinamide has a molecular formula of $C_6H_6N_2O$ and its molecular weight is 122.13 Daltons. Nicotinamide is commercially available from a variety of sources. The blood glucose concentration-regulating compound may also be a pharmaceutically acceptable salt, derivative, or prodrug of nicotinamide, or combinations thereof.

Nicotinamide mononucleotide (NMN), which corresponds to Formula (2),

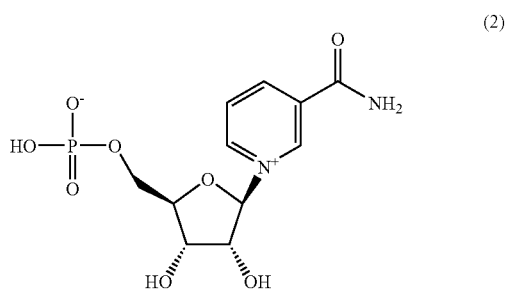

(2)

is produced from nicotinamide in the NAD biosynthesis pathway, a reaction that is catalyzed by Nampt. NMN is further converted to NAD in the NAD biosynthesis pathway, a reaction that is catalyzed by Nmnat. Nicotinamide mononucleotide (NMN) has a molecular formula of $C_{11}H_{15}N_2O_8P$ and a molecular weight of 334.22. Nicotinamide mononucleotide (NMN) is commercially available from such sources as Sigma-Aldrich (St. Louis, Mo.). The blood glucose concentration-regulating compound may also be a pharmaceutically acceptable salt, derivative, or prodrug of nicotinamide mononucleotide (NMN), or combinations thereof.

Nicotinamide adenine dinucleotide (NAD), which corresponds to Formula (3):

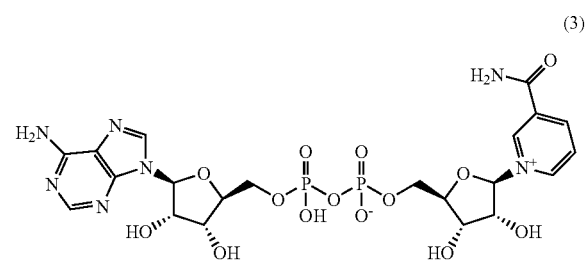

(3)

is produced from the conversion of nicotinamide to NMN, which is catalyzed by Nampt, and the subsequent conversion of NMN to NAD, which is catalyzed by Nmnat. Nicotinamide adenine dinucleotide (NAD) has a molecular formula of $C_{21}H_{27}N_7O_{14}P_2$ and a molecular weight of 663.43. Nicotinamide adenine dinucleotide (NAD) is commercially available from such sources as Sigma-Aldrich (St. Louis, Mo.). The blood glucose concentration-regulating compound may also be a pharmaceutically acceptable salt, derivative, or prodrug of nicotinamide adenine dinucleotide (NAD), or combinations thereof.

Additionally or alternatively, the blood glucose concentration-regulating compound may be a purified polypeptide useful in NAD biosynthesis such as described in detail below. In a particular embodiment, the purified polypeptide corresponds to Nampt; in another embodiment, the purified polypeptide corresponds to an extracellular version of Nampt. As discussed in detail above, Nampt catalyses the conversion of nicotinamide to NMN and has been identified as the rate-limiting compound in NAD biosynthesis. Accordingly, administration of a purified polypeptide corresponding to an extracellular version of Nampt in conjunction with the blood glucose concentration-regulating compounds described above may be particularly advantageous. In a particular embodiment, the Nampt has a polypeptide sequence selected from the group consisting of SEQ ID NO: 1; SEQ ID NO: 7; a polypeptide capable of catalyzing the conversion of nicotinamide to nicotinamide mononucleotide (NMN), an amino acid sequence of the polypeptide comprising the amino acid sequence of SEQ ID NO: 1; a polypeptide capable of catalyzing the conversion of nicotinamide to nicotinamide mononucleotide (NMN), an amino acid sequence of the polypeptide comprising the amino acid sequence of SEQ ID NO: 7; a polypeptide capable of catalyzing the conversion of nicotinamide to nicotinamide mononucleotide (NMN), the polypeptide having an amino acid sequence with at least about 65% homology to SEQ ID NO: 1 and conservative amino acid substitutions; and a polypeptide capable of catalyzing the conversion of nicotinamide to nicotinamide mononucleotide (NMN), the polypeptide having an amino acid sequence with at least about 65% homology to SEQ ID NO: 7 and conservative amino acid substitutions.

Any one (or a combination) of the blood glucose concentration-regulating compounds may be employed. For example, nicotinamide and a purified polypeptide useful in NAD biosynthesis (such as extracellular Nampt) may be administered together or in succession. Alternatively, nicotinamide mononucleotide (NMN) may be administered alone. Where the mammal has sufficient (or elevated) levels of nicotinamide in the blood, a purified polypeptide useful in NAD biosynthesis (such as extracellular Nampt) may also be administered alone.

As noted above, the blood glucose concentration-regulating compound may be a salt of nicotinamide, nicotinamide mononucleotide (NMN), or nicotinamide adenine dinucleotide (NAD). Typically, the salt will be a pharmaceutically acceptable salt; that is, a salt prepared from pharmaceutically acceptable non-toxic acids, including inorganic acids and organic acids. Suitable non-toxic acids include inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N"-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like. Pharmaceutically acceptable salts of the blood glucose concentration-regulating compounds can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

Since prodrugs are known to enhance numerous desirable pharmaceuticals (e.g., solubility, bioavailability, manufacturing), the blood glucose concentration-regulating compound may be delivered in prodrug form. Thus, the present invention is intended to cover prodrugs of blood glucose concentration-regulating compounds, methods of delivering the same and compositions containing them. "Prodrugs" include any covalently bonded carriers which release an active parent drug in vivo when such prodrug is administered to a mammalian subject. Prodrugs are generally prepared by modifying functional groups present in the compound in such a way that the modifications are cleaved, either in routine manipulation or in vivo, to the parent compound. Prodrugs include compounds of the present invention wherein a hydroxyl or amino group is bonded to any group that, when the prodrug is administered to a mammalian subject, cleaves to form a free hydroxyl or free amino group, respectively. Examples of prodrugs include, but are not limited to, acetate, formate, and benzoate derivatives of alcohol and amine functional groups in the compounds and conjugates of the present invention. Prodrugs of the blood glucose-regulating compound are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. Prodrugs may refer to compounds that are rapidly transformed in vivo to yield the blood glucose concentration-regulating compound, for example by hydrolysis in blood. A thorough discussion of prodrugs is provided in the following: Design of Prodrugs, H. Bundgaard, ea., Elsevier, 1985; Methods in Enzymology, K. Widder et al, Ed., Academic Press, 42, p. 309-396, 25 1985; A Textbook of Drug Design and Development, Krogsgaard-Larsen and H. Bundgaard, ea., Chapter 5; "Design and Applications of Prodrugs" p. 113-191, 1991; Advanced Drug Delivery Reviews, H. Bundgard, 8, p. 1-38, 1992; Journal of Pharmaceutical Sciences, 77, p. 285, 30 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ea., American Pharmaceutical Association and Pergamon Press, 1987, which are incorporated herein by reference.

Dosage/Amount of the Blood Glucose Concentration-Regulating Compound and Time Course of Treatment The dose or amount of the blood glucose concentration-regulating compound administered to the mammal should be an effective amount for the intended purpose, i.e., regulating the concentration of blood glucose as described herein. Generally speaking, the effective amount of the blood glucose concentration-regulating compound administered to the mammal can vary according to a variety of factors such as, for example, the age, weight, sex, diet, route of administration, and the medical condition of the mammal. Specifically preferred doses are discussed more fully below. It will be understood, however, that the total daily usage of the compounds described herein will be decided by the attending physician or veterinarian within the scope of sound medical judgment.

The specific therapeutically effective dose level for any particular mammal will depend upon a variety of factors including the disorder being treated and the severity of the disorder; activity of the specific compound(s) employed; the age, body weight, general health, sex and diet of the patient; the time of administration; the route of administration; the rate of excretion of the specific compound(s) employed; the duration of the treatment; drugs used in combination or coincidental with the specific compound(s) employed and like factors well known in the medical and/or veterinary arts. For example, it is well within the skill of the art to start doses of the compound(s) at levels lower than those required to achieve the desired therapeutic effect and to gradually increase the dosage until the desired effect is achieved. If desired, the effective daily doses may be divided into multiple doses for purposes of administration. Consequently, single dose compositions may contain such amounts or submultiples to make up the daily dose.

Administration of the blood glucose concentration-regulating compound(s) can occur as a single event or over a time course of treatment. For example, one or more of the blood glucose concentration-regulating compounds can be administered daily, weekly, bi-weekly, or monthly. For treatment of acute conditions, the time course of treatment may be at least several hours or days. Certain conditions could extend treatment from several days to several weeks. For example, treatment could extend over one week, two weeks, or three weeks. For more chronic conditions, treatment could extend from several weeks to several months, a year or more, or the lifetime of the mammal in need of such treatment. Alternatively, the blood glucose concentration-regulating compounds can be administered daily, weekly, bi-weekly, or monthly, for a period of several weeks, months, years, or over the lifetime of the mammal as a prophylactic measure.

Typically, the blood glucose concentration-regulating amount is at least about 10 mg/kg of a compound selected from the group consisting of nicotinamide, nicotinamide mononucleotide (NMN), and nicotinamide adenine dinucleotide (NAD); salts, derivatives, or prodrugs thereof; a purified polypeptide useful in NAD biosynthesis; and combinations thereof. For example, the blood glucose concentration-regulating amount may be from about 10 mg/kg to about 2,000 mg/kg; from about 100 mg/kg to about 1,900 mg/kg; from about 200 mg/kg to about 1,800 mg/kg; from about 300 mg/kg to about 1,700 mg/kg; from about 400 mg/kg to about 1,600 mg/kg; or from about 500 mg/kg to about 1,500 mg/kg. By way of another example, the blood glucose concentration-regulating amount may be from about 10 mg/kg to about 1,000 mg/kg; from about 20 mg/kg to about 900 mg/kg; from about 30 mg/kg to about 900 mg/kg; from about 40 mg/kg to about 800 mg/kg; or from about 50 mg/kg to about 500 mg/kg.

Detection of the Blood Glucose Concentration

Typically, the concentration of blood glucose in a mammal can be measured in the whole blood, plasma, serum, or urine of the mammal. Blood glucose concentration and/or increases and decreases thereof can be measured according to various methods known in the art such as, for example, through the use of enzymes such as glucose-oxidase, hexokinase, and glucose dehydrogenase. These enzymes can be dry coated on test strips which, when contacted with a biological sample (e.g., whole blood, plasma, serum, etc.), produce a color change correlating to blood glucose concentration. Alternatively, electrical current or light reflection of the sample on the test strip can be conducted and displayed in various "glucose meter" devices, such as an Accu-Chek II glucometer (commercially available from Roche Diagnostics). Other glucose meters include minimally invasive or non-invasive glucose meters which rely on near-infrared spectroscopy to measure blood glucose concentration. These and other suitable methods can be employed prior to, during, and/or after the administration of the blood glucose concentration-regulating compound. Typically, the blood glucose concentration is measured at least before and after administration of the blood glucose concentration-regulating compound to a mammal, so as to detect, e.g., an increase, decrease, and/or maintenance in or of the concentration of blood glucose in the mammal as compared to a previously determined level.

The regulation of blood glucose concentration is typically detectable following the administration of the blood glucose concentration-regulating compound(s). The rapidity of detection, however, generally depends on the condition, illness, or disease being treated (or prevented) by administration of the blood glucose concentration-regulating compound(s). For more acute conditions, for example, the regulation of blood glucose concentration may be detectable by at least about 5 minutes after the administration of the compound, by at least about 15 minutes after the administration of the compound, or longer. In some embodiments, the regulation of blood glucose concentration is detectable from about 5 minutes to about 2 hours after the administration of the compound; most preferably in these embodiments from about 15 minutes to about 2 hours. For more intermediate stage or chronic conditions, or for preventative measures, detection of the regulation of blood glucose concentration may be more difficult to determine, since the regulation may be incremental over a longer period of time. The regulation of blood glucose concentration may be detected using the various methods described in detail above.

Routes of Administration, Formulations/Pharmaceutical Compositions

Blood glucose concentration-regulating compounds useful in the present invention may be dispersed in a pharmaceutically acceptable carrier prior to administration to the mammal. The carrier, also known in the art as an excipient, vehicle, auxiliary, adjuvant, or diluent, is typically a substance which is pharmaceutically inert, confers a suitable consistency or form to the composition, and does not diminish the efficacy of the blood glucose concentration-regulating compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the blood glucose concentration-regulating compounds of the present invention can be formulated for any route of administration so long as the blood circulation system is available via that route. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the blood glucose concentration-regulating compounds of the present invention are well known to those of ordinary skill in the art and are selected based upon a number of factors: the particular compound used, and its concentration, stability and intended bioavailability; the subject, its age, size and general condition; and the route of administration. Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly (oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in *The Chemotherapy Source Book* (Williams & Wilkens Publishing), *The Handbook of Pharmaceutical Excipients*, (American Pharmaceutical Association, Washington, D.C., and The Pharmaceutical Society of Great Britain, London, England, 1968), *Modern Pharmaceutics*, (G. Banker et al., eds., 3d ed.)(Marcel Dekker, Inc., New York, N.Y., 1995), *The Pharmacological Basis of Therapeutics*, (Goodman & Gilman, McGraw Hill Publishing), *Pharmaceutical Dosage Forms*, (H. Lieberman et al., eds.)(Marcel Dekker, Inc., New York, N.Y., 1980), *Remington's Pharmaceutical Sciences* (A. Gennaro, ed., 19th ed.)(Mack Publishing, Easton, Pa., 1995), *The United States Pharmacopeia* 24, *The National Formulary* 19, (National Publishing, Philadelphia, Pa., 2000), A. J. Spiegel et al., and Use of Nonaqueous Solvents in Parenteral Products, JOURNAL OF PHARMACEUTICAL SCIENCES, Vol. 52, No. 10, pp. 917-927 (1963).

Increasing Blood Glucose Concentration

One specific aspect of the present invention is a process for increasing the concentration of blood glucose in a mammal. Surprisingly, it has been discovered that the concentration of blood glucose in a mammal may be increased by administering to the mammal a blood glucose concentration-increasing amount of a compound selected from nicotinamide; salts, derivatives, or prodrugs of nicotinamide; and combinations thereof. Suitable dosages and time course of treatment, methods of detecting the blood glucose concentration increase, and routes of administration and formulations and pharmaceutical compositions are also described in detail above. Exemplary blood glucose concentrations and percent increases thereof are described above.

Conditions, illnesses, and diseases that may be treated and/or prevented according to this aspect of the present invention are described above or will be apparent to medical professionals or others skilled in the art.

Preferably, the blood glucose concentration-increasing amount is at least about 10 mg/kg of a compound selected from the group consisting of nicotinamide; salts, derivatives, or prodrugs of nicotinamide; and combinations thereof. For example, the blood glucose concentration-increasing amount may be from about 10 mg/kg to about 2,000 mg/kg; from about 100 mg/kg to about 1,900 mg/kg; from about 200 mg/kg to about 1,800 mg/kg; from about 300 mg/kg to about 1,700 mg/kg; from about 400 mg/kg to about 1,600 mg/kg; or from about 500 mg/kg to about 1,500 mg/kg. By way of another example, the blood glucose concentration-increasing amount may be from about 10 mg/kg to about 1,000 mg/kg; from about 20 mg/kg to about 900 mg/kg; from about 30 mg/kg to about 800 mg/kg; from about 40 mg/kg to about 700 mg/kg; or from about 50 mg/kg to about 500 mg/kg.

The increase in blood glucose concentration is typically detectable following the administration of the blood glucose concentration-increasing compound. As noted above, however, the rapidity of detection may depend on the particular condition, illness, or disease being treated (or prevented) by administration of the blood glucose-regulating compound. Typically, the blood glucose concentration increase is detectable by at least about 5 minutes after the administration of the compound. For example, the blood glucose concentration increase is detectable by at least about 15 minutes after the administration of the compound. In various embodiments, the blood glucose concentration increase is detectable from about 5 minutes to about 2 hours after the administration of the compound; for example, from about 15 minutes to about 2 hours. The increase in blood glucose concentration may be detected using the various methods described in detail above.

Decreasing Blood Glucose Concentration

Another specific aspect of the present invention is a process for decreasing the concentration of blood glucose in a mammal. Surprisingly, it has been discovered that the concentration of blood glucose in a mammal may be decreased by administering to the mammal a blood glucose concentration-decreasing amount of a compound selected from nicotinamide mononucleotide (NMN); salts, derivatives, or prodrugs of NMN; and combinations thereof. Suitable doses and time course of treatment, methods of detecting the blood glucose concentration decrease, and routes of administration and formulations and pharmaceutical compositions are described in detail above.

Among a variety of conditions that may be treated and/or prevented by a blood glucose concentration-decreasing amount of nicotinamide mononucleotide (NMN) and salts, derivatives, prodrugs, and combinations thereof, are impaired glucose tolerance (IGT) and impaired fasting glucose (IFG). Impaired glucose tolerance may be clinically diagnosed where the patient has two-hour glucose levels of 140 to 199 mg/dL (7.8 to 11.0 mmol/L) using a glucose tolerance test such as the 75 g oral glucose tolerance test. Impaired fasting glucose may be clinically diagnosed where the patient has a fasting glucose level of 100 to 125 mg/dL (5.6 to 6.9 mmol/L) using similar tests. These blood glucose concentration ranges are above normal but below the level that is diagnostic for diabetes. Patients with impaired glucose tolerance or impaired fasting glucose, however, have a significant risk of developing diabetes and thus can be a target group for primary prevention. Diabetes itself may also be treated and/or prevented by a blood glucose concentration-decreasing amount of nicotinamide mononucleotide (NMN) and salts, derivatives, and prodrugs thereof. Diabetes may be diagnosed where the patient has two-hour glucose levels of above 200 mg/dL or a fasting glucose level of above 126 mg/dL. Other conditions, illnesses, and diseases that may be treated and/or prevented according to this aspect of the present invention are described above or will be apparent to medical professionals or other skilled in the art.

Preferably, the blood glucose concentration-decreasing amount is at least 10 mg/kg of a compound selected from the group consisting of nicotinamide mononucleotide (NMN); salts, derivatives, or prodrugs of NMN; and combinations thereof. For example, the blood glucose concentration-decreasing amount may be from about 10 mg/kg to about 2,000 mg/kg; from about 100 mg/kg to about 1,900 mg/kg; from about 200 mg/kg to about 1,800 mg/kg; from about 300 mg/kg to about 1,700 mg/kg; from about 400 mg/kg to about 1,600 mg/kg; or from about 500 mg/kg to about 1,500 mg/kg. By way of another example, the blood glucose concentration-decreasing amount may be from about 10 mg/kg to about 1,000 mg/kg; from about 20 mg/kg to about 900 mg/kg; from about 30 mg/kg to about 800 mg/kg; from about 40 mg/kg to about 700 mg/kg; or from about 50 mg/kg to about 500 mg/kg.

The decrease in blood glucose concentration is typically detectable following the administration of the blood glucose concentration-decreasing compound. As noted above, however, the rapidity of detection may depend on the particular condition, illness, or disease being treated (or prevented) by administration of the blood glucose-regulating compound. Typically, the blood glucose concentration decrease is detectable by at least about 5 minutes after the administration of the compound. For example, the blood glucose concentration decrease is detectable by at least about 15 minutes after the administration of the compound. In various embodiments, the blood glucose concentration decrease is detectable from about 5 minutes to about 2 hours after the administration of the compound; for example, from about 15 minutes to about 2 hours. The decrease in blood glucose concentration may be detected using the various methods described in detail above.

Polypeptide for Use in NAD Biosynthesis and Processes for Producing the Same

Another aspect of the present invention is a purified polypeptide. The polypeptide of the present invention is preferably an isolated polypeptide; that is, separated from its natural source. For example, if the isolated polypeptide is derived from its natural source, the isolated polypeptide has been removed or separated from its natural environment and at least partially purified from other nucleic acids, polypeptides, and other materials.

The purified polypeptide of the present invention may be a polypeptide having a sequence with at least about 65% homology to SEQ ID NO: 1. The sequence represents a polypeptide useful in nicotinamide adenine dinucleotide (NAD) biosynthesis. In a particular embodiment, the polypeptide corresponds to an extracellular version of Nampt.

The purified polypeptide of the present invention may also be a polypeptide having a sequence with at least about 65% homology to SEQ ID NO: 7. The sequence represents a polypeptide useful in nicotinamide adenine dinucleotide (NAD) biosynthesis fused to the affinity tag FLAG® (Sigma-Aldrich, Co., St. Louis, Mo.). In a particular embodiment, the polypeptide corresponds to an extracellular version of Nampt fused to the affinity tag FLAG®.

As used herein, "percent homology" of two amino acid sequences or of two nucleic acids is determined using the algorithm of Karlin and Altschul (Proc. Natl. Acad. Sci. USA, (1990) 87, 2264-2268), modified as in Karlin and Altschul (Proc. Natl. Acad. Sci. USA, (1993) 90, 5873-5877). Such an algorithm is incorporated into NBLAST and XBLAST programs of Altschul et al. (J. Mol. Biol. 215:403-410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (Nucleic Acids Res., (1997) 25, 3389-3402). When utilizing BLAST and Gapped BLAST programs, the default parameters of the respective programs (e.g., XBLAST and NBLAST) are used. See, for example, www.ncbi.nlm.nih.gov.

Within the scope of the present invention is polypeptide analogs of the invention arrived at by amino acid substitutions based on the relative similarity of the amino acid side-chain substituents, for example, their hydrophobicity, hydrophilicity, charge, size, etc. One factor that can be considered in making amino acid substitutions is the hydropathic index of amino acids. The importance of the hydropathic amino acid index in conferring interactive biological function on a protein has been discussed by Kyte and Doolittle (J. Mol. Biol., 157: 105-132, 1982). It is accepted that the relative hydropathic character of amino acids contributes to the secondary structure of the resultant protein. This, in turn, affects the interaction of the protein with molecules such as enzymes, substrates, receptors, DNA, antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydropathic indices within ±2 are preferably substituted for one another, those within ±1 are more preferred, and those within ±0.5 are most preferred.

Furthermore, amino acid substitutions in the peptides of the present invention can be based on factors other than hydrophobicity, such as size, side chain substituents, charge, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine. It should be noted that changes which are not expected to be advantageous can also be useful if these result in the production of functional sequences.

Although the polypeptide may have a polypeptide sequence with at least about 65% homology to SEQ ID NO: 1, in certain embodiments the purified polypeptide has at least about 70% homology to SEQ ID NO: 1. In a particular embodiment, the purified polypeptide has at least about 75% homology to SEQ ID NO: 1; in this embodiment, the purified polypeptide may have, for example, at least about 80%, at least about 85%, at least about 90%, at least about 95%, at least about 97%, or at least about 99% homology to SEQ ID NO: 1.

Although the polypeptide may also have a polypeptide sequence with at least about 65% homology to SEQ ID NO: 7, in certain embodiments the purified polypeptide has at least about 70% homology to SEQ ID NO: 7. In a particular embodiment, the purified polypeptide has at least about 75% homology to SEQ ID NO: 7; in this embodiment, the purified polypeptide may have, for example, at least about 80%, at least about 85%, at least about 90%, at least about 95%, at least about 97%, or at least about 99% homology to SEQ ID NO: 7.

Accordingly, one embodiment of the invention comprises a Nampt polypeptide, wherein the Nampt polypeptide has a polypeptide sequence selected from the group consisting of SEQ ID NO: 1; SEQ ID NO: 7; a polypeptide capable of catalyzing the conversion of nicotinamide to nicotinamide mononucleotide (NMN), an amino acid sequence of the polypeptide comprising the amino acid sequence of SEQ ID NO: 1; a polypeptide capable of catalyzing the conversion of nicotinamide to nicotinamide mononucleotide (NMN), an amino acid sequence of the polypeptide comprising the amino acid sequence of SEQ ID NO: 7; a polypeptide capable of catalyzing the conversion of nicotinamide to nicotinamide mononucleotide (NMN), the polypeptide having an amino acid sequence with at least about 65% homology to SEQ ID NO: 1 and conservative amino acid substitutions; and a polypeptide capable of catalyzing the conversion of nicotinamide to nicotinamide mononucleotide (NMN), the polypeptide having an amino acid sequence with at least about 65% homology to SEQ ID NO: 7 and conservative amino acid substitutions. In a particularly preferred embodiment, the Nampt polypeptide has a polypeptide sequence corresponding to SEQ ID NO: 7.

Another aspect of the present invention is a polynucleotide encoding a purified polypeptide. Typically, the polynucleotide encodes a purified polypeptide having at least about 70% homology to SEQ ID NO: 1. Although the polynucleotide can encode a purified polypeptide having at least about 70% homology to SEQ ID NO: 1, in certain embodiments the polynucleotide encodes a purified polypeptide having at least about 75% homology to SEQ ID NO: 1. In a particular embodiment, the polynucleotide encodes a purified polypeptide having at least about 80% homology to SEQ ID NO: 1; in this embodiment, the polynucleotide may encode a purified polypeptide having at least about 85%, at least about 90%, at least about 95%, at least about 97%, or at least about 99% homology to SEQ ID NO: 1.

Exemplary of a polynucleotide encoding a purified polypeptide having a sequence represented by SEQ ID NO: 1, or encoding a polypeptide having at least about 65%, at least about 70%, at least about 75%, at least about 80%, at least about 85%, at least about 90%, at least about 95%, at least about 97%, or at least about 99% homology to SEQ ID NO: 1 is the polynucleotide sequence represented by SEQ ID NO: 18. Additional exemplary polynucleotide sequences include polynucleotide sequences encoding a polypeptide having at least about 65%, at least about 70%, at least about 75%, at least about 80%, at least about 85%, at least about 90%, at least about 95%, at least about 97%, or at least about 99% homology to SEQ ID NO: 1 and hybridizing to SEQ ID NO: 18 under stringent conditions. Generally, stringent conditions for hybridization and washing are those under which nucleotide sequences at least about 60% homologous to each other typically remain hybridized to each other. Preferably, the conditions are such that sequences at least about 65%, more preferably at least about 70%, even more preferably at least about 75%, still more preferably at least about 80%, yet even more preferably at least about 85%, still more preferably at least about 90%, even more preferably at least about 95%, even more preferably at least about 97%, and most preferably at least about 99% homologous to each other typically remain hybridized to each other. Such stringent conditions are known to those skilled in the art and can be found in Current Protocols in Molecular Biology, 6.3.1-6.3.6, John Wiley & Sons, N.Y. (1989). A preferred, non-limiting example of stringent hybridization conditions are hybridization in 6×SSC at about 45° C., followed by one or more washes in 0.2×SSC, 0.1% SDS at 50° C.-65° C. Examples of moderate to high stringency conditions include, for example, initial hybridization in 6×SSC, 5× Denhardt's solution, 100 g/ml fish sperm DNA, 0.1% SDS, at 55° C. for sufficient time to permit hybridization (e.g., several hours to overnight), followed by washing two times for 15 min each in 2×SSC, 0.1% SDS, at room temperature, and two times for 15 min each in 0.5-1×SSC, 0.1% SDS, at 55° C., followed by autoradiography. Typically, the nucleic acid molecule is capable of hybridizing when the hybridization mixture is washed at least one time in 0.1×SSC at 50 C, preferably at 55° C., more preferably at 60° C., and still more preferably at 65° C. Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Another aspect of the present invention is a polynucleotide encoding a purified polypeptide. Typically, the polynucleotide encodes a purified polypeptide having at least about 70% homology to SEQ ID NO: 7. Although the polynucleotide can encode a purified polypeptide having at least about 70% homology to SEQ ID NO: 7, in certain embodiments the polynucleotide encodes a purified polypeptide having at least about 75% homology to SEQ ID NO: 7. In a particular embodiment, the polynucleotide encodes a purified polypeptide having at least about 80% homology to SEQ ID NO: 7; in this embodiment, the polynucleotide may encode a purified polypeptide having at least about 85%, at least about 90%, at least about 95%, at least about 97%, or at least about 99% homology to SEQ ID NO: 7.

Exemplary of a polynucleotide encoding a purified polypeptide having a sequence represented by SEQ ID NO: 7, or encoding a polypeptide having at least about 65%, at least about 70%, at least about 75%, at least about 80%, at least about 85%, at least about 90%, at least about 95%, at least about 97%, or at least about 99% homology to SEQ ID NO: 7 is the polynucleotide sequence represented by SEQ ID NO: 19. Additional exemplary polynucleotide sequences include polynucleotide sequences encoding a polypeptide having at least about 65%, at least about 70%, at least about 75%, at least about 80%, at least about 85%, at least about 90%, at least about 95%, at least about 97%, or at least about 99% homology to SEQ ID NO: 7 and hybridizing to SEQ ID NO: 19 under stringent conditions. Generally, stringent conditions for hybridization and washing are those under which nucleotide sequences at least about 60% homologous to each other typically remain hybridized to each other. Preferably, the conditions are such that sequences at least about 65%, more preferably at least about 70%, even more preferably at least about 75%, still more preferably at least about 80%, yet even more preferably at least about 85%, still more preferably at least about 90%, even more preferably at least about 95%, even more preferably at least about 97%, and most preferably at least about 99% homologous to each other typically remain hybridized to each other. Such stringent conditions are discussed above. Accordingly, another aspect of the invention is a isolated or purified nucleotide sequence encoding a polypeptide capable of catalyzing the conversion of nicotinamide to nicotinamide mononucleotide (NMN), wherein the nucleotide sequence is SEQ ID NO: 19 or a nucleotide sequence hybridizing to SEQ ID NO: 19 under stringent conditions as described above. The nucleotide sequence may encode a polypeptide having at least about 65%, least about 70%, least about 75%, least about 80%, least about 85%, least about 90%, least about 95%, least about 97%, or least about 99% of the catalyzing activity of Nampt, preferably an intracellular version of Nampt, more preferably an extracellular or secreted version of Nampt, and in a particular embodiment, the Nampt polypeptide as described above.

As noted above, in some embodiments the purified polypeptide corresponds to a polypeptide useful in NAD biosynthesis; more preferably in these embodiments the polypeptide corresponds to an extracellular version of Nampt. In other embodiments, the purified polypeptide corresponds to a fusion protein comprising an extracellular version of Nampt and an affinity tag (e.g., for identification and/or purification). As an extracellular polypeptide, the polypeptide has a natural source outside of a cell membrane. This is in contrast to intracellular polypeptides or, in particular, intracellular versions of Nampt, which may be found within tissues and cell membranes. Although the polypeptide of the present invention is an extracellular polypeptide, it may originate from an intracellular region and be secreted or otherwise delivered or transported from an intracellular region to an extracellular region, such as cell culture medium or blood plasma, described in further detail below. However, it will be understood by one of skill in the art that the purified polypeptide of the present invention refers only to the extracellular version. As discussed above, Nampt catalyzes the conversion of nicotinamide to NMN in the NAD biosynthesis pathway. Accordingly, the purified polypeptide of the present invention catalyzes the conversion of nicotinamide to NMN in an extracellular compartment of NAD biosynthesis.

The purified polypeptide of the present invention also has an apparent molecular weight of from about 56 kD to about 57 kD. Surprisingly, it has been discovered that the polypeptide of the present invention has a higher apparent molecular weight (see FIG. 6A) than the intracellular version of Nampt reported by, e.g., Fukuhara et al., Science, (2005) 307, 426-430. It is believed that the polypeptide is post-translationally modified in some manner resulting in a larger molecular weight as compared to the intracellular form of Nampt. For example, the post-translational modification may allow the extracellular form of Nampt to be secreted by certain tissues and/or cells. Examples of post-translational modifications that may result in the polypeptide having a larger apparent molecular weight as compared to the intracellular version of Nampt include amino acid modifications such as acetylation, phosphorylation, methylation, carboxylation, hydroxylation, glycosylation, nucleotidylation, iodination, lipid addition, and the like. As is well known in the art, such modification(s) may cause the polypeptide to migrate more slowly during electrophoresis of the polypeptide on a gel, resulting in the appearance of a relatively larger molecular weight (i.e., apparent molecular weight) than the actual molecular weight of the polypeptide.

Figure 5A:
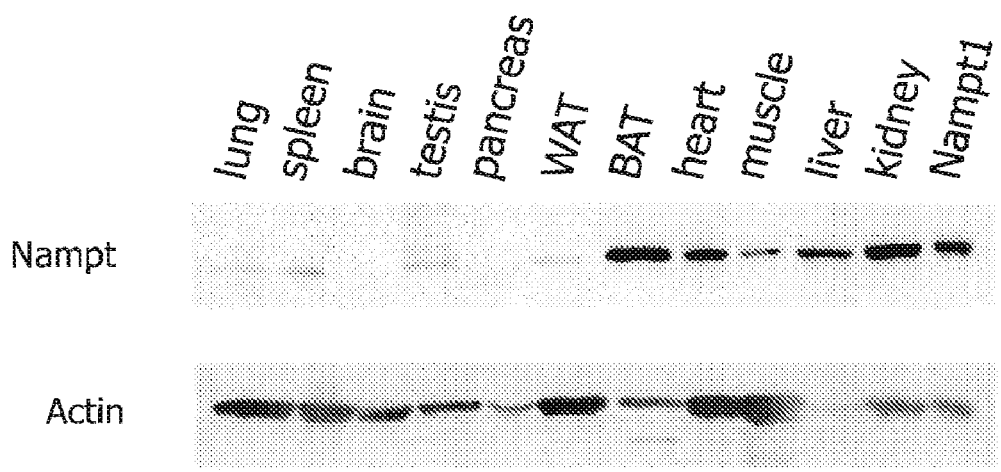
FIGS. 5A, 5B, and 5C are an image of a gel showing the tissue distribution of Nampt, an image of a gel showing the fasting-induced increase of Nampt in brown adipose tissue, and a bar graph depicting the quantitation of the fasting-induced increase of Nampt in brown adipose tissue, respectively.

As illustrated in FIG. 5A, the intracellular version of Nampt is relatively highly expressed in brown adipose tissue, liver, and kidney tissues, and intermediately expressed in heart tissue. White adipose tissue, lung, spleen, testis, and muscle tissues, on the other hand, expressed relatively low levels of the intracellular version of Nampt (see FIG. 5A). These findings suggest that the rate of NAD biosynthesis from nicotinamide is significantly varied in different tissues. The inventors have also discovered that the levels of the intracellular version of Nampt increased in the brown adipose tissue in fasted mice as compared to fed mice, suggesting that Nampt-mediated NAD biosynthesis might be regulated by nutrient activity in brown adipose tissue.

The polypeptide useful in NAD biosynthesis may be produced endogenously from certain cell lines. Among the cell lines capable of producing the polypeptides are adipose cells; typically, the adipose cells are preadipose cells capable of differentiating into adipose cells. It has been discovered that brown preadipose cells are particularly effective in producing the polypeptide corresponding to the extracellular version of Nampt in relatively large amounts, typically during differentiation. One example of a suitable brown preadipose cell line is the cell line termed HIB-1B. White adipose cells (such as the cell line termed 3T3-L1) can also produce the extracellular version of Nampt, though typically in lesser quantities.

The polypeptide may be produced by culturing preadipose cells in a culture medium and purifying the polypeptide. The preadipose cells are typically cultured in a culture medium in such a manner as to allow the preadipose cells to differentiate into adipose cells. Generally, the culture medium includes such cell culture reagents as serum (e.g., fetal bovine serum (FBS)), dexamethasone, 3-isobutyl-1-methylxanthine (IBMX), 3,3',5'-triiodo-L-thyronine (T3), insulin, and the like. Suitable methods and media for maintaining cells in culture are known to those of skill in the art. In one particular embodiment, the culture medium does not contain serum. As discussed above, it is believed that differentiated adipose cells produce (e.g., by secretion to an extracellular domain) a post-translationally modified version of Nampt, typically during differentiation. Without being bound to a single theory, it is further believed that, in some instances, that modification may be labile in culture media containing serum.

Differentiation of the preadipose cells into adipose cells typically involves changes in size, shape, and cellular properties. For example, one characteristic of mature adipose cells is their relatively high fat content. The various compounds present in the culture medium (such as those described above) activate various signaling pathways and transcription factors that induce differentiation.

The differentiated adipose cells (and particularly brown adipose cells) secrete or otherwise deliver or transport the polypeptide into the culture medium. Hence, the polypeptide is an extracellular polypeptide and, more specifically, the polypeptide corresponds to the extracellular version of Nampt. The polypeptide may then be purified from the culture medium (e.g., from the culture supernatant) using methods known to those of skill in the art.

In another aspect of the present invention, the polypeptide of the present invention may be purified from the plasma, serum, or whole blood of a mammal, or combinations thereof.

The polypeptide may also be produced or obtained through the introduction of exogenous nucleic acids encoding the polypeptide into target cells in order to cause the production of the polypeptide in cells that would otherwise not produce the polypeptide or to increase the production of the polypeptide in cells that may produce the polypeptide endogenously.

Generally, the creation of host cells is achieved by the introduction of exogenous or additional endogenous nucleic acid sequences into the host cells, typically via expression vectors (sometimes also referred to herein as transformation vectors). An expression vector is generally a replicable nucleic acid construct used to express a nucleic acid which encodes the desired protein and which includes a transcriptional unit. The expression vector described herein is an expression vector that contains an isolated nucleic acid encoding a fusion protein comprising the polypeptide of the present invention. Generally, the fusion protein will also comprise an affinity tag for identification and purification of the polypeptide of the present invention once it is produced by the host cell containing the vector.

Typically, the expression vector will contain a nucleic acid sequence encoding the fusion peptide operably linked to an expression control sequence. The transcriptional unit can comprise an assembly of (1) genetic element(s) having a regulatory role in gene expression, for example, promoters, operators, or enhancers, operatively linked to (2) a nucleic acid sequence, typically DNA, encoding a desired protein which is transcribed into mRNA and translated into protein, and (3) appropriate transcription and translation initiation and termination sequences. The choice of promoter and other regulatory elements generally varies according to the intended host cell. In the expression vectors, regulatory elements controlling transcription or translation can be generally derived from mammalian, microbial, viral, or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed. In general, expression vectors of utility in recombinant DNA techniques are often in the form of "plasmids" which refer to circular double stranded DNA loops which, in their vector form are not bound to the chromosome. "Plasmid" and "vector" may be used interchangeably as the plasmid is the most commonly used form of vectors. However, the term is intended to include such other forms of expression vectors which serve equivalent functions and which become known in the art subsequently hereto. A wide variety of vectors, into which nucleic acids encoding polypeptides of the invention can be inserted, are readily available from commercial sources. Examples include pSPORT vectors, pGEM vectors (Promega), pPROEX vectors (LTI, Bethesda, Md.), Bluescript vectors (Stratagene), pET vectors (Novagen), and pQE and pCXN vectors (Qiagen).

Therefore, an expression vector, and in particular a mammalian expression vector, capable of introducing nucleic acids involved in the production of the polypeptide of the present invention are easily designed and generally contain one or more nucleic acid sequences coding for a Nampt protein under the transcriptional control of 5' and 3' regulatory sequences. Such vectors generally comprise, operatively linked in sequence in the 5' to 3' direction, a promoter sequence that directs the transcription of a downstream heterologous structural nucleic acid in the cell; optionally, a 5' non-translated leader sequence; optionally a signal sequence; a nucleotide sequence that encodes a polypeptide of the present invention and optionally an affinity tag; and optionally a 3' non-translated region that encodes a polyadenylation signal which functions in cells to cause the termination of transcription and the addition of polyadenylate nucleotides to the 3' end of the mRNA encoding the protein. Vectors encoding proteins that are not secreted may lack the signal sequence. The vectors may also contain a selectable marker.

Typical 5'-3' regulatory sequences include a transcription initiation start site, a ribosome binding site, an RNA processing signal, a transcription termination site, and/or a polyadenylation signal. Thus, the recombinant expression vectors include one or more regulatory sequences, selected on the basis of the host cells to be used for expression, operably linked to the nucleic acid sequence to be expressed. It will be appreciated by those skilled in the art that the design of the expression vector can depend on such factors as the choice of the host cell to be transformed, the level of expression of protein desired, etc.

Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding the antigenic domain containing fusion protein or can be introduced on a separate vector. Cells stably transfected with the introduced nucleic acid can be identified by drug selection (e.g., cells that have incorporated the selectable marker gene will survive, while the other cells die). Methods and materials for preparing recombinant vectors, transforming host cells using replicating vectors, and expressing biologically active foreign polypeptides and proteins are generally well known and are described in Sambrook, et al., Molecular Cloning: a Laboratory Manual, 3rd ed (2001) Cold Spring Harbor Press.

As discussed above, prokaryotic or eukaryotic expression vector systems may be used. Eukaryotic expression systems are preferred. Non-limiting examples of suitable eukaryotic expression systems include yeast expression vectors (described by Brake, A. et al., Proc. Nat. Acad. Sci. USA, (1984) 81, 4642-4646), Polyoma virus based expression vectors (described in Kern, F. G. et al. Gene, (1986) 43, 237-245) Simian virus 40 (SV40)-based expression vectors in COS-1 Simian cells (as described in Gething, M. J. et al. Nature, (1981) 293, 620-625) and baculovirus (insect)-based expression vectors (described in U.S. Pat. No. 4,145,051, issued May 17, 1988, and U.S. Pat. No. 4,879,232, issued Nov. 7, 1989). An example of a prokaryotic expression system (e.g., *E. coli*) is presented below in Example 1. Particularly preferred expression vectors include *E. coli*, simian COS cells and baculovirus (insect) cells.

Cultured cells can be transformed with the nucleic acids and/or vectors containing nucleic acids as described above. Progeny of such transformed cells are also included in various embodiments. In general, the host cell may comprise any cellular organism including a prokaryotic cell or eukaryotic cell that is capable of being transformed with a vector comprising the isolated nucleic acids encoding the polypeptides described above. Examples of such cells include, for example, bacterial cells, yeast cells, plant cells, and mammalian cells. Generally, mammalian cells are preferred. Examples of suitable host cells include, for example, *E. coli* cells, *S. cerevisiae* cells, Chinese hamster ovary (CHO) cells, HeLa cells, U2OS cells, Vero cells, NIH-3T3 cells, LM(tk-) cells, and adipose cells, such as for example, white adipose cells such as 3T3-L1 cells and brown adipose cells such as HIB-1B cells.

The techniques of transforming and transfecting cells are well known in the art and may be found in such general references as Sambrook and Russel, Molecular Cloning: A laboratory Manual, 3d Ed. (2001) Cold Spring Harbor Laboratory Press, NY.

The vectors described above can be transformed into and expressed in many host cells. Transformed host cells may be cultured in conventional nutrient media modified as appropriate for inducing promoters, selecting transformants, or amplifying genes. The culture conditions, such as temperature, pH, and the like, will be apparent to the ordinarily skilled artisan.

The cultured cells can be transformed with an expression vector encoding the polypeptide of the present invention. Generally, however, the expression vector will encode the polypeptide of the present invention and an affinity tag for purification and isolation of the polypeptide that has been secreted into the cell culture medium (extracellular) or that has been released from lysed cells (intracellular). The expression vector may be as described above. Examples of vector construction, cell culture, and transformation are provided in Examples 13 and 14.

The cultured cell may also contain a reporter gene linked to at least one nucleic acid sequence encoding the polypeptide of the present invention. An example of a suitable reporter gene is a luminescent reporter gene, such as a luciferase. In one embodiment, the reporter gene is linked to an expression control sequence.

Accordingly, one aspect of the invention is an expression vector containing a nucleic acid sequence encoding a Nampt polypeptide. In a particular embodiment, the expression vector comprises a nucleotide sequence encoding SEQ ID NO: 1; a nucleotide sequence encoding SEQ ID NO: 7; a nucleotide sequence encoding a polypeptide capable of catalyzing the conversion of nicotinamide to nicotinamide mononucleotide (NMN), an amino acid sequence of the polypeptide comprising the amino acid sequence of SEQ ID NO: 1; a nucleotide sequence encoding a polypeptide capable of catalyzing the conversion of nicotinamide to nicotinamide mononucleotide (NMN), an amino acid sequence of the polypeptide comprising the amino acid sequence of SEQ ID NO: 7; a nucleotide sequence encoding a polypeptide capable of catalyzing the conversion of nicotinamide to nicotinamide mononucleotide (NMN), the polypeptide having an amino acid sequence with at least about 65% identity to SEQ ID NO: 1 and conservative amino acid substitutions; and a nucleotide sequence encoding a polypeptide capable of catalyzing the conversion of nicotinamide to nicotinamide mononucleotide (NMN), the polypeptide having an amino acid sequence with at least about 65% identity to SEQ ID NO: 7 and conservative amino acid substitutions.

Another aspect of the invention is a recombinant or transformed host cell. The host cell comprises a nucleic acid encoding a polypeptide useful in NAD biosynthesis and, in particular, Nampt. In one embodiment, the nucleic acid encodes an intracellular version of the Nampt protein. In another embodiment, the nucleic acid encodes an extracellular version of the Nampt protein. In a particular embodiment of the invention, the nucleic acid encodes SEQ ID NO: 1; SEQ ID NO: 7; a polypeptide capable of catalyzing the conversion of nicotinamide to nicotinamide mononucleotide (NMN), the an amino acid sequence of the polypeptide comprising the amino acid sequence of SEQ ID NO: 1; a polypeptide capable of catalyzing the conversion of nicotinamide to nicotinamide mononucleotide (NMN), the an amino acid sequence of the polypeptide comprising the amino acid sequence of SEQ ID NO: 7; a polypeptide capable of catalyzing the conversion of nicotinamide to nicotinamide mononucleotide (NMN), the polypeptide having an amino acid sequence with at least about 65% homology to SEQ ID NO: 1 and conservative amino acid substitutions; or a polypeptide capable of catalyzing the conversion of nicotinamide to nicotinamide mononucleotide (NMN), the polypeptide having an amino acid sequence with at least about 65% homology to SEQ ID NO: 7 and conservative amino acid substitutions. Preferably, the nucleic acid encoding the Nampt protein is a nucleic acid encoding a Nampt protein and an affinity tag allowing for isolation or purification of the fusion protein. While the affinity tag may be any of a number of affinity tags, such as for example a GST tag, a His tag, a FLAG® tag, or an XPRESS™ tag, the affinity tag preferably comprises one or more copies of the FLAG® octapeptide (DYKDDDDK) (SEQ ID NO: 16) or the XPRESS™ octapeptide (DLYDDDDK) (SEQ ID NO: 17). While the host cell may be any of a number of cells, the recombinant host cell is preferably a mammalian cell, such as for instance a CHO cell, a 3T3-L1 cell, or a HIB-1B cell, more preferably adipose cells, still more preferably a 3T3-L1 cell or a HIB-1B cell, and in a most preferred embodiment, a HIB-1B cell.

Various techniques suitable for use in chemical, biomolecular, biological recovery, quantification, and/or purification of polypeptides from a variety of sources are well known to those of skill in the art and include, for example, precipitation with ammonium sulfate, polyethylene glycol, antibodies and the like or by heat denaturation, followed by centrifugation; fractionation, chromatographic procedures, including but not limited to, partition chromatography (e.g., paper chromatography, thin-layer chromatography (TLC), gas-liquid chromatography and gel chromatography), gas chromatography, high performance liquid chromatography, hydrophobic interaction chromatography, affinity chromatography (e.g., using bacterial proteins that bind to immunoglobulins and/or antibody-antigen complexes by immuno or non-immuno mechanisms, such as Protein A or Protein G), supercritical flow chromatography, ion exchange, gel filtration, reverse phase, hydroxylapatite, lectin affinity; isoelectric focusing and gel electrophoresis; and immuno-detection methods such as enzyme-linked immunosorbent assay (ELISA) (see, e.g., Sambrook et al. (2001), supra; and Freifelder, Physical Biochemistry, Second Edition, pages 238-246).

Having described the invention in detail, it will be apparent that modifications and variations are possible without departing the scope of the invention defined in the appended claims. Furthermore, it should be appreciated that all examples in the present disclosure are provided as non-limiting examples.

EXAMPLE 1

Production of Recombinant NAMPT and NMNAT Proteins

The NAD biosynthesis system was reconstituted in vitro with His-tagged recombinant enzymes. In mammals, NAD biosynthesis from nicotinamide is catalyzed by two enzymes, Nampt and Nmnat (FIG. 3). Full-length cDNAs of the mouse Nampt and Nmnat genes were isolated from a mouse liver cDNA library by PCR.

Mouse Nampt cDNA was isolated based on a homology search in the mouse EST database to the amino acid sequence of *Haemophilus ducreyi* Nampt (Martin et al., J. Bacteriol., (2001) 183, 1168-1174). Mouse Nmnat, an ortholog to the human NMNAT-1 gene, was previously cloned as a fusion gene from the slow Wallerian degeneration mutant mouse (Mack et al., Nat. Neurosci., (2001) 4, 1199-1206). The coding regions of mouse Nampt and Nmnat cDNAs were amplified from a mouse liver cDNA library (Clontech, CA) by PCR with PfuTurbo polymerase (Stratagene, CA). The following forward and reverse primers containing EcoRI sites were generated: SEQ ID NO: 2, Nampt forward; SEQ ID NO: 3, Nampt reverse; SEQ ID NO: 4, Nmnat forward; and SEQ ID NO: 5, Nmnat reverse. The resulting 1584-bp and 972-bp fragments of Nampt and Nmnat cDNAs, respectively, were digested with EcoRI and cloned into the pBluescript SK- vector. Nampt and Nmnat cDNA fragments were then subcloned into the mammalian expression vector pCXN2 (Niwa et al., Gene, (1991) 108, 193-199).

To create N-terminal His-tagged recombinant proteins of these two enzymes, Nampt and Nmnat cDNA fragments were re-amplified by PCR to create EcoRI and NdeI sites at the 5' ends of each cDNA, respectively. The PCR products were cloned into the pET-28a(+) vectors (EMD Biosciences, CA). To create expression vectors for Nampt and Nmnat proteins fused to GFP at their C-termini, the Nampt and Nmnat cDNA fragments were cloned between EcoRI and BamHI sites of the pEGFP-N1 vector (Clontech) after modifying their stop codons. All Nampt and Nmnat cDNA inserts were sequenced, and those sequences were deposited in the GenBank database as accession numbers AY679720 and AY679721, respectively. All necessary plasmids were prepared using the QIAfilter plasmid midi kit (Qiagen, CA).

To produce the recombinant proteins, BL21(DE3)pLysS cells were transformed with each of His-tagged Nampt and Nmnat plasmids. Transformed BL21 (DE3)pLysS cells were grown overnight at 37° C. in 25 ml of Terrific broth containing 75 µg/ml kanamycin and 37 µg/ml chloramphenicol. Cells were spun down, resuspended in 500 ml of the same media, and grown at 37° C. to an $OD_{600}$ of 0.6. His-tagged recombinant proteins were then induced by 1.5 mM isopropyl-D-thiogalactopyranoside (Sigma, MO). After inducing for 5 h at 37° C., cells were spun down and resuspended in lysis buffer (20 mM Tris-HCl [pH 8.0], 300 mM NaCl, 0.1% Triton X-100) with protease inhibitors (Roche Applied Science, IN) and lysozyme. The lysate was then produced with a French press and cleared at 10,000 g for 30 min. The His-tagged Nampt and Nmnat recombinant proteins were purified with Ni-NTA resin (Qiagen, CA) by washing with lysis buffer and wash buffer (20 mM Tris-HCl [pH 8.0], 300 mM NaCl, 10% glycerol, 0.1% Triton X-100, 40 mM imidazole) and eluting with 150 mM imidazole-containing buffer.

Figure 4A:
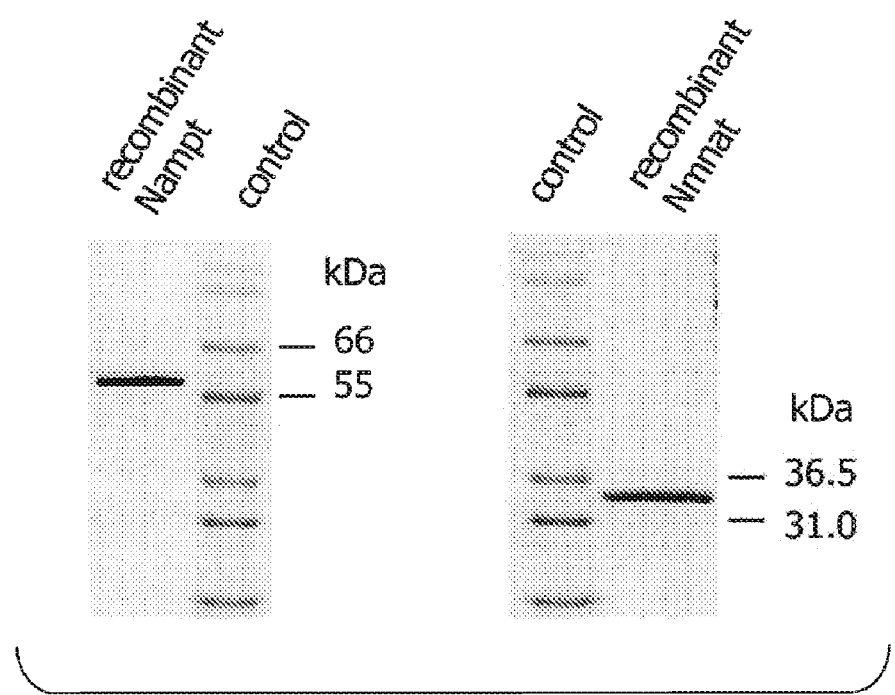
FIGS. 4A, 4B, 4C, and 4D are an image of a gel showing purified recombinant Nampt and Nmnat, a schematic representation of the NAD biosynthesis pathway from nicotinamide, a line and scatter graph depicting NADH as a function of time, and a trace graph of high performance liquid chromatography elution, respectively.

Bacterially produced, His-tagged recombinant mouse Nampt and Nmnat proteins showed molecular weights of approximately 59 and 35 kD, respectively, which are consistent with those predicted from their amino acid sequences (see, e.g., FIG. 4A).

EXAMPLE 2

Biochemical Characterization of NAMPT and NMNAT

Figure 4B:
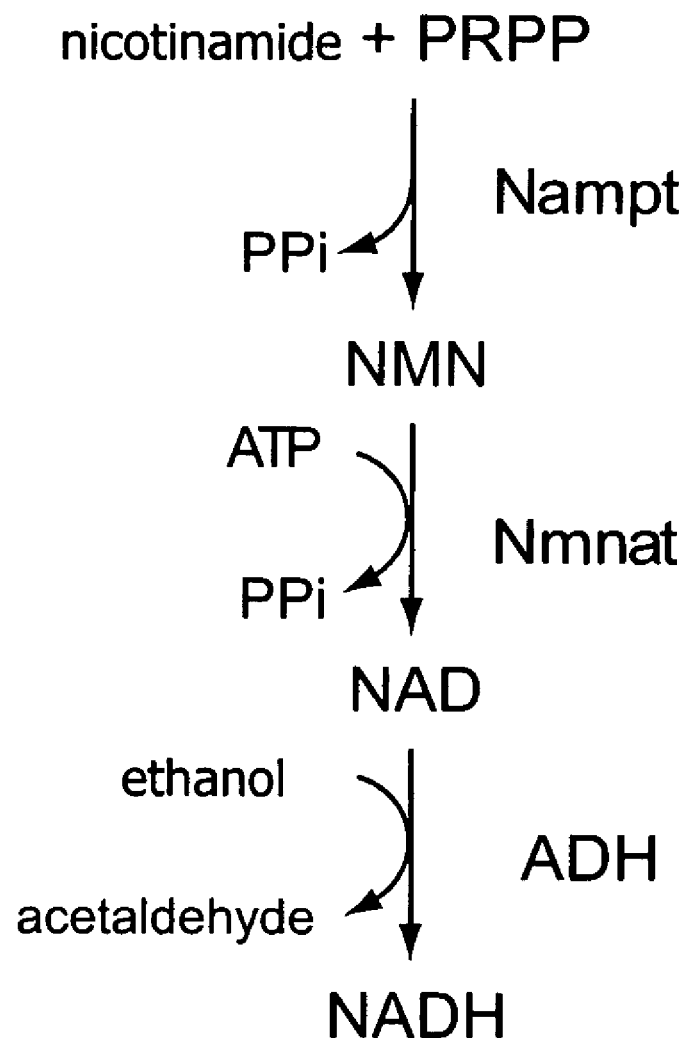
Figure 4C:
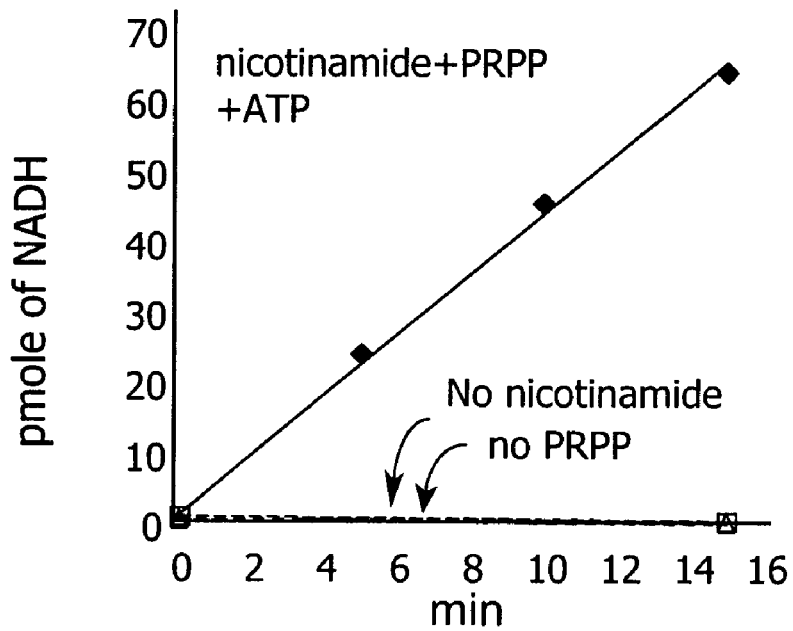
Figure 4D:
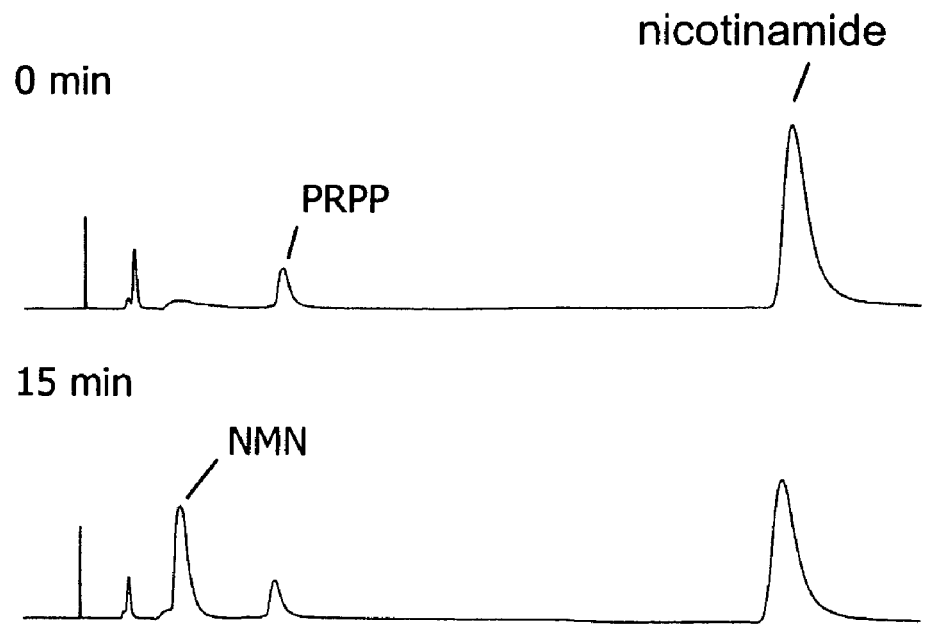

Enzymatic activities of recombinant Nampt and Nmnat proteins were measured by an enzyme-coupled fluorometric assay (see, e.g., FIG. 4B). In this enzyme-coupled reaction, NAD is converted to NADH by alcohol dehydrogenase, and the fluorescence of NADH is detected in a fluorometer. To establish this assay system, optimal reaction conditions for Nmnat were initially examined by varying ATP and $Mg^{2+}$ concentrations and pH of the reaction buffer. The resultant reaction buffer for Nmnat contained 50 mM HEPES [pH 7.4], 0.02% BSA, 12 mM $MgCl_2$, 2 mM ATP, 1.5% ethanol, and 30 µg/ml alcohol dehydrogenase to convert NAD to NADH. To determine the kinetic parameters for Nmnat, 30 ng of purified His-tagged Nmnat and varying concentrations of NMN were added to 1 ml of the reaction buffer. The reactions were run at 37° C. and quenched at six time points by the addition of 250 µl of 0.5 M EDTA. The production of NADH was measured by excitation at 340 nm and emission at 460 nm in a fluorometer. For kinetic characterization of Nampt, 500 ng of His-tagged Nampt and varying concentrations of nicotinamide were reacted at 37° C. in 100 µl of a buffer containing 50 mM Tris-HCl [pH 7.5], 0.02% BSA, 12 mM MgCl$_2$, 2.5 mM ATP, 10 µg/ml His-tagged Nmnat, 0.4 mM phosphoribosyl pyrophosphate (PRPP), 1.5% ethanol, and 30 µg/ml alcohol dehydrogenase. NADH production was measured continuously in a fluorometer.

Results showed that the in vitro-reconstituted NAD biosynthesis reaction generated NAD from nicotinamide, phosphoribosyl pyrophosphate (PRPP) and ATP (see, e.g., FIG. 4C). No NAD was produced in the absence of nicotinamide or PRPP, the substrates of Nampt (see, e.g., FIG. 4C).

Figure 11A:
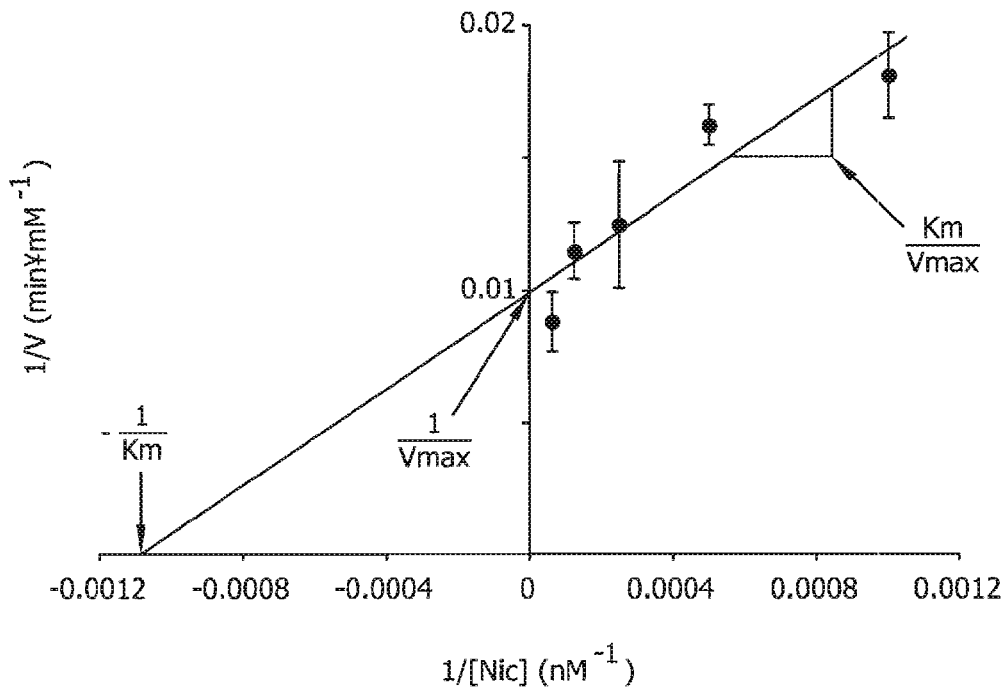
FIGS. 11A and 11B are line and scatter point graphs that depict Lineweaver-Burk plots of mouse Nampt (FIG. 11A) and Nmnat (FIG. 11B). Each data point and their standard deviations were determined by three independent assays (see Example 2). The $K_m$, $V_{max}$, and $k_{cat}$ for each enzyme calculated from these plots are shown in Table 1.
Figure 11B:
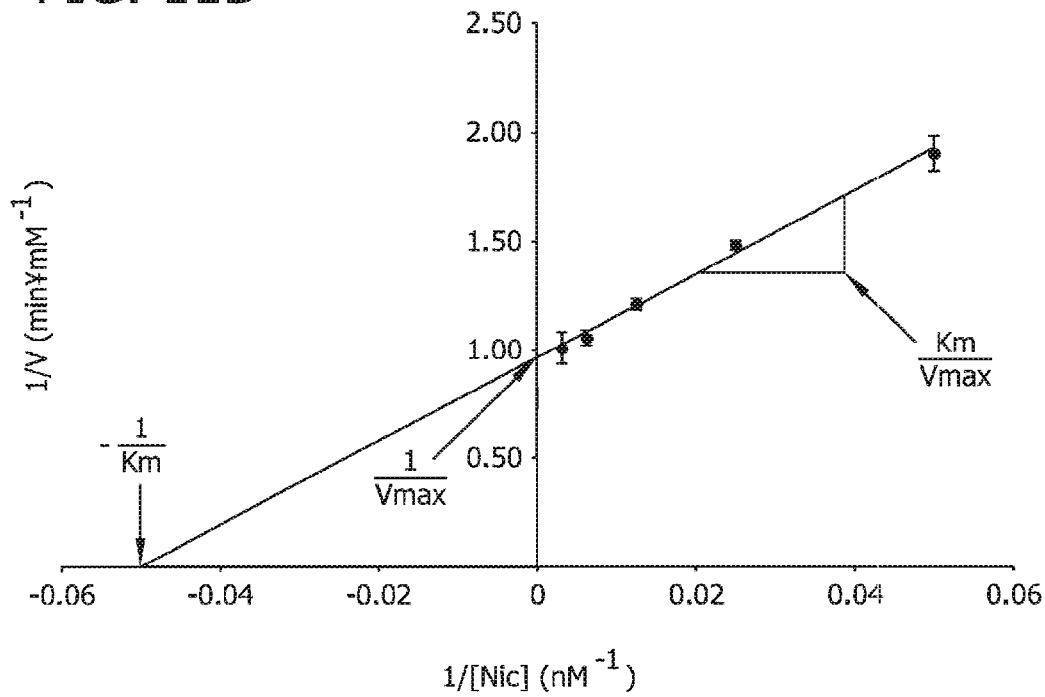

By using this enzyme-coupled fluorometric assay, kinetic parameters of purified recombinant mouse Nampt and Nmnat for nicotinamide and NMN, respectively, were determined (see, e.g., Table 1). The Lineweaver-Burk plots for these two enzymes are shown, for example, in FIGS. 11A and 11B. Compared to reported kinetic parameters of other enzymes in the NAD biosynthesis pathways (Micheli and Sestini, Methods Enzymol. (1997) 280, 211-221), Nampt shows very high affinity for its substrate ($K_m$=0.92 mM). The $K_m$ and $V_{max}$ of mouse Nmnat are consistent with previously reported values for human NMNAT-1 (Emanuelli et al., J. Biol. Chem. (2001) 276, 406-412). The catalytic efficiency of Nampt is ~46-fold less than that of Nmnat, suggesting that the reaction of Nampt is the rate-limiting step in the synthesis of NAD from nicotinamide.

Figure 13A:
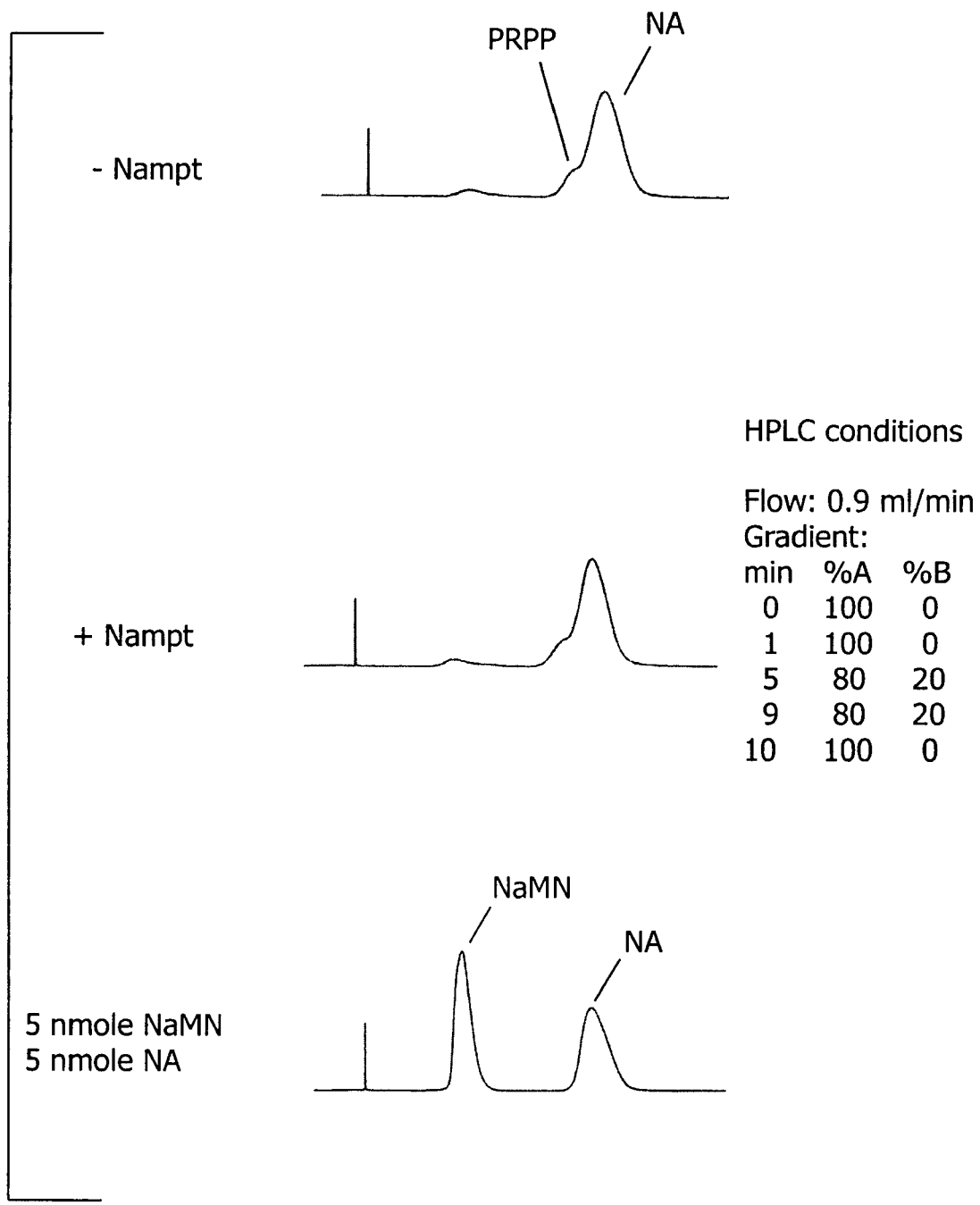
FIGS. 13A and 13B are a series of HPLC elution traces demonstrating that that Nampt does not catalyze the synthesis of nicotinic acid mononucleotide (NaMN) from nicotinic acid (NA) and phosphoribosyl pyrophosphate (PRPP). The Nampt reactions with nicotinic acid and nicotinamide (Nic) were conducted at 37° C. for 60 min in 500 ml of reaction buffer, and each reaction product was analyzed by HPLC (see Example 2). The flow rate and the gradient conditions for the detection of NaMN and NA are shown in the figure. While Nampt exhibited a robust synthesis of nicotinamide mononucleotide (NMN) from nicotinamide and PRPP, it did not synthesize NaMN from nicotinic acid and PRPP.
Figure 13B:
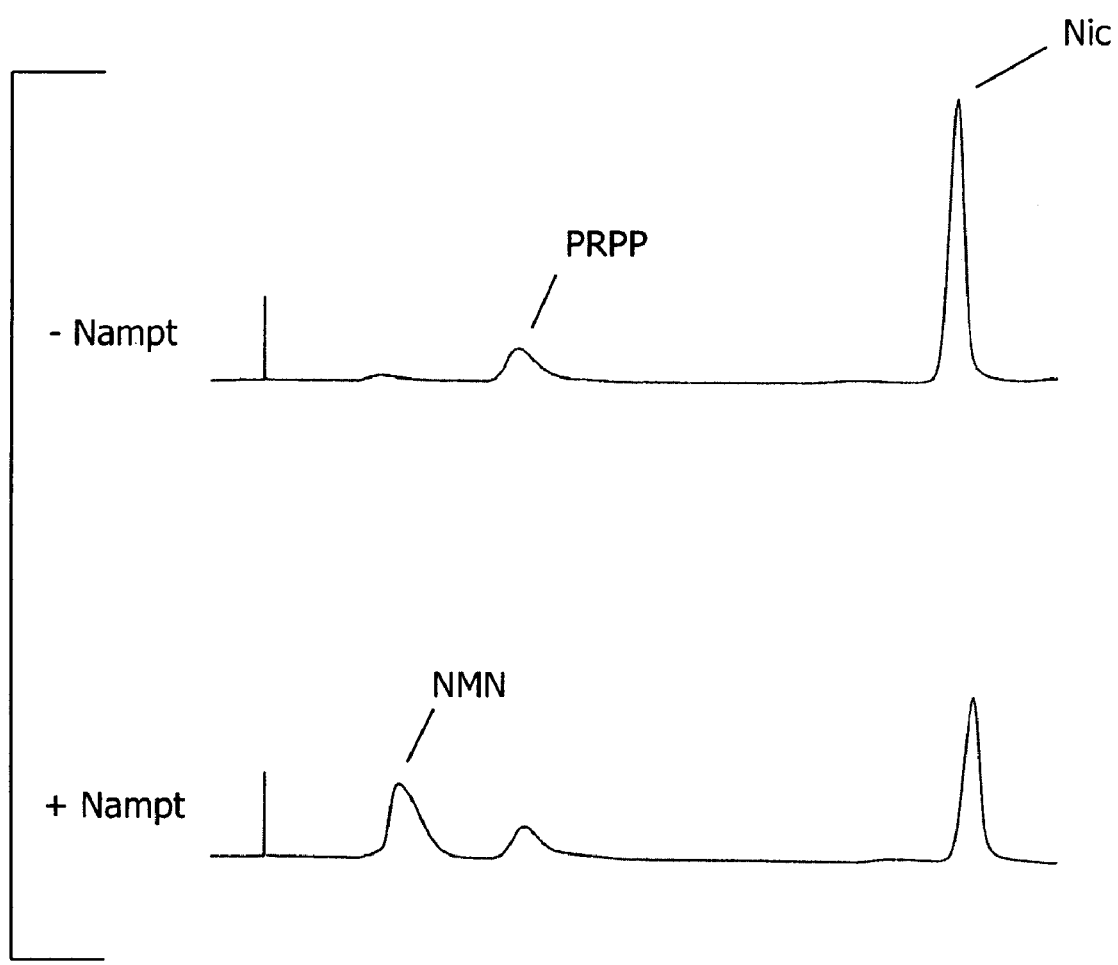

High performance liquid chromatography was used to detect Nampt reaction products. HPLC was performed with Waters 515 pumps and a 2487 detector (Waters, Mass.) with a Supelco LC-18-T column (15 cm×4.6 cm; Supelco, Pa.). The Nampt reaction was conducted at 37° C. for 15 min in 500 µl of reaction buffer (50 mM Tris-HCl [pH 7.5], 10 mM MgCl$_2$, 50 mM nicotinamide, 0.2 mM PRPP) with 50 µg of the recombinant Nampt protein. The reaction was terminated by adding 125 µl of 1 M HClO$_4$. Protein was then precipitated at 18,000 g, and 500 µl of the supernatant was neutralized with 40 µl of 3 M K$_2$CO$_3$. After centrifugation, 100 µl of sample was mixed with 400 µl of Buffer A (50 mM K$_2$PO$_4$/KHPO$_4$, pH 7.0) and loaded into the HPLC system. The products from Nampt reaction were monitored by absorbance at 261 nm. Results of HPLC detection of Nampt reaction products showed that the mouse Nampt produced nicotinamide mononucleotide (NMN) from nicotinamide and PRPP (see, e.g., FIG. 4D). Nampt failed to catalyze the synthesis of nicotinic acid mononucleotide (NaMN) from nicotinic acid and PRPP (see, e.g., FIGS. 13A and 13B), confirming the substrate specificity of this enzyme. In isolated reactions, it was also confirmed that Nmnat catalyzed the synthesis of NAD from NMN and ATP.

EXAMPLE 3

NAMPT Regulation of Cellular NAD Level in Mouse Fibroblasts

Because Nampt is the rate-limiting step in the mammalian NAD biosynthesis pathway starting from nicotinamide, increasing the dosage of Nampt increases total NAD levels in mammalian cells, as demonstrated with overexpression of the mouse Nampt gene in mouse NIH3T3 fibroblasts.

All NIH3T3 cell lines used in this study were established by selecting in the presence of 650-700 µg/ml of G418 (Invitrogen, CA). Approximately 1.2×10$^5$ NIH3T3 cells were plated in 6 cm dishes. Transfection occurred as described above.

Polyclonal rabbit antisera were produced against the purified full-length His-tagged Nampt and Nmnat recombinant proteins (Covance, Pa.). Specific antibodies were affinity-purified from these antisera with HiTrap affinity columns (Amersham Biosciences, NJ) conjugated with each protein.

For Western Blotting, whole cell extracts were prepared with Laemmli's sample buffer. Proteins were separated in SDS-PAGE with 4-15% gradient or 12% gels and transferred onto Immobilon-P transfer membranes (Millipore, Mass.). Uniform transfer was confirmed by Ponceau S staining. Membranes were blocked in Tris-buffered saline with 0.1% Tween 20 (TBS-T buffer) and 5% dry milk (w/v) for 1 h at room temperature and washed three times in TBS-T. Membranes were blotted overnight at 4° C. with primary antibodies diluted at an appropriate dilution ratio in TBS-T with 5% dry milk and then with a secondary donkey anti-rabbit IgG antibody conjugated with horseradish peroxidase (Amersham Biosciences) for 1 h at room temperature. After washing, signals were developed with the ECL detection system (Amersham Biosciences).

Figure 12A:
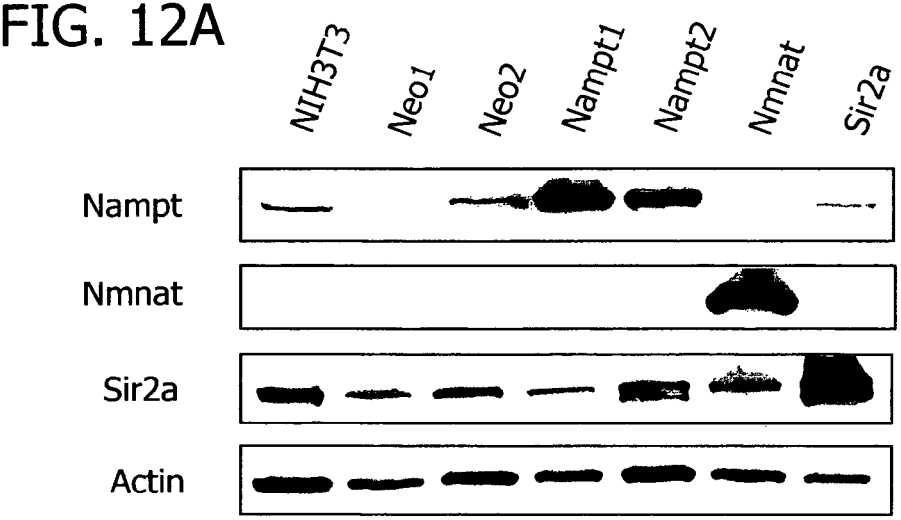
FIGS. 12A and 12B are a gel showing a Western blot and a bar graph, respectively, each depicting Nampt's role as the rate-limiting component in the mammalian NAD biosynthesis pathway initiated from nicotinamide. The effects of overexpression of Nampt, Nmnat, Sir2, and addition of nicotinamide on total cellular levels were assessed in mouse NIH3T3 cells.
Figure 12B:
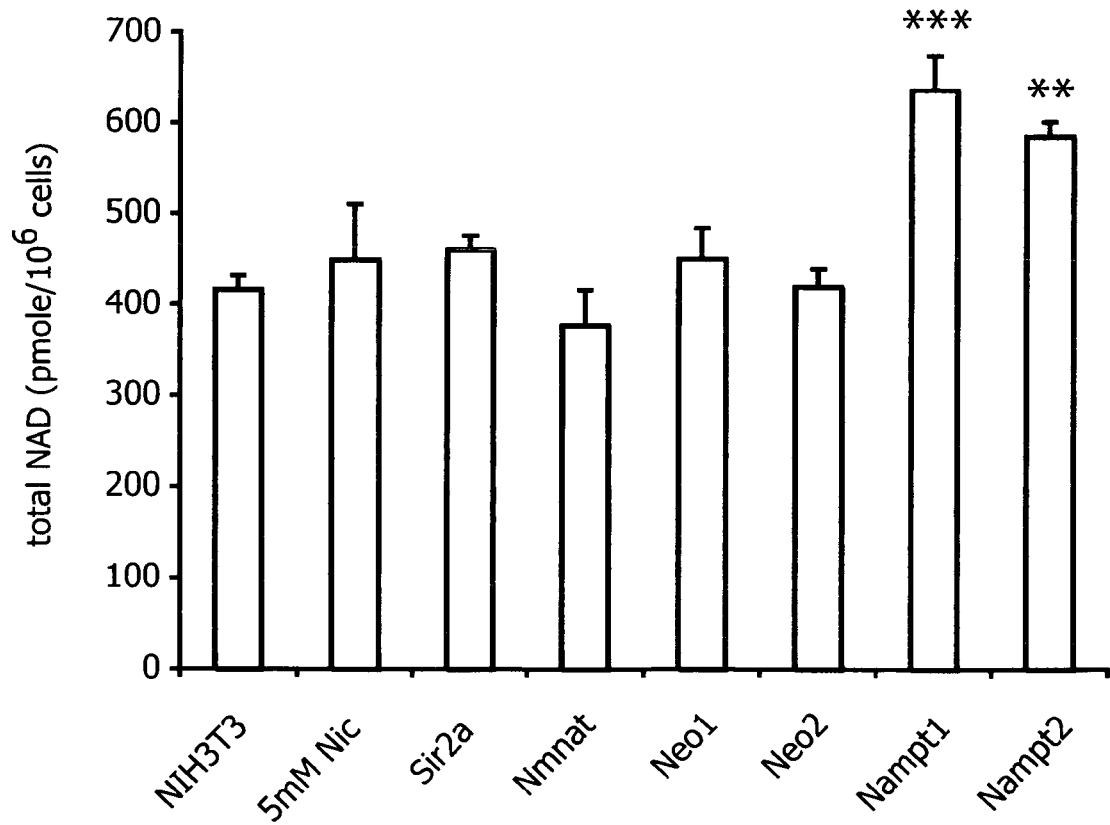

Results showed that in the original and neomycin-resistant control NIH3T3 cells, low amounts of the 56-kD Nampt protein were detected with an affinity-purified rabbit polyclonal antibody raised against the recombinant full-length protein (see, e.g., FIGS. 12A and 12B). Two Nampt-overexpressing NIH3T3 cell lines, Nampt1 and 2, showed 23- to 15-fold higher amounts of the protein, respectively, compared to control neomycin-resistant cell lines, Neo1 and 2 (see, e.g., FIGS. 12A and 12B). The amounts of Nmnat did not change in these cell lines.

Figure 14A:
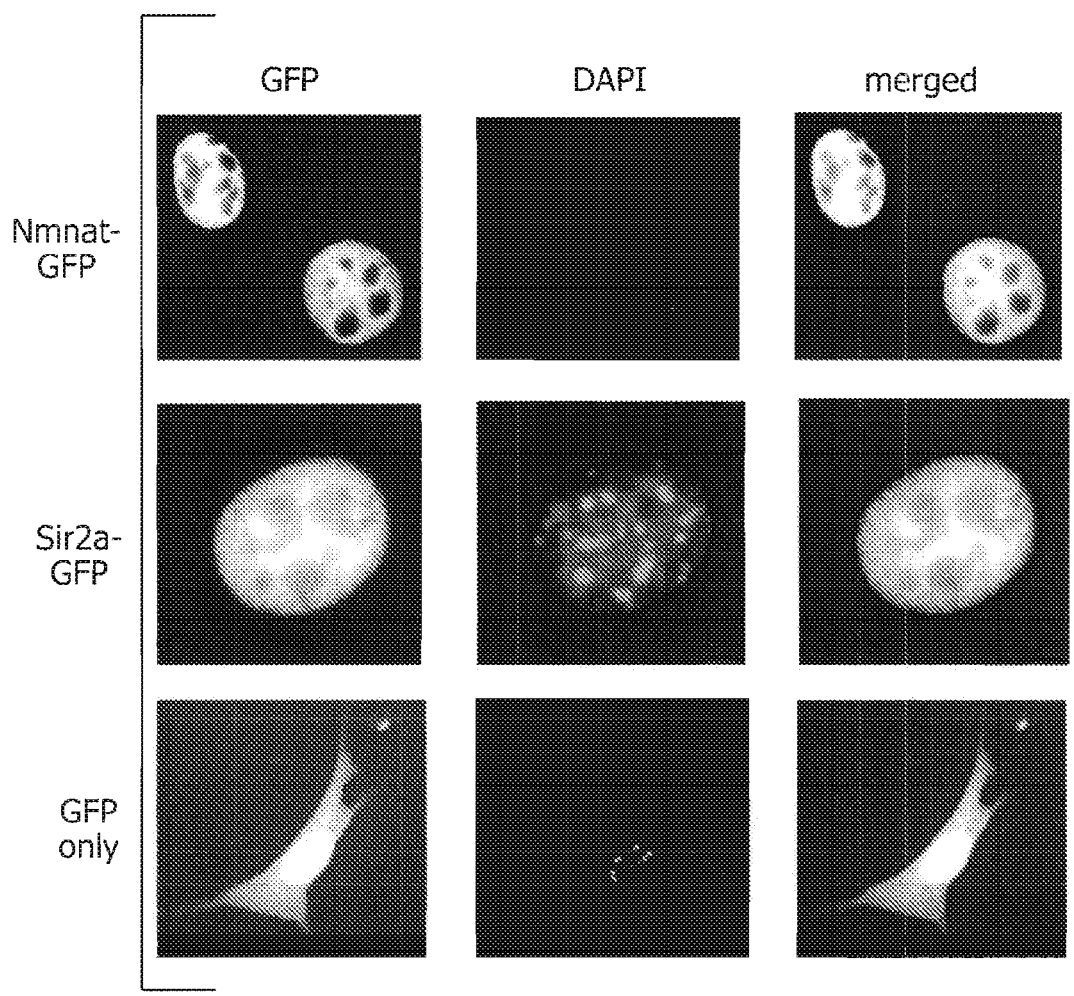
FIGS. 14A and 14B are a series of images that depict fluorescent localization of GFP-fused Nampt, Nmnat and Sir2α.
Figure 14B:
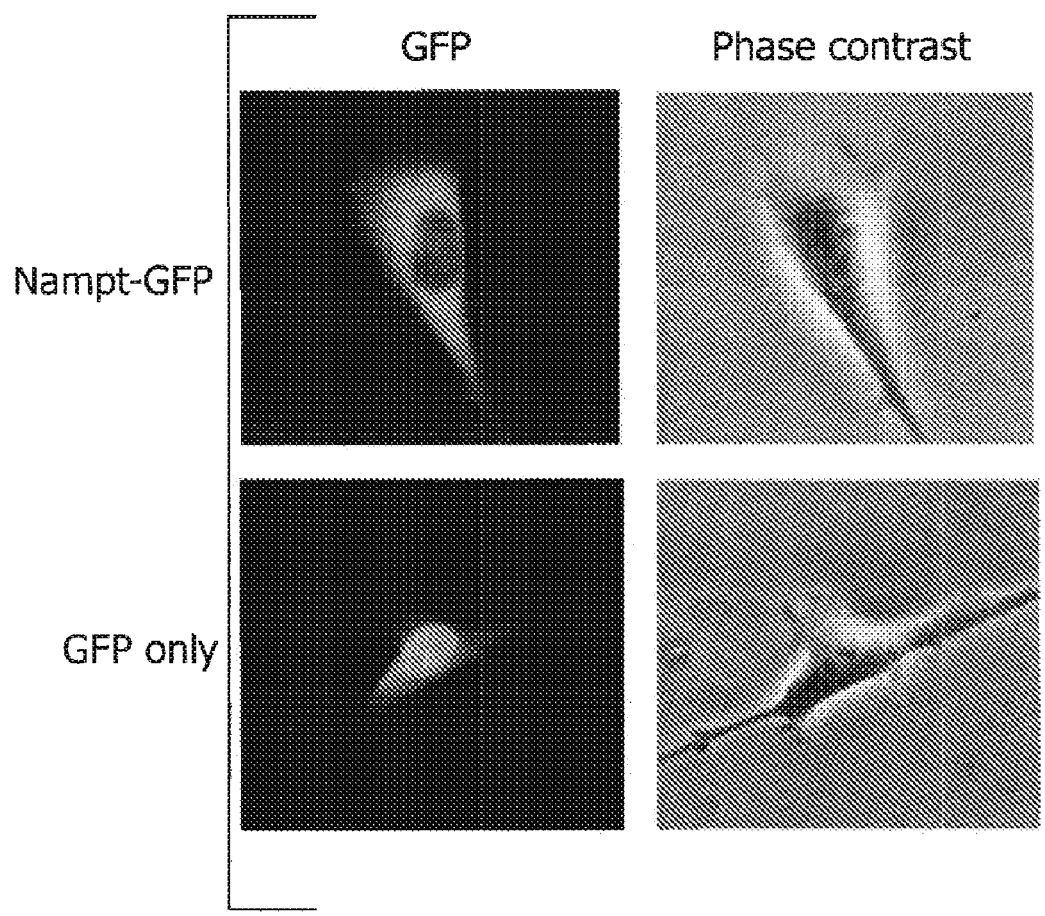

The mouse Nmnat and Sir2α genes in NIH3T3 cells were also overexpressed (see, e.g. FIGS. 12A and 12B). Nmnat (32 kD) and Sir2α (apparent molecular weight 110 kD) were detected with affinity-purified rabbit polyclonal antibodies against these proteins. Overexpression levels of Nmnat and Sir2α are approximately 14- and 4-fold, respectively. The amount of Nampt did not change in these cell lines. Using GFP-fusion expression vectors, it was also demonstrated that overexpressed Nmnat and Sir2α proteins were localized exclusively in the nucleus, while overexpressed Nampt protein was mainly localized in cytoplasm (see, e.g., FIGS. 14A and 14B). The cells were fixed with 3.2% paraformaldehyde, treated with PBS containing 0.5% IGEPAL (Sigma), and stained with 50 ng/ml DAPI. As shown in FIG. 14A, Nmnat-GFP and Sir2α-GFP exhibited exclusive nuclear localization, as described in Luo et al., Cell, (2001) 107, 137-148; and Schweigler et al., FEBS Lett., (2001) 492, 95-100. As shown in FIG. 14B, Nampt-GFP was mainly localized in cytoplasm, as described in Kitani et al., FEBS Lett. (2003) 544, 74-78.

Total cellular levels of NAD was measured in the NIH3T3 cell lines overexpressing the untagged enzymes. High performance liquid chromatography was used to measure NAD (Neubert et al., Biochim. Biophys. Acta., (1964) 92, 610-612; Emanuelli et al., J. Chromatogr., (1996) B. 676, 13-18). Briefly, 5×10$^5$ cells were plated in 6 cm dishes and harvested 48 h later in 800 µl of ice-cold PBS. Cells were then spun down and lysed with 300 µl of 1M HClO$_4$ on ice for 10 min. Lysates were cleared by centrifugating at 4° C. at 18,000 g for 5 minutes. Cleared lysates (240 µl) were neutralized by adding 80 µl of 3M K$_2$CO$_3$ and incubating on ice for 10 minutes. After centrifuging for 10 min, 100 µl of the supernatant were mixed with 400 µl of Buffer A and loaded onto the column.

The HPLC was run at a flow rate of 1 ml/min with 100% Buffer A from 0 to 5 min, a linear gradient to 95% Buffer A and 5% Buffer B (100% methanol) from 5 to 6 min, 95% Buffer A and 5% Buffer B from 6 to 11 min, a linear gradient to 85% Buffer A and 15% Buffer B from 11 to 13 min, 85% Buffer A and 15% Buffer B from 13 to 23 min, and a linear gradient to 100% Buffer A from 23 to 24 min. NAD was eluted as a sharp peak at 22 min. The amount of NAD was quantitated based on the peak area compared to a standard curve.

Results showed that total NAD levels increased 47 and 35% in Nampt1 and 2 cell lines, respectively, compared to those in control cell lines (see, e.g., FIG. 12B). In contrast, the total NAD levels did not change in cells overexpressing Nmnat or Sir2α (see, e.g., FIG. 12B). Addition of 5 mM nicotinamide to the medium, which otherwise contains only 33 µM nicotinamide, did not increase NAD (see, e.g., FIG. 12B). Consistent with the biochemical characteristics of these enzymes, these results suggest that Nampt is the rate-limiting component of the NAD biosynthesis pathway starting from nicotinamide in mouse fibroblasts.

EXAMPLE 4

Tissue Distribution of NAMPT and its Fasting-Induced Increase

In this Example, various tissue samples of fed and fasted mice were analyzed for the expression of intracellular Nampt.

Adult mice (C57BL/6; male; 3-4 months of age) were sacrificed by carbon dioxide asphyxiation consistent with the recommendation of the Panel on Euthanasia of the American Veterinary Medical Association. Tissues and organs (lung, spleen, brain, testis, pancreas, visceral fat (WAT), brown adipose tissue (BAT), heart, muscle, liver, and kidney) were surgically extracted, homogenized, and boiled in Laemmli's sample buffer. Proteins were quantitated with the Bradford assay (Biorad, CA), separated using a 7.5% SDS-PAGE gel, and transferred onto Immobilon-P membranes (Millipore, Mass.). Each tissue extract (~22.5 µg) was analyzed using the Western blotting protocol and the primary antibodies described above in Example 3. As a positive control, an NIH3T3 cell line overexpressing Nampt (Nampt1) was employed (~5 µg), also described in Example 3. Nampt was highly expressed in BAT, kidney, liver, heart, and muscle. Expression was lower in WAT, testis, spleen, lung, brain, and pancreas (see, e.g., FIG. 5A).

Figure 5B:
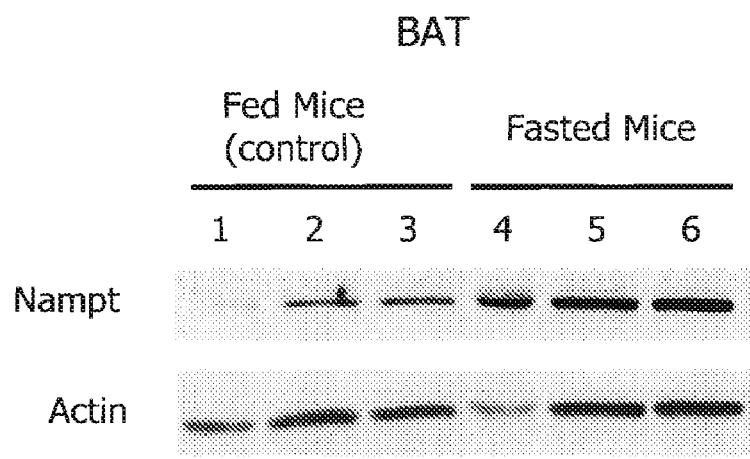
Figure 5C:
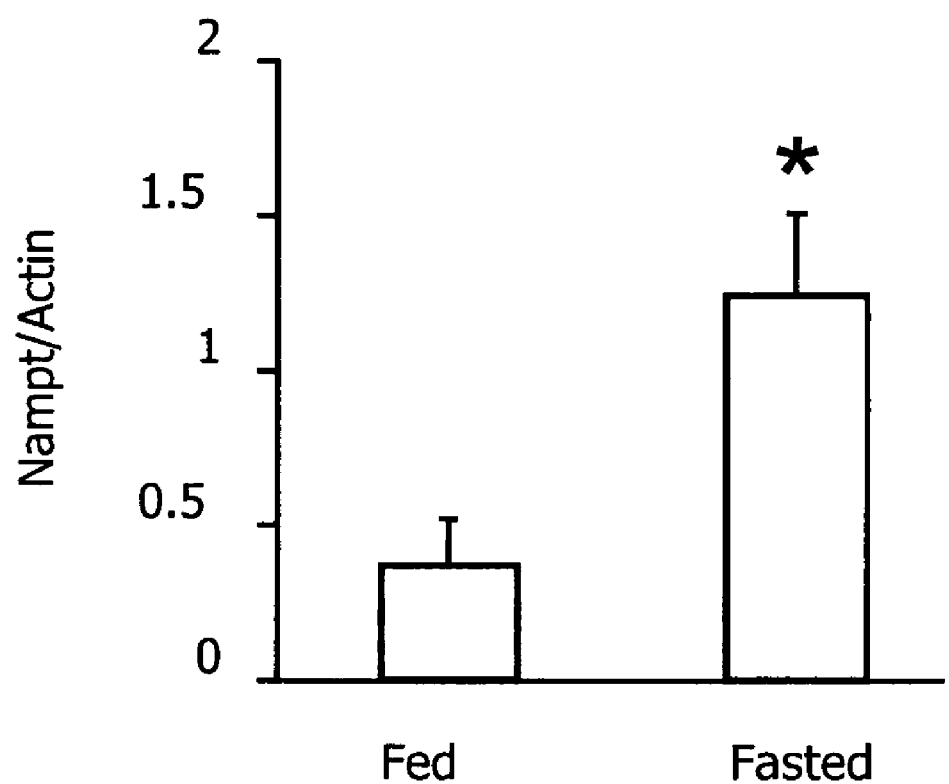

Protein expression levels of Nampt were also measured in BAT in response to fasting and compared to fed controls. Food was withdrawn from adult mice (C57BL/6; female; 3-4 months of age) at sunset and the mice fasted for 16 hours. Control fed mice were of similar age and sex to fasted mice except that the food source was not withdrawn. All mice were immediately asphyxiated with carbon dioxide and their BAT extracted and analyzed as previously described. Data was quantitated and normalized to actin expression levels. Intracellular Nampt levels increased about 3-fold in fasted mice as compared to fed controls (see, e.g., FIGS. 5B and 5C). Without being bound to a single theory, these results may reflect an increase in Nampt protein synthesis, an inhibition of secretion of Nampt, or both, under fasting.

EXAMPLE 5

Induction and Secretion of Extracellular Version of NAMPT from Brown Preadipose Cells As demonstrated in Example 4, BAT exhibited the highest expression levels of Nampt. In this Example, a BAT-derived preadipocyte cell line termed HIB-1B was differentiated into mature brown adipocytes and the production of an extracellular version of Nampt was analyzed.

HIB-1B cells were maintained at confluence for 2 days and then differentiation was induced by Dulbecco's Modified Eagle's Medium (DMEM) containing 10% FBS with 1.0 uM Dexamethasone, 0.5 mM 3-lsobutyl-1-methylxanthine, 1 nM 3,3',5'-Triiodo-L-thyronine (T3), and 10 ug/mL insulin (all from Sigma, MO) for 2 days. The media was then replaced with DMEM 10% FBS supplemented with 1 nM T3 and 10 ug/mL insulin and replaced every two days. A similar protocol was followed for the WAT preadipocyte 3T3-L1 cells, except that the media contained no T3 hormone. Cell extracts (~45 µg) and culture media (~20 µg) was analyzed using the Western blotting protocol and the primary antibodies described above in Example 3. As a positive control, an NIH3T3 cell line overexpressing Nampt (Nampt1) was employed (~10 µg), also described in Example 3.

Upon adipocyte differentiation intracellular Nampt expression increased in both HIB-1B and 3T3-L1A cell lines. The presence of and an increase in a secreted extracellular Nampt was also identified during differentiation of the HIB-1B cells. Media containing no serum, but supplemented with insulin and T3, also expressed extracellular Nampt (see, e.g., FIGS. 6A and 6B).

Additionally, a secreted extracellular Nampt was also observed in insulin-supplemented, serum-free media containing differentiated 3T3-L1 adipocytes. Based on the reference marker (Nampt1), the same volume of HIB-1B culture media contained increased levels of the extracellular Nampt as compared to 3T3-L1 culture media (see, e.g., FIGS. 6A-6B).

Figure 7A:
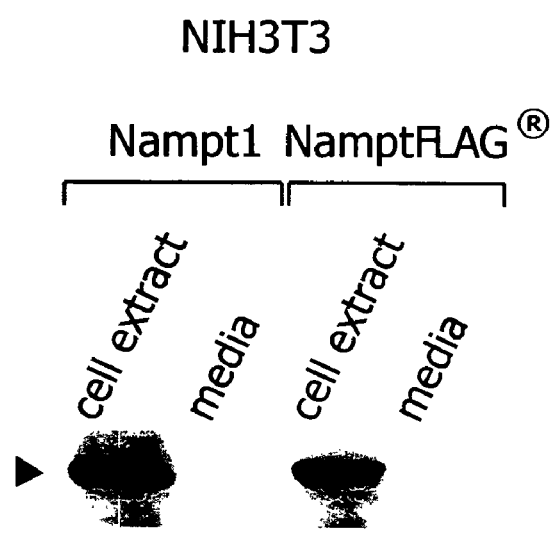
FIGS. 7A and 7B are images of gels showing that other cell types do not secrete an extracellular version of Nampt.
Figure 7B:
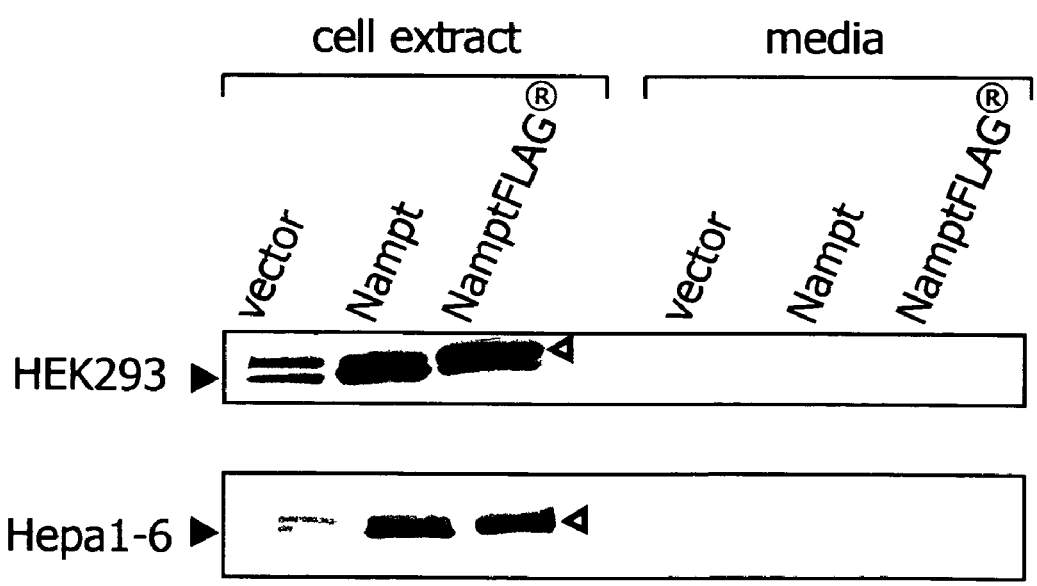

The media and cell extracts of NIH3T3, Hepa1-6, and Hek293 cells grown under normal conditions (DMEM 10% FBS) were also analyzed using the above protocol. No secretion of extracellular Nampt was observed in these systems (see, e.g., FIGS. 7A and 7B).

EXAMPLE 6

Detection of Extracellular NAMPT in Mouse Plasma

In this Example, the existence of extracellular Nampt/visfatin in mouse plasma was also confirmed by Western blotting with the affinity-purified rabbit polyclonal Nampt antibody according to the procedure described above in Example 3.

Figure 6A:
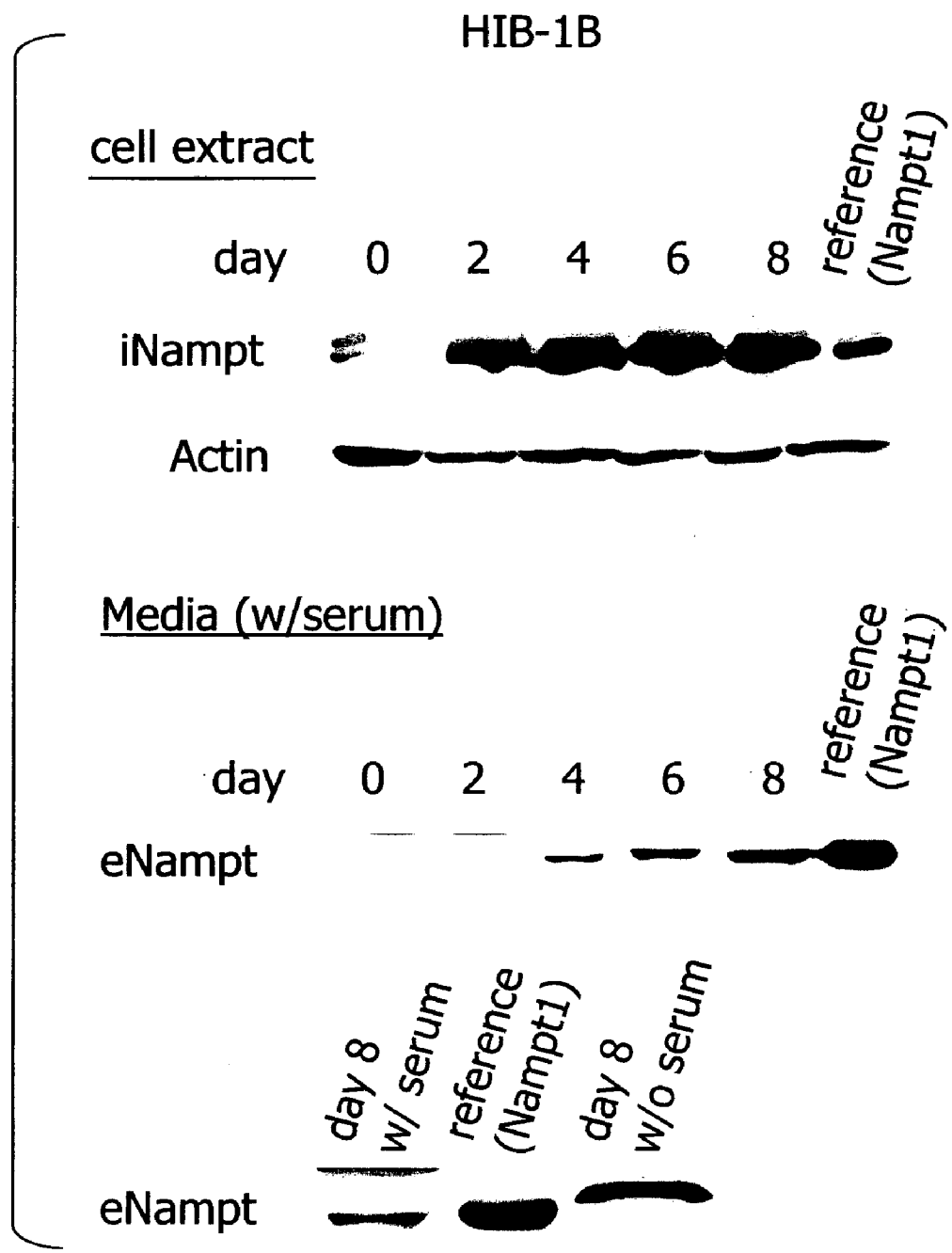
FIGS. 6A and 6B are images of gels showing the induction and secretion of Nampt during differentiation of brown and white adipocytes.
Figure 6B:
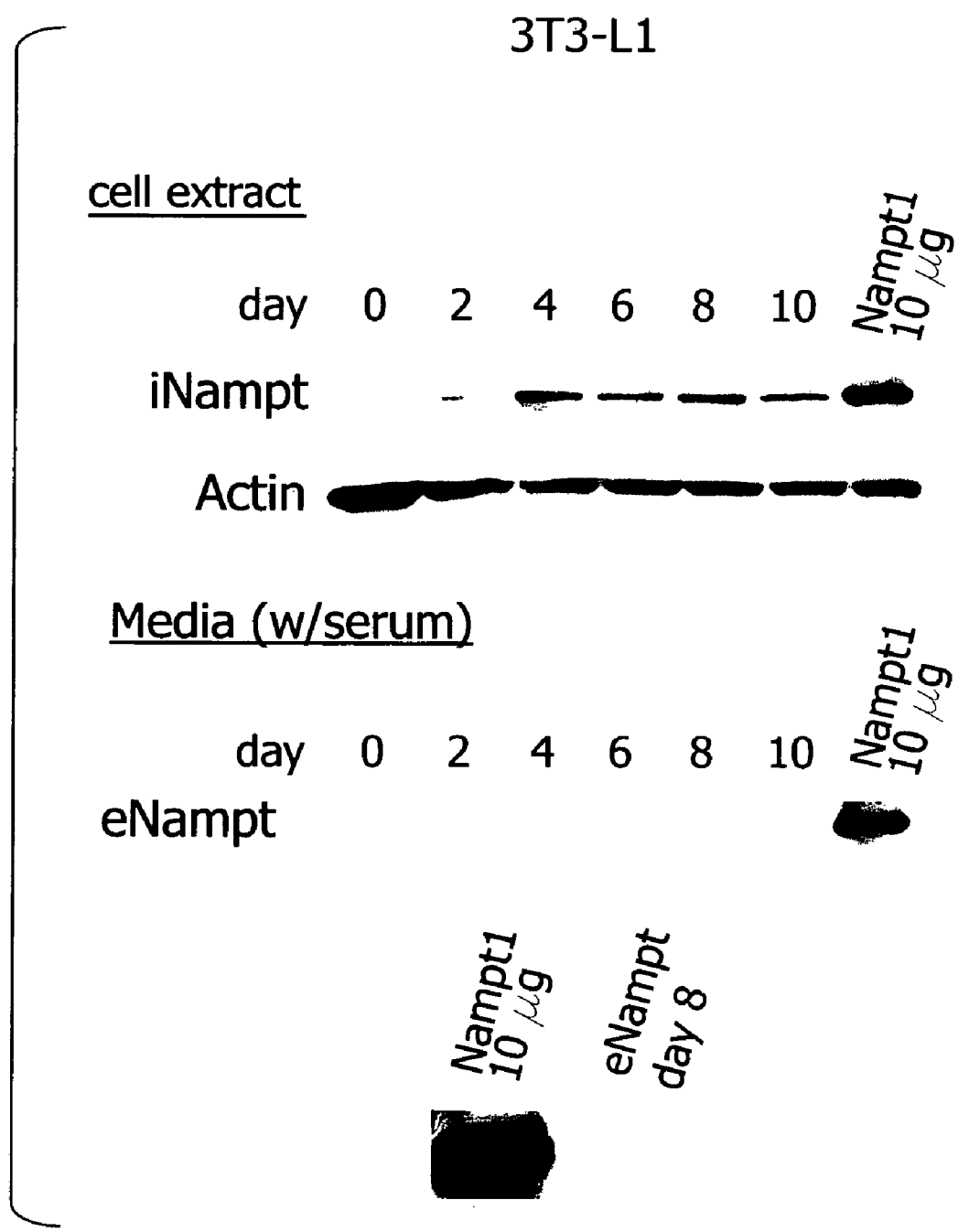
Figure 8:
FIG. 8 is a gel showing that mouse plasma contains a larger version of Nampt than the intracellular version of Nampt. Plasma samples were collected from three C57BL/6 mice and were analyzed (see Example 6). Nampt1 cell extract was loaded as a reference. Closed and open arrowheads indicate the larger extracellular version of Nampt in plasma and the intracellular version of Nampt, respectively.

The extracellular Nampt detected in mouse plasma exhibited a larger apparent molecular mass (i.e., about 56 kD to about 57 kD) as compared to intracellular Nampt. Additionally, freeze/thaw cycles of the plasma samples created a second band having an apparent molecular mass closer to the size of intracellular Nampt (FIG. 8, see lanes 1 and 2). These findings are consistent with the observation of a higher molecular weight form and the labile nature of extracellular Nampt secreted from differentiated HIB-1B brown adipocytes (see Example 5; FIG. 6A).

EXAMPLE 7

Figure 9A:
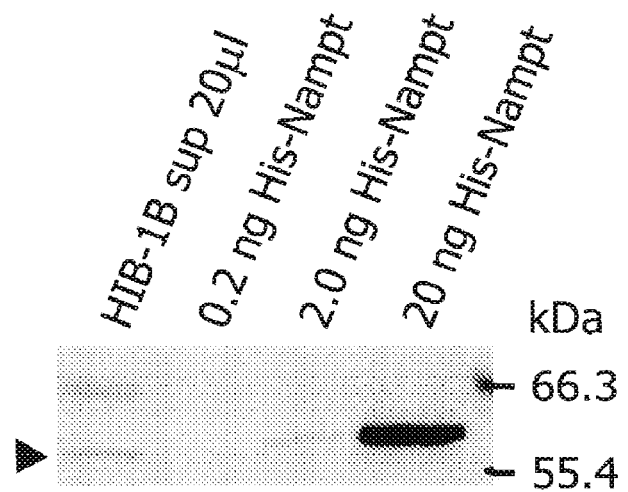
FIGS. 9A, 9B, and 9C are gels showing the partial purification of the extracellular version of Nampt from the culture supernatant of differentiated HIB-1B brown adipocytes.

Partial Purification of an Extracellular Version of NAMPT from Cell Culture Supernatant The concentration of extracellular Nampt in the HIB-1B culture supernatants was estimated as ~100 ng/ml by comparing the amount extracellular Nampt in the supernatant (~20 μl) to standards of the purified His-tagged Nampt protein produced according to the method described in Example 1 (see FIG. 9A).

Figure 9B:
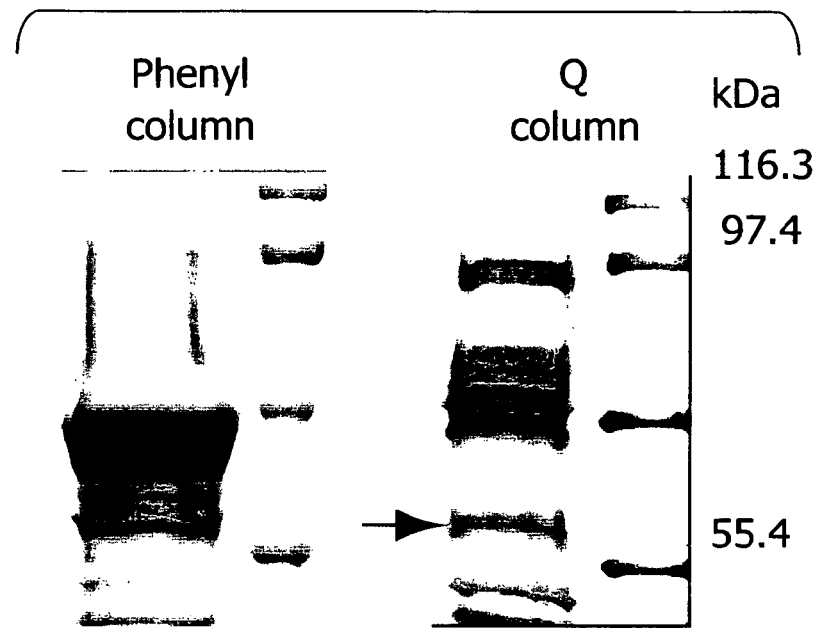
Figure 9C:
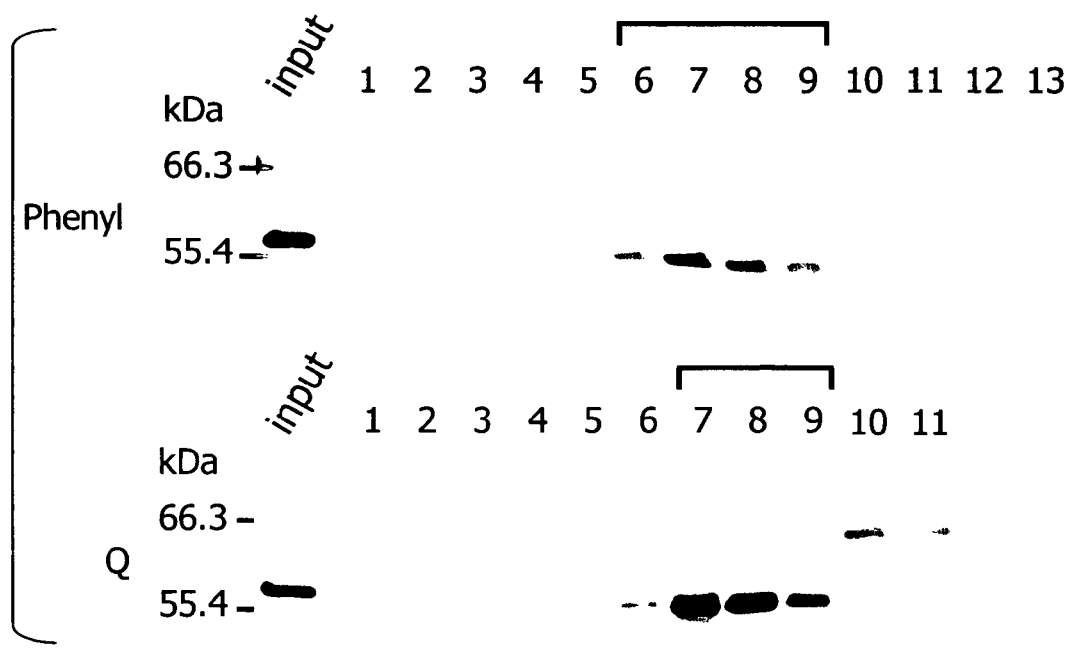
Figure 10A:
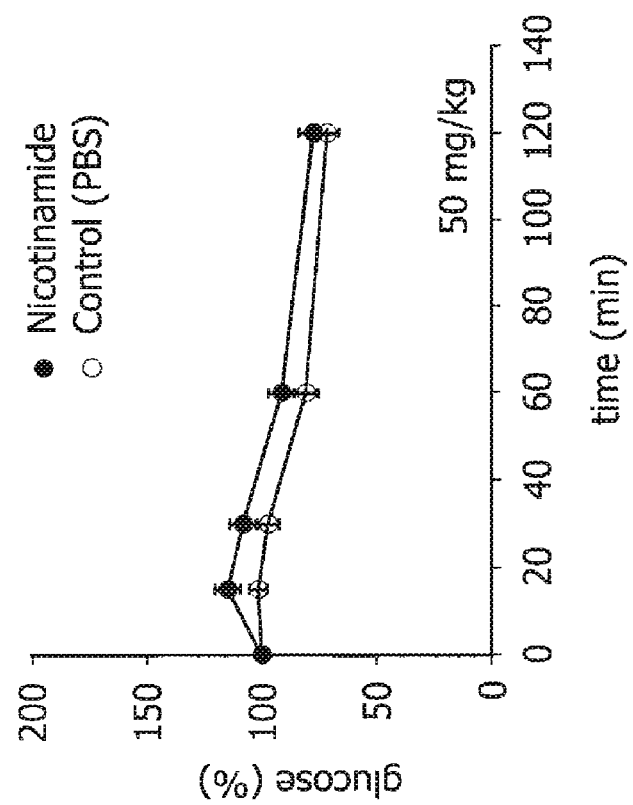
FIGS. 10A, 10B, 10C, 10D, 10E, and 10F are graphs of blood glucose levels in C57BL/6 mice following administration of nicotinamide (FIGS. 10A and 10B), nicotinamide mononucleotide (NMN) (FIGS. 10C and 10D), and NAD (FIGS. 10E and 10F), in 500 mg/kg and 50 mg/kg doses (see Example 8). All results are expressed as mean ±standard error. A single asterisk indicates $p \leq 0.05$. A double asterisk indicates $p \leq 0.01$. A triple asterisk indicates $p \leq 0.001$.
Figure 10B:
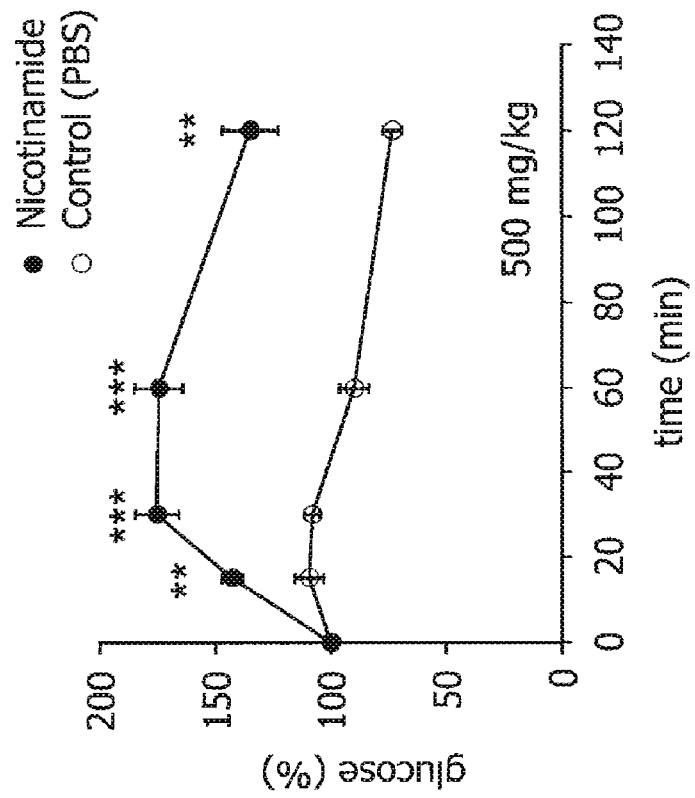
Figure 10C:
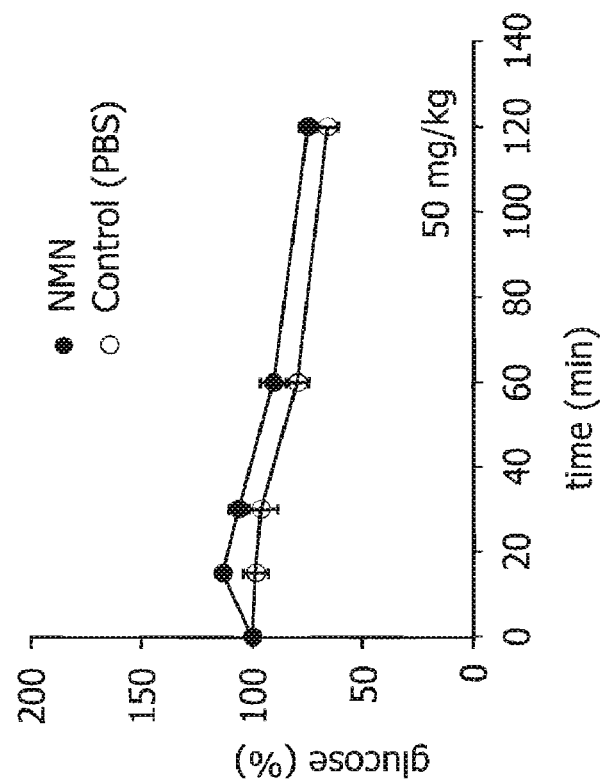
Figure 10D:
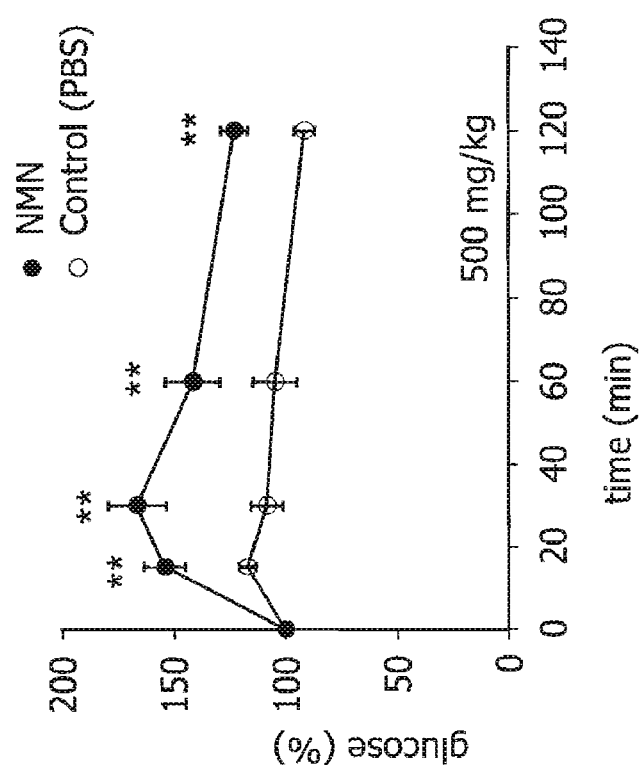
Figure 10E:
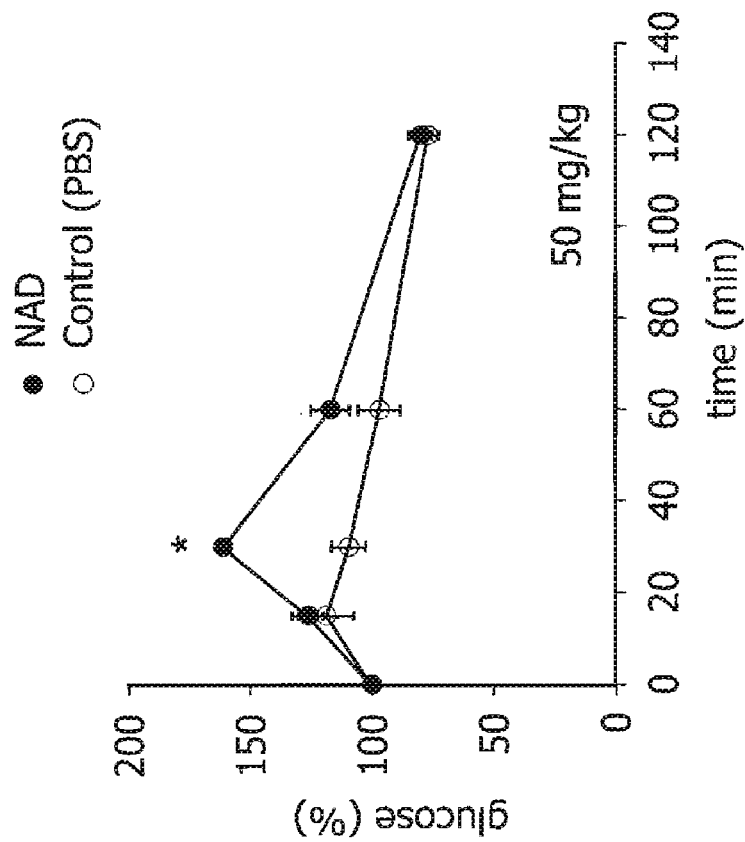
Figure 10F:
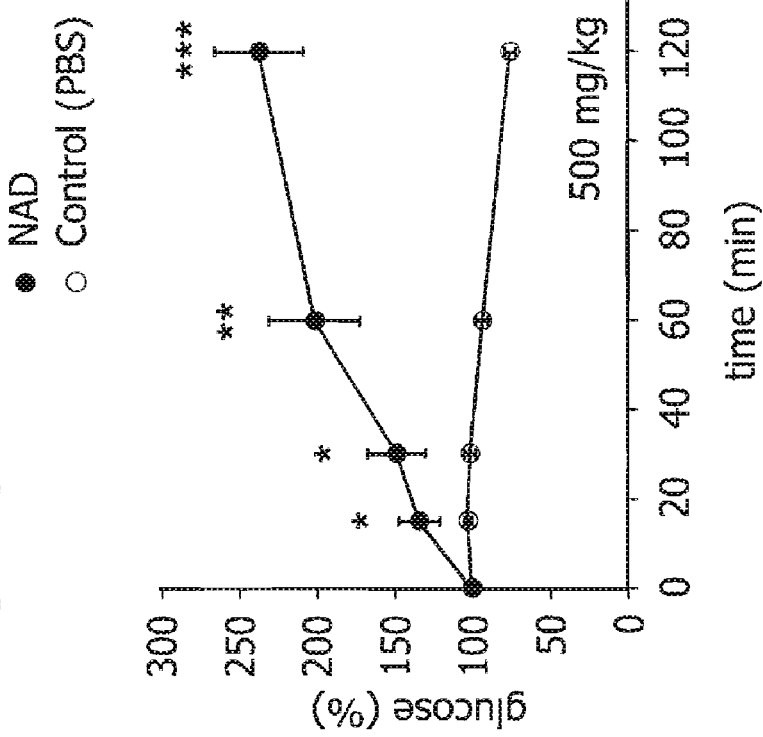

Partial purification of extracellular Nampt from HIB-1B media was accomplished by loading extracellular Nampt from HIB-1B culture supernatants onto a Phenyl-FF column (Amersham) in buffer A [0.5 M $(NH_4)_2SO_4$, 20 mM NaCl, 25 mM Tris 8.5, 1 mM DTT] and eluting in a linear gradient with buffer B [20 mM NaCl, 25 mM Tris 8.5, 1 mM DTT]. Fractions containing extracellular Nampt were concentrated, desalted, and reloaded onto a Q-FF column (Amersham) in buffer B. Elution was accomplished with a linear gradient of buffer C [1.0 M NaCl, 25 mM Tris 8.5, 1 mM DTT] and fractions (15 and 2.5 μg) containing extracellular Nampt were concentrated and analyzed by SDS-PAGE and Coomassie Brilliant Blue staining (see FIGS. 9B-9C). A band the expected size of extracellular Nampt was obtained and further confirmed by mass spectrometry to contain Nampt signature peptide sequences.

EXAMPLE 8

Increasing Blood Glucose Concentration of a Mammal by Administration of Nicotinamide, NMN, or NAD In this Example, five adult mice (C57BL/6; male; 3-4 months of age) were subjected to a 4-hr fast followed by intraperitoneal injection (500 mg/kg; 50 mg/kg) of nicotinamide, nicotinamide mononucleotide (NMN), or nicotinamide adenine dinucleotide (NAD). A control group of five fasted mice (16 hours) were injected with PBS.

Blood glucose levels were measured from tail vein blood samples with an Accu-Chek glucometer (Roche Diagnostics) at 0, 15, 30, 60 and 120 min after injection. At a dose of 500 mg/kg, all of these compounds significantly increased blood glucose levels (FIGS. 10A-10F). While nicotinamide and NMN had similar kinetics of glucose increase (e.g., FIGS. 10A and 10C), NAD elicited a much more pronounced and long-lasting effect on blood glucose levels (e.g., FIG. 10E). The effects of these compounds were weaker at a dose of 50 mg/kg (e.g., FIGS. 10B, 10D, and 10F), suggesting that the effects are dose-dependent.

EXAMPLE 9

Purification of an Extracellular Version of NAMPT from Mouse Plasma

Plasma from C57BL/6 mice will be collected and diluted with buffer A (25 mM Tris-HCl [pH8.5], 20 mM NaCl, 0.5 M $Na_2SO_4$, 1 mM DTT). The diluted plasma will be subjected to a Butyl-Sepharose hydrophobic column (Amersham) in an automated ÄKTA FPLC system (Amersham Pharmacia) and fractionated with increasing concentrations of buffer B (25 mM Tris-HCl [pH8.5], 20 mM NaCl, 1 mM DTT). Each fraction will be examined by Western blotting with a Nampt-specific antibody, and fractions containing extracellular Nampt will be combined and diluted with buffer A. The combined fraction will then be subjected to a Phenyl-Sepharose High Performance column (Amersham) and fractionated with increasing concentrations of buffer B. Fractions containing extracellular Nampt will be combined, desalted, and diluted with buffer B. Next, the sample will be fractionated in a Mono Q-Sepharose anion exchange column (Amersham) with increasing concentrations of buffer C (25 mM Tris-HCl [pH8.5], 1 M NaCl, 1 mM DTT). The purified extracellular Nampt protein in the final combined fraction will be separated in SDS-PAGE and examined by staining with SYPRO Ruby (Bio-Rad) or Coomassie Brilliant Blue (Sigma) and by Western blotting with the Nampt antibody.

EXAMPLE 10

Purification of an Extracellular Version of NAMPT from Culture Media

Culture supernatant from confluent cultured HIB-1B cells will be collected and diluted with buffer A (25 mM Tris-HCl [pH8.5], 20 mM NaCl, 0.5 M $Na_2SO_4$, 1 mM DTT). The diluted supernatant will be subjected to a Butyl-Sepharose hydrophobic column (Amersham) in an automated ÄKTA FPLC system (Amersham Pharmacia) and fractionated with increasing concentrations of buffer B (25 mM Tris-HCl [pH8.5], 20 mM NaCl, 1 mM DTT). Each fraction will be examined by Western blotting with a Nampt-specific antibody, and fractions containing extracellular Nampt will be combined and diluted with buffer A. The combined fraction will then be subjected to a Phenyl-Sepharose High Performance column (Amersham) and be fractionated with increasing concentrations of buffer B. Fractions containing extracellular Nampt will be combined, desalted, and diluted with buffer B. Next, the sample will be fractionated in a Mono Q-Sepharose anion exchange column (Amersham) with increasing concentrations of buffer C (25 mM Tris-HCl [pH8.5], 1 M NaCl, 1 mM DTT). The purified extracellular Nampt protein in the final combined fraction will be separated in SDS-PAGE and examined by staining with SYPRO Ruby (Bio-Rad) or Coomassie Brilliant Blue (Sigma) and by Western blotting with the Nampt antibody.

EXAMPLE 11

Measurement of the Enzymatic Activity of Purified Extracellular NAMPT by the Enzyme-Coupled Fluorometric Assay and HPLC The purified extracellular Nampt protein will be subjected to the enzyme-coupled fluorometric assay that was established in U.S. Patent Application Ser. No. 60/645,174. The reaction products will also be analyzed by HPLC.

Enzyme-coupled fluorometric assays: 100-500 ng of the purified extracellular Nampt and varying concentrations of nicotinamide will be reacted at 37° C. in 100 μl of a buffer containing 50 mM Tris-HCl [pH 7.5], 0.02% BSA, 12 mM $MgCl_2$, 2.5 mM ATP, 10 μg/ml His-tagged Nmnat, 0.4 mM phosphoribosyl pyrophosphate (PRPP), 1.5% ethanol, and 30 μg/ml alcohol dehydrogenase. The production of NADH will be measured by excitation at 340 nm and emission at 460 nm in a fluorometer. The $K_m$, $V_{max}$, and $k_{cat}$ values for extracellular Nampt will be calculated from these measurements.

HPLC-based assays: HPLC will be performed with Waters 515 pumps and a 2487 detector (Waters, Mass.) with a Supelco LC-18-T column (15 cm×4.6 cm; Supelco, Pa.). The Nampt reaction will be conducted at 37° C. for 1-2 h in 500 µl of reaction buffer (50 mM Tris-HCl [pH 7.5], 10 mM $MgCl_2$, 50 mM nicotinamide, 0.2 mM PRPP) with 5 µg of the purified extracellular Nampt protein. The reaction will be terminated by adding 125 µl of 1 M $HClO_4$. Protein will then be precipitated at 18,000 g, and 500 µl of the supernatant will be neutralized with 40 µl of 3 M $K_2CO_3$. After centrifugation, 100 µl of sample will be mixed with 400 µl of the buffer (50 mM $K_2PO_4$/$KHPO_4$, pH 7.0) and loaded into the HPLC system. The products from extracellular Nampt reaction will be monitored by absorbance at 261 nm.

EXAMPLE 12

Identification of the Modification of Extracellular NAMPT by Mass Spectroscopic Analysis To identify the nature of the modification of extracellular Nampt, electronspray ionization (ESI) nano-liquid chromatography (LC)-linear quadrupole ion trap Fourier-transform ion cyclotron resonance mass spectrometry (nano-LC-FT-MS) will be employed. In recent years, the development of accurate mass-based proteomics (Bogdanov et al., Mass Spectrom. Rev., (2005) 24, 168-200) and gas-phase fragmentation methods (Aebersold et al., Nature, (2003) 422, 198-207) have provided unprecedented specificity for high-throughput, database-assisted protein identification and characterization of post-translational modifications. Additionally, King et al. (unpublished manuscript) recently applied nano-LC-FT-MS to identify novel autophosphorylation sites of human checkpoint 2 (Chk2) protein kinase. In this study, four nano-LC-FT-MS analyses, consuming approximately 1 µg per analysis, yielded 81% coverage of the Chk2 amino acid residues and identified 11 Chk2 autophosphorylation sites. Nano-LC-FT-MS has also been applied for the analysis of histone modifications (acetylation and methylation) (Syka et al., J. Proteome Res., (2004) 3, 621-626) and protein phosphorylation (Gruhler et al., Mol. Cell. Proteomics, (2005) 4, 310-327). Because of accurate mass measurements and high-throughput MS/MS spectral acquisition, the nano-LC-FT-MS analysis is the best methodology to analyze the unknown nature of the modification of extracellular Nampt.

Nano-LC-FT-MS: Mass spectrometry of peptides will be performed using a linear quadrupole ion trap Fourier transform ion cyclotron resonance mass spectrometer (LTQ-FTMS, Thermoelectron, San Jose, Calif.). The nano-liquid chromatograph (Eksigent nano-LC, Eksigent, Livermore, Calif.) is interfaced to the LTQ-FTMS with a Pico-View nanocapillary electrospray source from New Objective (Woburn, Mass.). Sample injection will be performed with a low-volume autosampler (Endurance, Spark, Plainsboro, N.J.). For analysis of peptides, the column will be a C-18 PicoFrit (75 µm×10 cm) (New Objective, Woburn, Mass.). The mobile phases will be HPLC grade water (Fisher Scientific, Pittsburgh, Pa.) containing 1% formic acid (Sigma-Aldrich, St. Louis, Mo.) (Solvent A) and acetonitrile (Honeywell, Burdick & Jackson, Muskegon, Mich.) containing 1% formic acid (Solvent B). The peptide samples (5 µL) will be loaded at 600 nL/min at 1% B for 10 min. The flow rate will then be decreased to 200 nL/min with isocratic elution for 20 min, followed by a linear increase in Solvent B (2%/min) for 40 min. The LTQ-FTICR (7 Tesla) mass spectrometer will be operated in either the data-dependent or data-directed mode with a dynamic inclusion accurate mass list. The survey scans (m/z=450–1500) will be acquired using the FTICR-MS with resolution of ~100,000 at m/z=421.75 after ion accumulation in the trap to a value of ~1,000,000. The ten most abundant ions will be isolated and analyzed after reaching a target value of ~40,000. The MS/MS isolation width will be 2.5 and the normalized collision energy will initially be set at 35%. Electrospray ionization will be accomplished with a spray voltage of 2.8-3.1 kV without sheath gas, and the temperature of the ion transfer tube will be set to 200° C.

Identification of the modifications of plasma extracellular Nampt by nano-LC-FT-MS: The purified plasma extracellular Nampt protein will be subjected to trypsin or chymotrypsin digestion, and the resultant peptides will be analyzed using nano-LC-FT-MS as described. Both MS and MS/MS spectra will be acquired in both data-dependent and data-directed modes. In the data-dependent mode, 10 MS/MS spectra will be obtained for each high resolution FT-MS scan each second over a 120 min chromatographic analysis. Modified peptides will be identified using accurate mass driven selected ion extraction. The peptide sequence and site(s) of modification will be confirmed from the tandem mass spectra. In data-directed mode, the mass spectrometer will be programmed to acquire MS/MS by accurate masses (m/z values) that correspond to the theoretical values of modified peptides from candidate modifications. Phosphorylation, acetylation, and single residue glycosylation with hexose or O-GlcNAc would result in mass increments of 79.966, 42.011, 162.053, and 203.079, respectively. As described for phosphorylation analysis, all possible sites of modifications can be analyzed using accurate masses determinations from FT-MS measurements.

EXAMPLE 13

Construction and Expression of NAMPT-Flag®and its Secretion by HIB-1B Cells

A C-terminally FLAG®-tagged mouse Nampt (Nampt-FLAG®) cDNA was created using the following forward and reverse primers containing EcoRI sites: SEQ ID NO:2, Nampt forward; SEQ ID NO:6, Nampt-FLAG® reverse. The resulting cDNA was sequenced and encodes a Nampt-FLAG® protein (SEQ ID NO:7).

To create cell lines expressing Nampt-FLAG®, mouse NIH3T3 fibroblasts and mouse HIB-1B preadipocytes were transfected (Superfect, QIAGEN) with pCXN2-Nampt-FLAG® or pCXN2 (vector control). Cells were selected with G418 for 2 weeks (600-700 µg/ml for NIH3T3; 500 µg/ml for HIB-1B) (Invitrogen, CA).

Figure 16A:
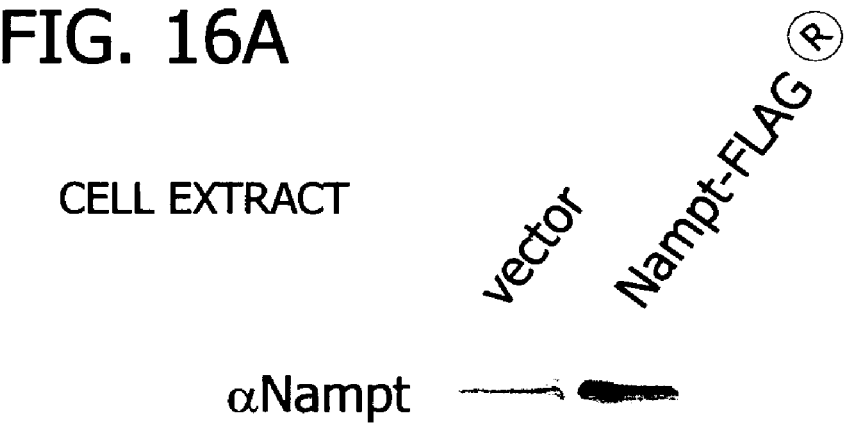
FIG. 16A is an image of a gel confirming the expression of Nampt-FLAG® with both anti-Nampt and anti-FLAG® antibodies in extracts from undifferentiated HIB-1B cells compared to a vector-only control.
Figure 16B:
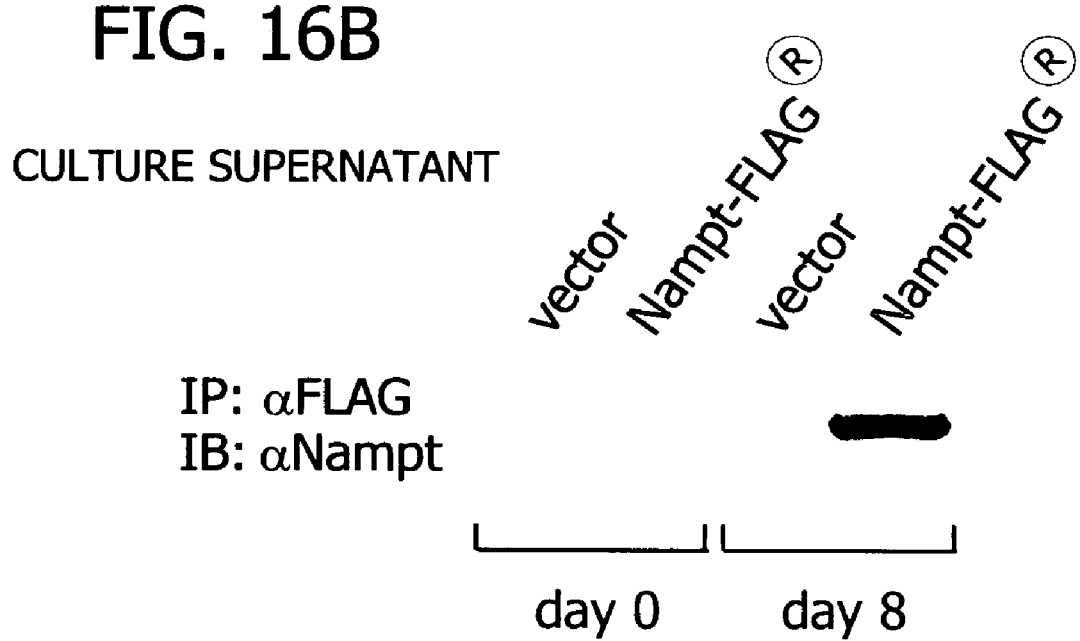
FIG. 16B is an image of a gel showing that the extracellular Nampt-FLAG® protein was detected in culture supernatants when Nampt-FLAG® HIB-1B cells were fully differentiated.
Figure 16C:
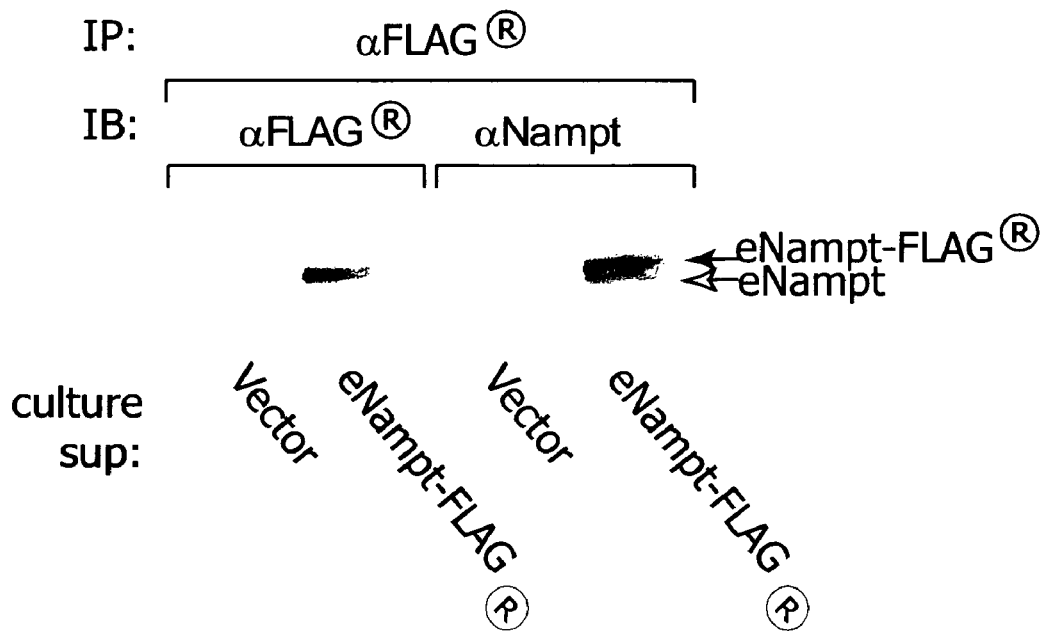
FIG. 16C is an image of a gel showing that extracellular Nampt-FLAG® co-immunoprecipitates with untagged extracellular Nampt from culture supernatants. The culture supernatants of the vector-transfected cells were used as a control.

To verify if Nampt-FLAG® could be secreted as the endogenous Nampt, HIB-1B was differentiated as described in Example 5. Cell extracts and culture supernatants (8 ml) were collected, and Nampt-FLAG® was immunoprecipitated overnight with anti-FLAG®-M2-conjugated beads (Sigma, MO) and analyzed by Western Blot with rabbit polyclonal anti-Nampt or rabbit polyclonal anti-FLAG® (Sigma, MO). The expression of Nampt-FLAG® was confirmed with both anti-Nampt and anti-FLAG® antibodies in extracts from undifferentiated HIB-1B cells compared to a vector-only control (see FIG. 16A). The extracellular Nampt-FLAG® protein was detected in culture supernatants when Nampt-FLAG® HIB-1B cells were fully differentiated (see FIG. 16B), similar to the untagged extracellular Nampt (see FIG. 16A). Interestingly, when the extracellular Nampt-FLAG® band was resolved, it was noted that untagged extracellular Nampt co-immunoprecipitated with extracellular Nampt-FLAG® (see FIG. 16C), suggesting that extracellular Nampt forms a dimer (or oligomer), as seen in the crystal structure (see FIG. 15).

For immunoprecipitation of intracellular Nampt, whole cell extracts were prepared with ice-cold immunoprecipitation (IP) buffer (phosphate buffer saline [pH 7.4], 0.5% NP-40, 1 mM EDTA, 1 mM NaF, 10 µM Trichostatin A, 10 mM nicotinamide, 0.5 mM DTT, protease inhibitor cocktail (Roche)) and mixed with agarose beads conjugated with the mouse monoclonal M2 anti-FLAG antibody (F2426, Sigma) for 3-4 hours at 4° C. For immunoprecipitation of extracellular Nampt, HIB-1B culture supernatants were collected after incubating differentiated HIB-1B cells overnight with DMEM without fetal bovine serum but supplemented with 1 µg/ml insulin and 1 nM triodothyronine, filtered through a 0.22-µm PES membrane, concentrated with Amicon Ultra-15 columns (Millipore, MA), and mixed with anti-FLAG beads for 3-4 hours at 4° C. Immunoprecipitates were washed twice with the IP buffer and twice with PBS.

Immunoprecipitates on anti-FLAG beads were incubated in enzymatic reaction buffer (50 mM Tris-HCl (pH8.5), 100 mM NaCl, 0.25 mM Nicotinamide, 10 mM $MgSO_4$, 1.5% Ethanol, 0.5 mM PRPP, 2.0 mM ATP) for 55 min at 37° C. After this reaction, mouse recombinant nicotinamide mononucleotide adenylyltransferase and yeast alcohol dehydrogenase (Sigma) were added at 10 µg/ml as the final concentration for each, and the mixture was incubated for 5 min at 37° C. Supernatants were then collected by spinning down anti-FLAG beads, and autofluorescence of NADH was measured in a Perkin Elmer LS 50B fluorometer (excitation: 340 nm; emission: 460 nm). Immunoprecipitates bound on anti-FLAG beads were extracted with Laemmli's sample buffer, boiled for 5 minutes, and analyzed by Western blotting with anti-Nampt antibodies. The amounts of Nampt used for enzymatic reactions were quantitated compared to the standards of mouse recombinant Nampt.

Figure 16D:
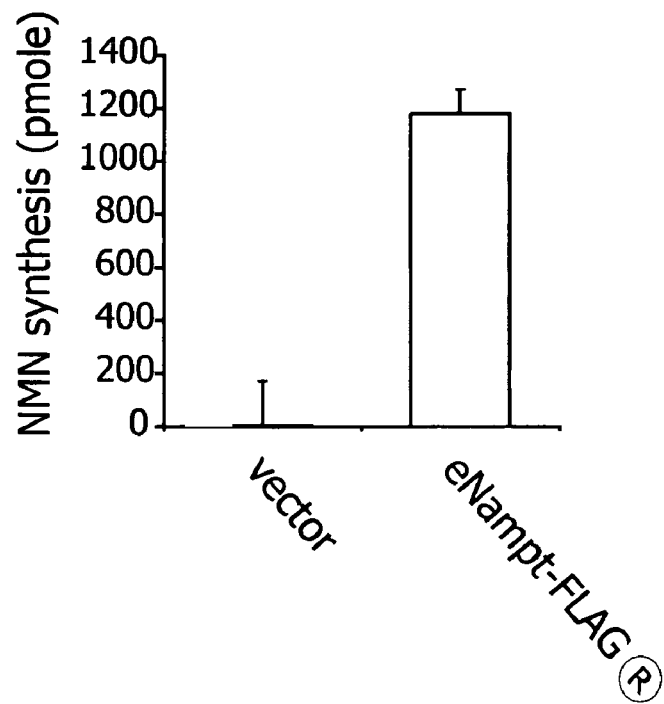
FIG. 16D is a graph showing that the extracellular Nampt-FLAG® protein immunoprecipitated from culture supernatants of differentiated Nampt-FLAG HIB-1B cells has Nampt enzymatic activity.
Figure 16E:
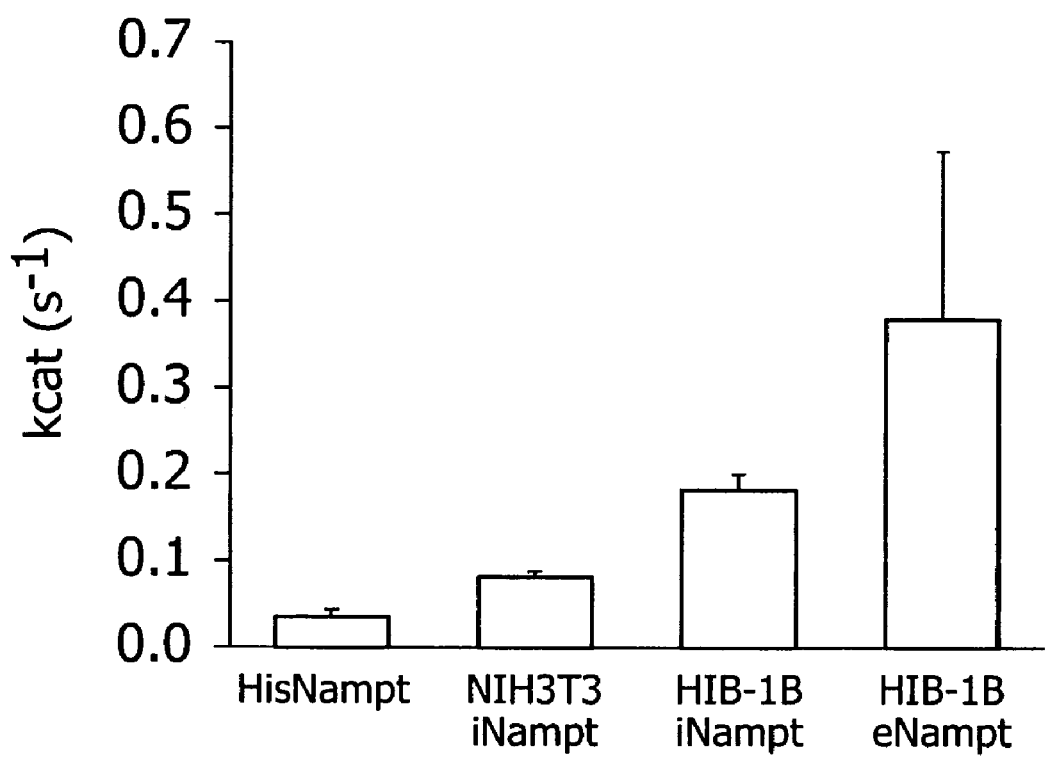
FIG. 16E is a graph showing the kcat values of bacterially produced His-tagged recombinant Nampt and intra- and extracellular Nampt-FLAG® from NIH3T3 and differentiated HIB-1B cells. Results were calculated by measuring nicotinamide mononucleotide (NMN) synthesis and quantifying the amount of each Nampt by Western Blotting. Results are presented as mean±SD (n=7 for His-tagged Nampt, 3 for intracellular Nampt from NIH3T3, 6 for intracellular Nampt from HIB-1B, and 4 for extracellular Nampt from HIB-1B), and all differences in pair-wise comparisons are statistically significant with the Student's t test (p<0.05) (See Example 13).

The immunoprecipitates from the HIB-1B culture supernatants were subjected to enzyme-coupled fluorometric assays (see Revollo et al., J. Biol. Chem., (2004)279, 50754-50763) to compare enzymatic activity of the intracellular and extracellular forms of Nampt. Robust activity was detected from the immunoprecipitated extracellular Nampt-FLAG® protein, while immunoprecipitates from culture supernatants of the backbone vector transfected HIB-1B cells showed no activity (see FIG. 16D). The Nampt enzymatic activity of the bacterially produced recombinant Nampt and the intracellular Nampt-FLAG® immunoprecipitated from HIB-1B and NIH3T3 cellular extracts were also measured and their $k_{cat}$ values calculated (see FIG. 16E). Surprisingly, the extracellular Nampt-FLAG® secreted from differentiated HIB-1B cells showed a significantly higher $k_{cat}$ value (0.380/s) than recombinant Nampt (0.035/s, ~11-fold), intracellular Nampt-FLAG® from NIH3T3 cells (0.082/s, ~5-fold), and intracellular Nampt-FLAG® from differentiated HIB-1B cells (0.182/s, ~2-fold) (see FIG. 16E). It should be noted that intracellular Nampt-FLAG® from differentiated HIB-1B cells also showed higher enzymatic activity than intracellular Nampt-FLAG® from NIH3T3 cells that do not produce extracellular Nampt (see FIG. 16E). It is believed that a post-translational modification may be responsible for the altered enzymatic activity of extracellular Nampt produced by brown adipocytes. The treatment of extracellular Nampt from HIB-1B culture supernatants with calf intestinal phosphatase (CIP) did not change its enzymatic activity, suggesting that the modification in extracellular Nampt is not a simple phosphorylation. Despite the extensive mass spectrometric analysis of extracellular Nampt, the precise nature of the modification is currently unknown. Taken together, these findings provide strong evidence that Nampt functions as an NAD biosynthetic enzyme both intra- and extracellularly.

EXAMPLE 14

Extracellular NAMPT Secretion Assays

It has been speculated that the secretion of extracellular Nampt/PBEF/visfatin might be due to cell lysis or death (Hug et al., Science, (2005) 307, 366-367; Stephens et al., Curr. Opin. Lipidol., (2006) 17, 128-131). To determine if extracellular Nampt was positively secreted or a product of cell death or lysis, a C-terminally FLAG®-tagged mouse dihydrofolate reductase (pCXN2-Dhfr-FLAG®) and a C-terminally FLAG®-tagged bovine preprolactin (pCXN2-Ppl-FLAG® as negative and positive secretion controls, respectively, were constructed. HIB-1B preadipocytes were transfected with these constructs and selected with G418 as described in Example 13.

HIB-1B cells expressing Nampt-FLAG, Dhfr-FLAG, and Ppl-FLAG were differentiated to mature adipocytes (day 8) in 10-cm dishes, and their cell extracts were collected and immunoprecipitated as described above. Culture supernatant (~8 ml) were collected and immunoprecipitated overnight at 4° C. with anti-FLAG antibody-conjugated beads, washed twice with PBS, and analyzed by Western Blot with rabbit polyclonal anti-FLAG antibody (Sigma, MO).

Figure 17A:
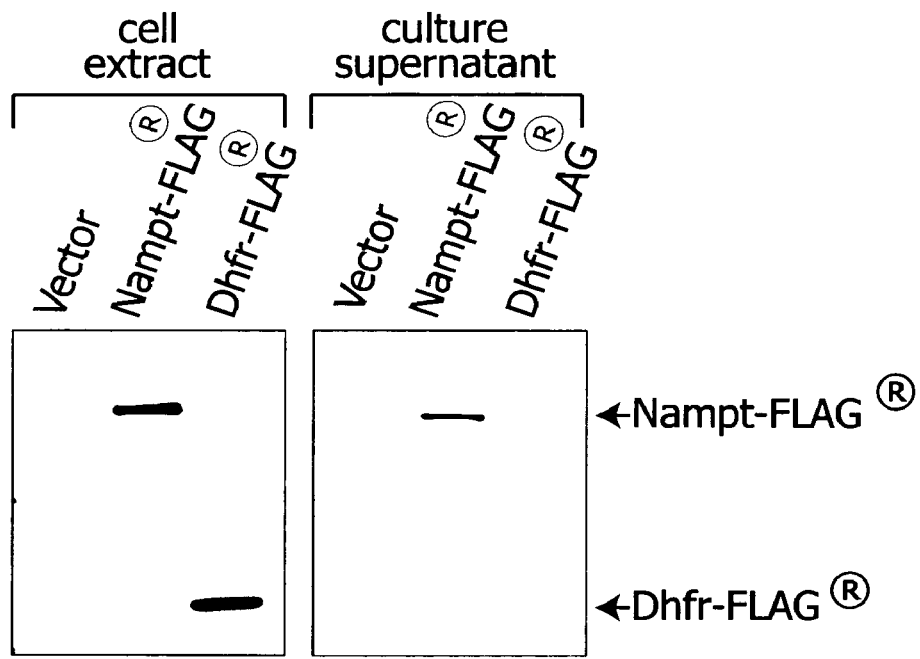
FIG. 17A, 17B, and 17C are images of gels showing that extracellular Nampt is positively secreted through a non-classical secretory pathway in differentiated HIB-1B brown adipocytes. As well as the HIB-1B cell line that expresses Nampt-FLAG®, two other HIB-1B cell lines that express C-terminally FLAG®-tagged mouse dihydrofolate reductase (Dhfr) and bovine preprolactin (Ppl) were established.
Figure 17B:
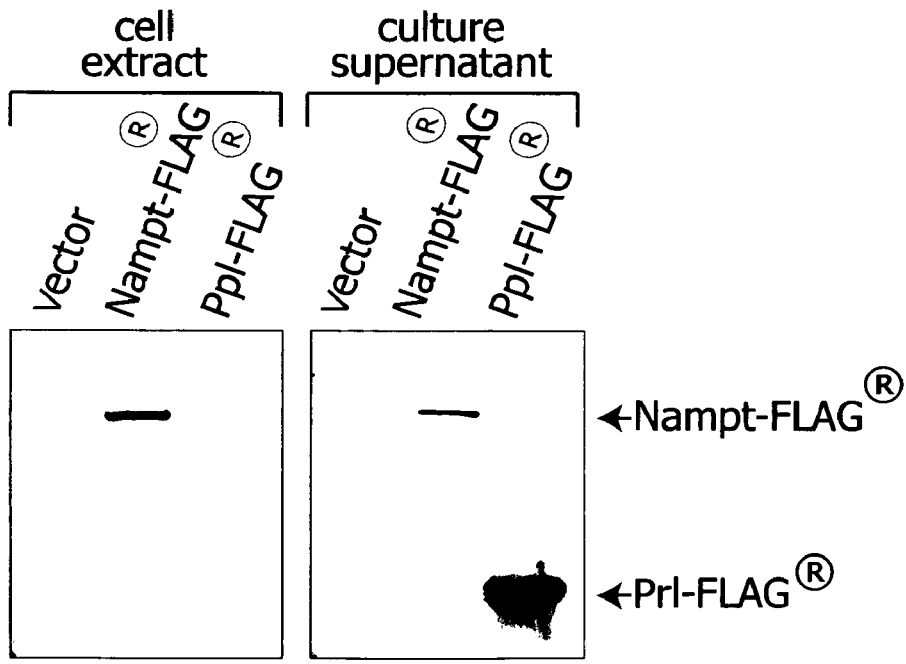

Dhfr-FLAG® was detected in cell extracts but not at all in culture supernatants (see FIG. 17A), while prolactin-FLAG® (Prl-FLAG®) was mainly detected in supernatants (see FIG. 17B). In this condition, robust levels of Nampt were detected in both cell extracts and supernatants, demonstrating that the existence of extracellular Nampt is not due to cell lysis or cell death.

Figure 17C:
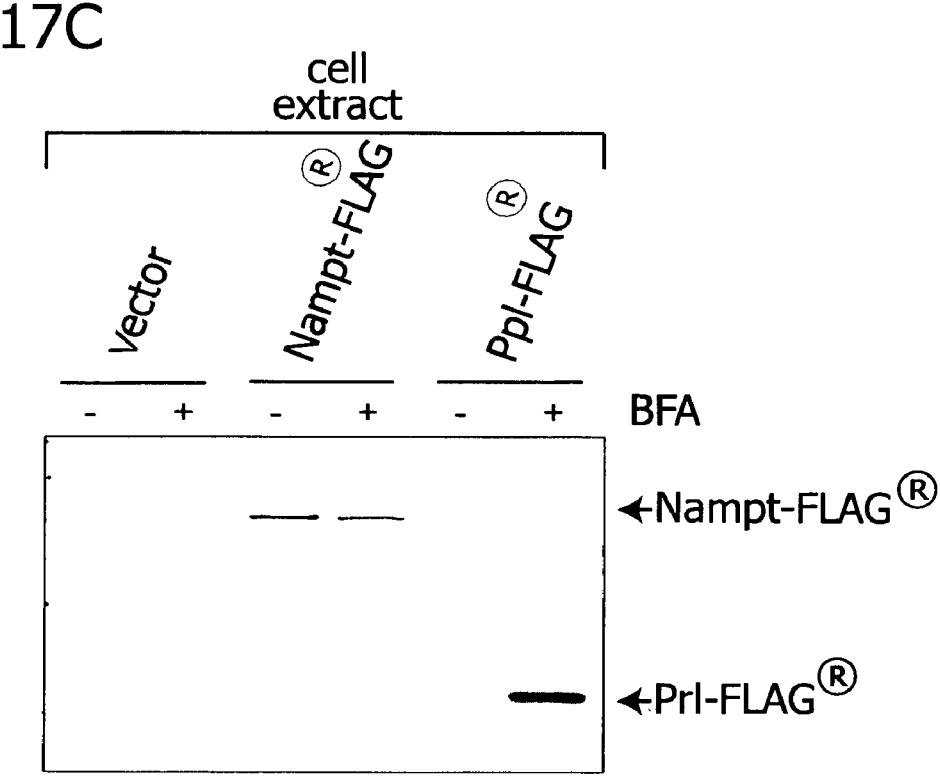
Figure 17D:
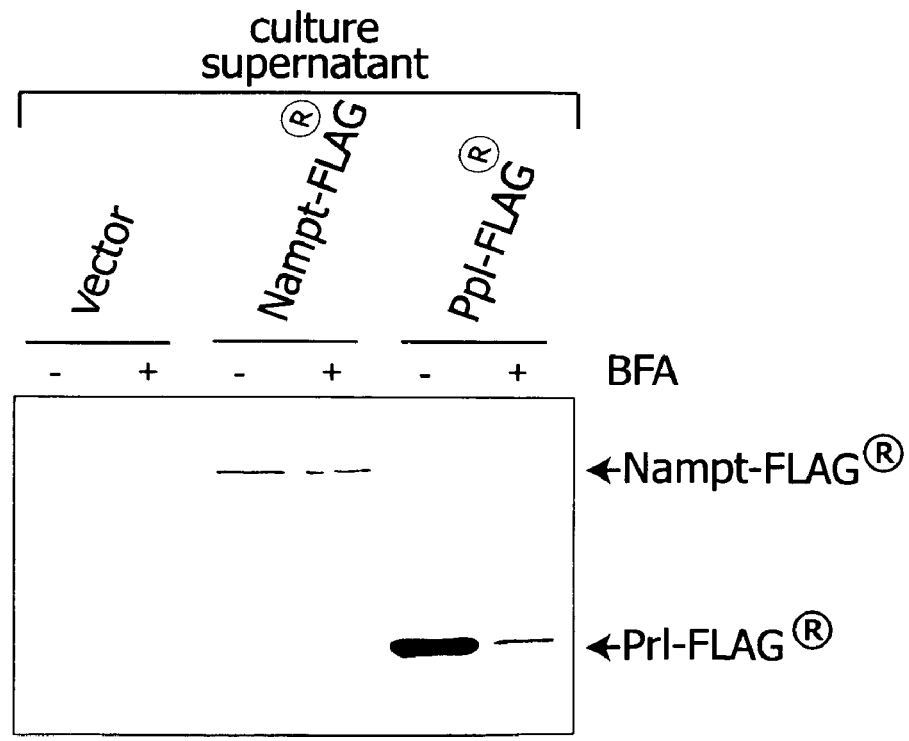

Brefeldin A (BFA), a potent inhibitor of the classical secretory pathway, was added to examine if Nampt-FLAG® is secreted through the ER-Golgi system. Fully differentiated HIB-1B adipocytes (day 8) were treated with BFA (0.5 ug/ml, Sigma, MO) for 12 hours, and cell extracts and culture supernatants were collected and analyzed as described above. While eNampt levels in supernatant were not affected by BFA, the secretion of Prl-FLAG was significantly inhibited by BFA so that the level of Ppl-FLAG in cell extracts increased (see FIG. 17C). This finding suggests that eNampt is not secreted through a classical Golgi-ER system but through some non-classical secretory pathway.

Figure 18A:
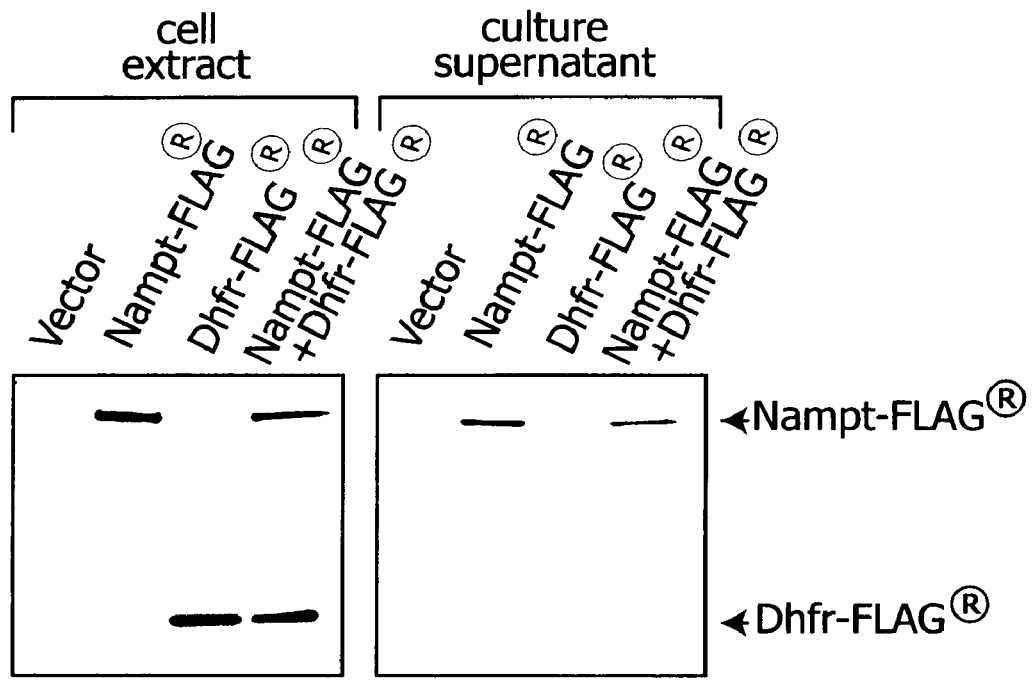
FIGS. 18A, 18B, and 18C are images of gels showing that extracellular Nampt is also positively secreted by Chinese hamster ovary (CHO) cells.
Figure 18B:
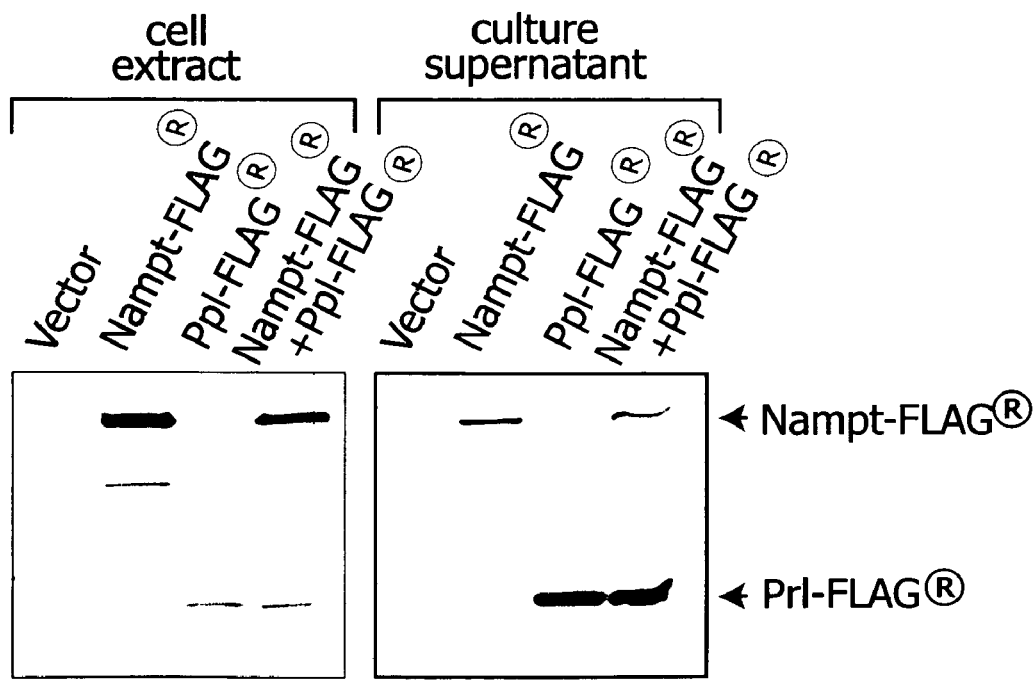
Figure 18C:
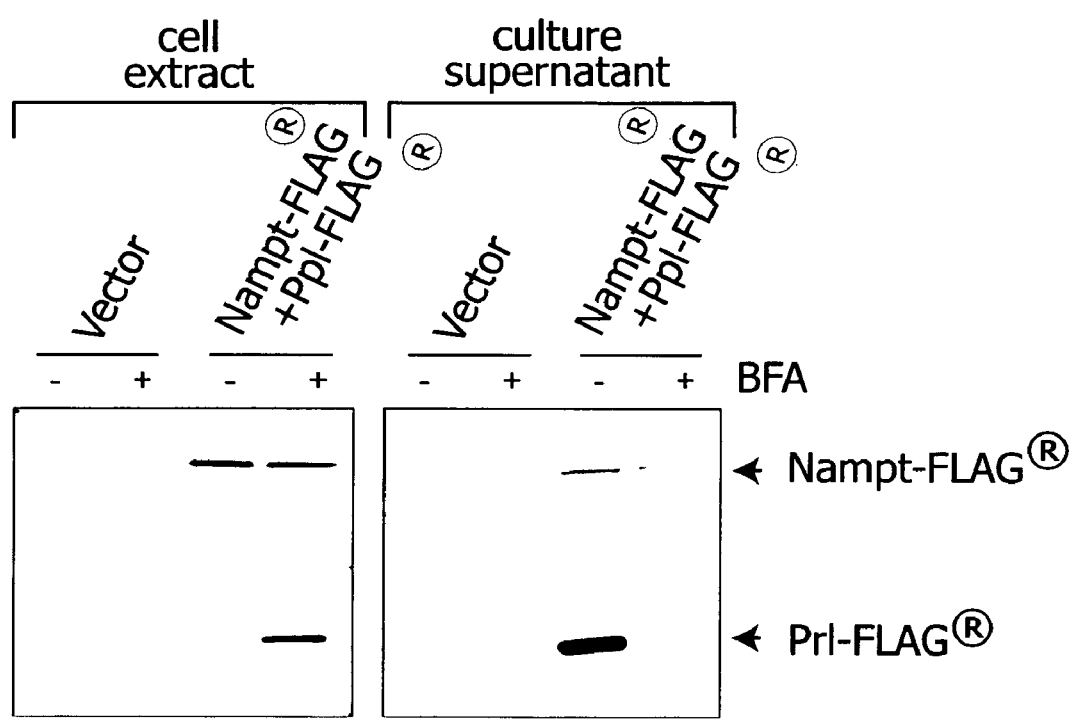

To confirm these results with a different cell line, Chinese hamster ovary (CHO) cells at 50-60% confluency in 6-cm dishes were transfected (SuperFect, QIAGEN) with empty-vector plasmid (pCXN2), Dhfr-FLAG® (pCXN2-Dhfr-FLAG®), Ppl-FLAG®) (pCXN2-Ppl-FLAG®), and Nampt-FLAG® (pCXN2-Nampt-FLAG®). Cell extracts and culture supernatants were collected 48 hours after transfection, and subjected to immunoprecipitation with anti-FLAG® antibody-conjugated beads as described above, and analyzed by Western Blot with rabbit polyclonal anti-FLAG® antibody (Sigma, MO). Cells were also treated with BFA as described above. As shown in FIGS. 18A, 18B, and 18C, Dhfr-FLAG® is exclusively localized intracellularly, Prl-FLAG® is mainly secreted, but Nampt is localized both intra- and extracellularly. Again, the secretion of Prl-FLAG® was significantly inhibited by BFA, but the secretion of extracellular Nampt was unaffected. Taken together, these results clearly demonstrate that extracellular Nampt is indeed positively secreted by certain cells (e.g., adipocytes and CHO cells).

EXAMPLE 15

NAMPT-Deficient Heterozygous (NAMPT$^{+/-}$) Mice

Figure 19A:
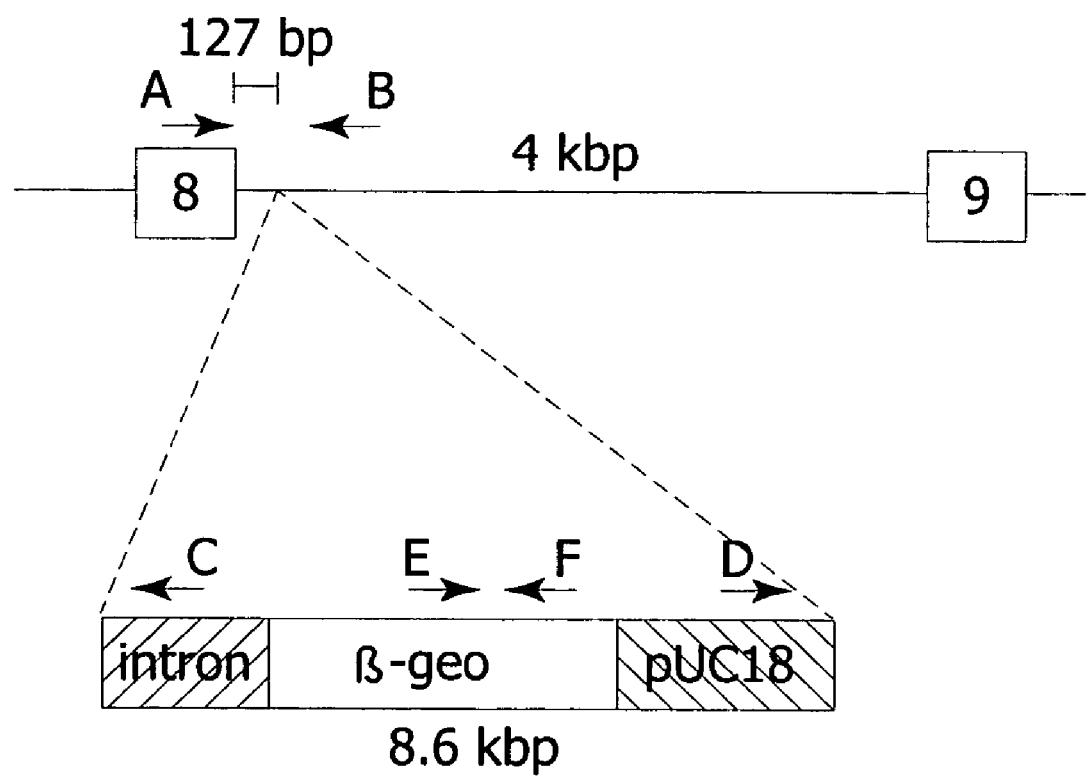
FIGS. 19A, 19B, and 19C are images and gels describing the preparation of Nampt-deficient heterozygous (Nampt$^{+/-}$) mice.
Figure 19B:
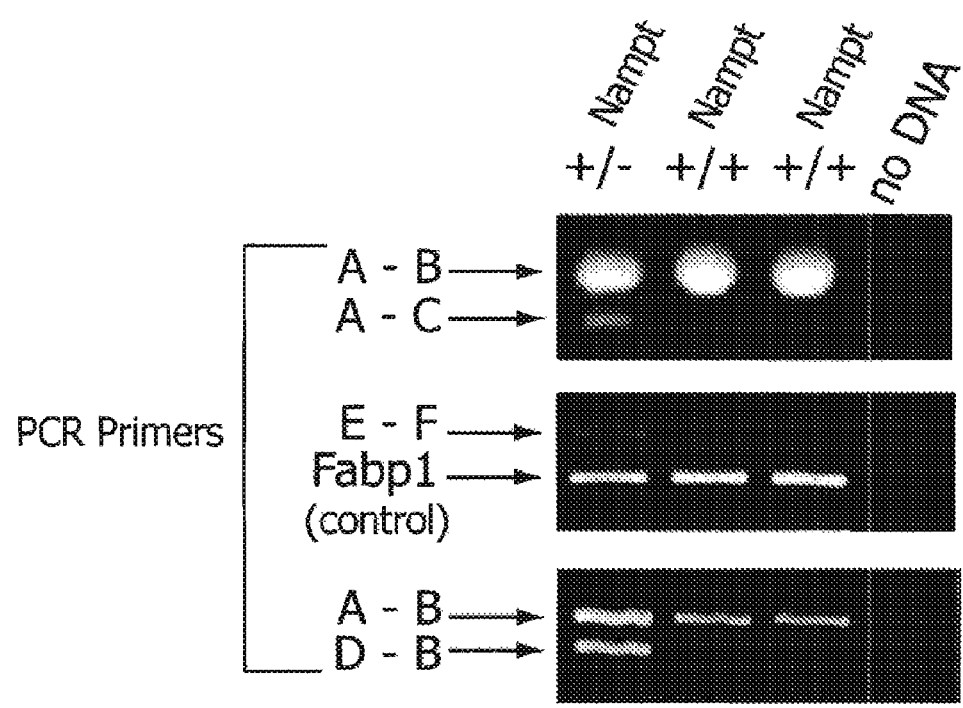

Nampt$^{+/-}$ mice were produced using a 129/Ola ES cell line created and designated RRT307 (Bay Genomics, San Francisco, Calif.). In this RRT307 ES cell line, RACE data provided by Bay Genomics indicated that the β-geo exon-trap construct was inserted between exon 8 and 9 of the Nampt gene. To map the exact site of the exon trap insertion, tail genomic DNA was isolated from adult Nampt$^{+/-}$ mice and PCR was performed with primers A and C for the exon trap (SEQ ID NO:8 and SEQ ID NO:9, respectively), and A and B for a genomic control (SEQ ID NO:8 and SEQ ID NO:10, respectively). Sequencing the PCR product of the PCR product A-C (SEQ ID NO:11) located the insertion site 127 bp downstream of exon 8. To verify these results, PCR with primers B and D (SEQ ID NO: 10 and SEQ ID NO:12, respectively) was also performed. Sequencing of the PCR product D-B (SEQ ID NO: 13) confirmed the insertion site. The β-geo fragment was also detected by primers E and F (SEQ ID NO: 14 and SEQ ID NO: 15, respectively). See FIG. 19B.

Figure 19C:
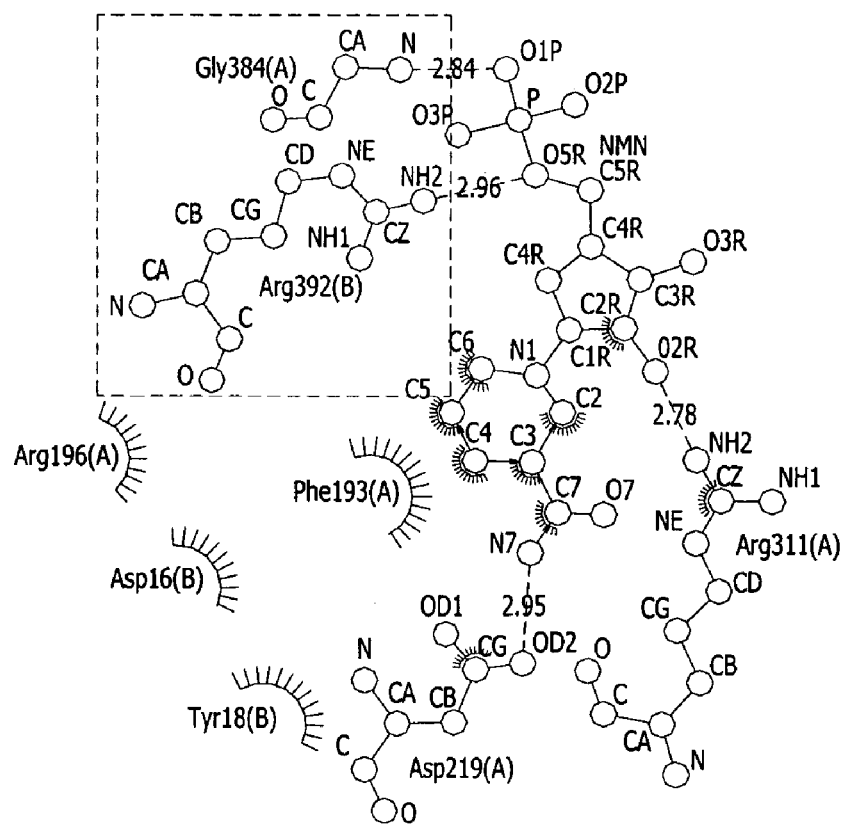
Figure 20A:
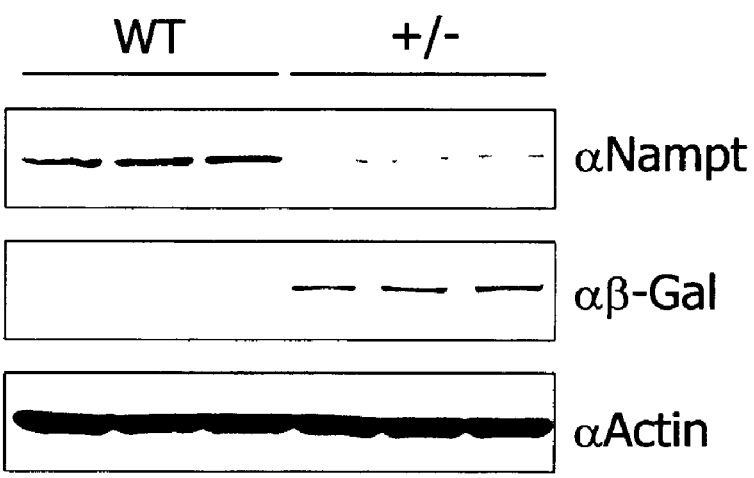
FIGS. 20A, 20B, 20C, and 20D are images of gels showing Nampt expression levels in heart, kidney, liver, and brown adipose tissue of Nampt$^{+/-}$ and Nampt$^{+/+}$ (wild type (WT)) mice. (See Example 16).
Figure 20B:
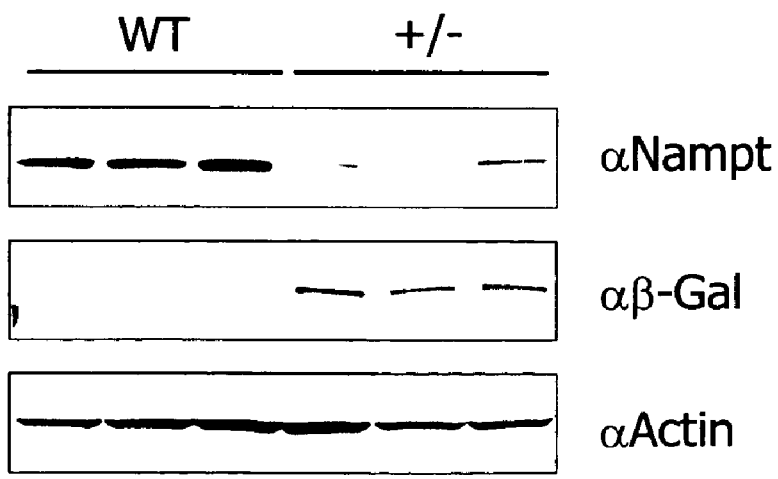
Figure 20C:
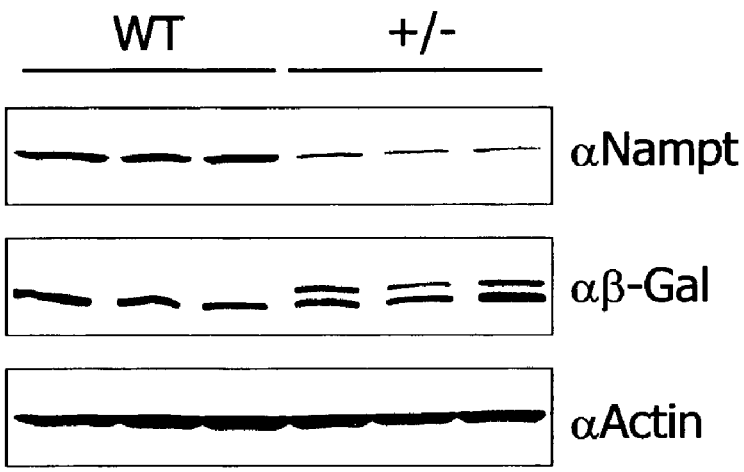
Figure 20D:
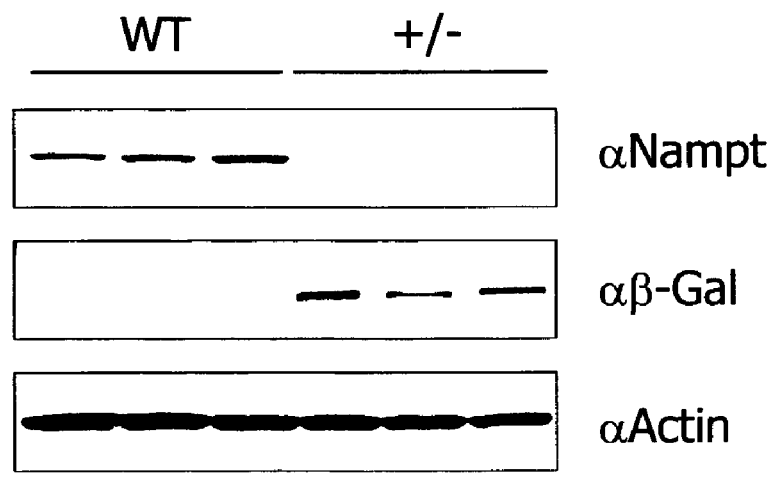

As a result of the insertion, C-terminal 128 amino acids are truncated so that a ~190 kDa fusion protein of Nampt and β-geo is produced (see FIG. 19C). Because the truncated portion includes critical amino acids that contribute to the Nampt enzymatic catalytic site, such as Gly384 and Arg392 (see Wang et al., Nat. Struct. Mol. Biol., (2006) 13, 661-662); see also FIG. 19C), the fusion protein should be enzymatically different.

Nampt$^{+/-}$ mice were backcrossed to the C57BL/6 background at least six times. Homozygous mice were found to be embryonically lethal, which was consistent with the early embryonic lethality of visfatin-deficient homozygous mice reported by Fukuhara et al. (Science, (2005) 307, 426-430). Nampt$^{+/-}$ mice where obtained with the expected Mendelian ratios and developed normally. F7 Nampt$^{+/-}$ and Nampt$^{+/+}$ siblings were used in the following experiments.

EXAMPLE 16

Analysis of NAMPT$^{+/-}$ Mice

Nampt$^{+/-}$ males and Nampt$^{+/+}$ littermates at 3-4 months of age were sacrificed by carbon dioxide asphyxiation. Heart, liver, kidney, and BAT were surgically obtained, homogenized, and boiled in Laemmli's sample buffer. Proteins were quantitated with the Bradford assay (BioRad, CA), and each tissue extract (45 μg) was separated using a 7.5% SDS-PAGE gel, transferred onto Immobilon-P membranes (Millipore, Mass.), and analyzed by Western blotting with primary antibodies described in Example 3. Additionally, to detect the Nampt-β-geo fusion protein, a mouse monoclonal anti-β-gal was employed (Roche).

In Nampt$^{+/-}$ mice, a significant reduction of intracellular Nampt levels in heart, liver, kidney, and brown adipose tissue (BAT) as compared to those in Nampt$^{+/+}$ (WT) mice (see FIGS. 20A, 20B, 20C, and 20D). The Nampt-β-geo fusion protein was also detected, but only in Nampt$^{+/-}$ mice (see FIGS. 20A, 20B, 20C, and 20D). Therefore, these Nampt-deficient heterozygous mice provide an important tool to elucidate the physiological significance of Nampt-mediated systemic NAD biosynthesis in glucose metabolism regulation.

EXAMPLE 17

NAMPT+/- Mice and Blood Glucose Regulation

Figure 21A:
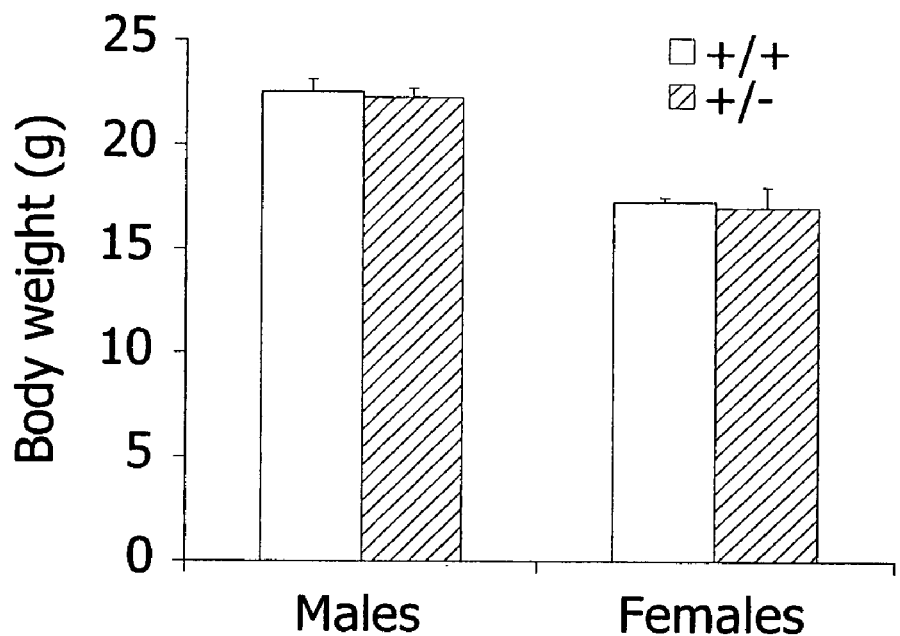
FIGS. 21A, 21B, 21C, 21D, 21E, and 21F are a series of graphs showing that Nampt$^{+/-}$ mice show moderately impaired glucose tolerance and reduced glucose-stimulated insulin secretion.

As noted above, Nampt$^{+/-}$ mice did not show any gross abnormality. Body weights of Nampt$^{+/-}$ mice at 3 months of age did not differ from those of Nampt$^{+/+}$ siblings (see FIG. 21A).

Figure 21B:
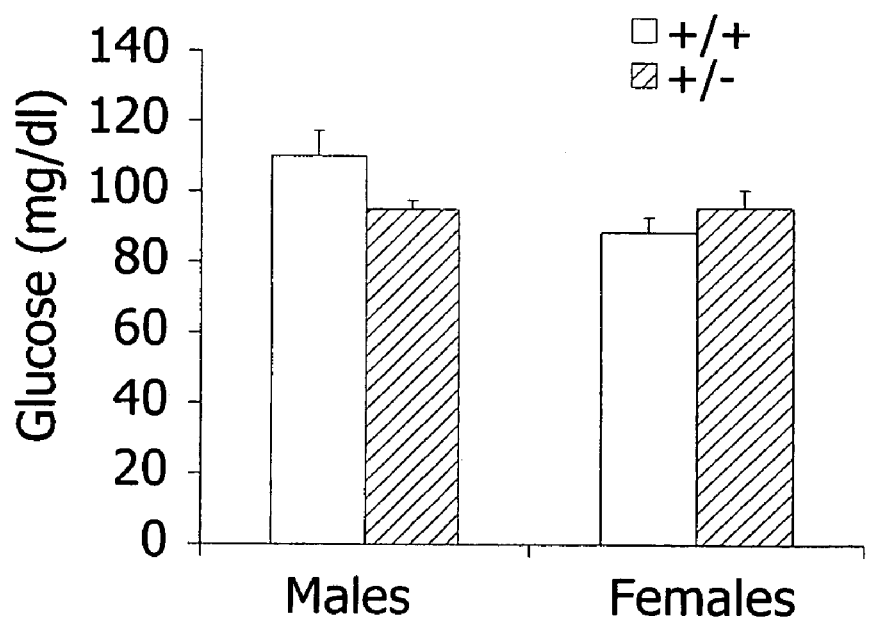

Glucose levels were determined using the Accu-Chek II glucometer (Roche Diagnostics) with blood collected from the tail vein. For determining insulin levels, blood was collected from the tail vein into chilled heparinized capillary tubes, and plasma was separated by centrifugation and stored at −80° C. Insulin levels were determined on 10 μl aliquots using rat insulin ELISA kits with mouse insulin standards (ALPCO). Fed and fasted glucose levels are also similar between Nampt$^{+/-}$ and Nampt$^{+/-}$ mice (see FIG. 21B).

a. Intraperitoneal Glucose Tolerance Tests (IPGTTs) and Insulin Tolerance Tests (ITTs)

Intraperitoneal glucose tolerance tests (IPGTTs) were conducted with a does of 3 g dextrose/kg body weight on Nampt$^{+/-}$ and Nampt$^{+/+}$ siblings. For the IPGTTs, after mice were injected with PBS or NMN (500 mg/kg body weight) and fasted for 12-14 hours, dextrose (3 g/kg body weight) was injected intraperitoneally, and blood glucose levels were measured at 0, 15, 30, 60, and 120 min after injection. Plasma was also collected at 0 and 30 min time points after glucose injection and submitted for insulin measurements to the Washington University RIA Core facility. For the ITTs, after female mice were fasted for 4 hours, human insulin (0.75 U/kg body weight) (Lilly) was injected intraperitoneally to these mice, and blood glucose levels were measured at 0, 15, 30, 45, and 60min after insulin injection.

Figure 21C:
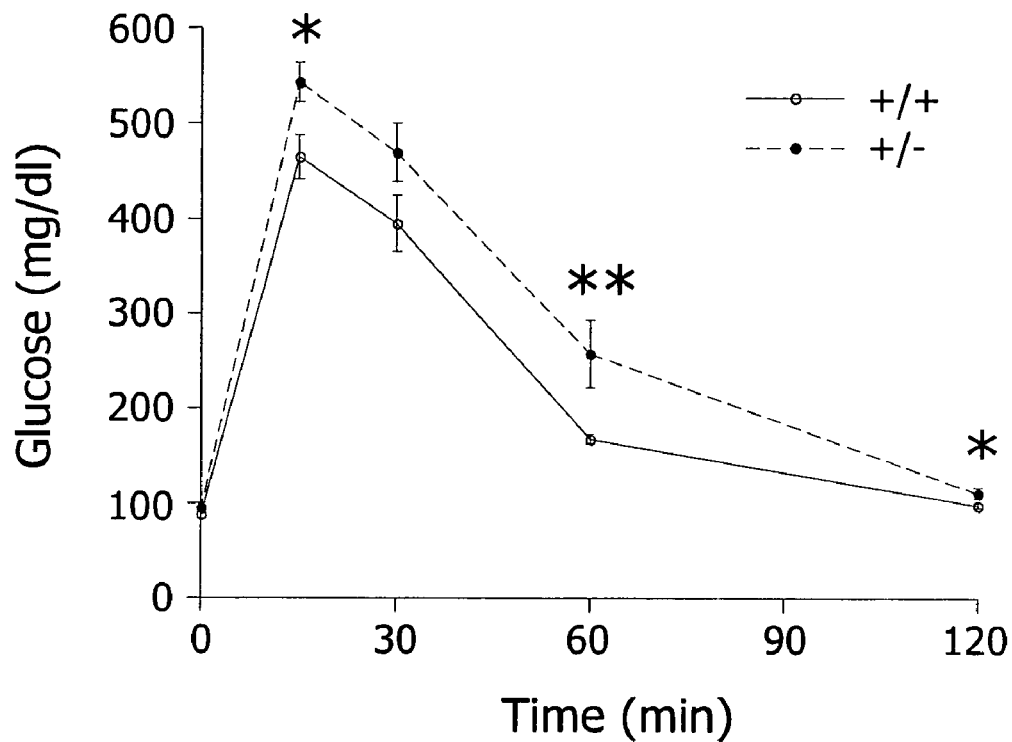
Figure 21D:
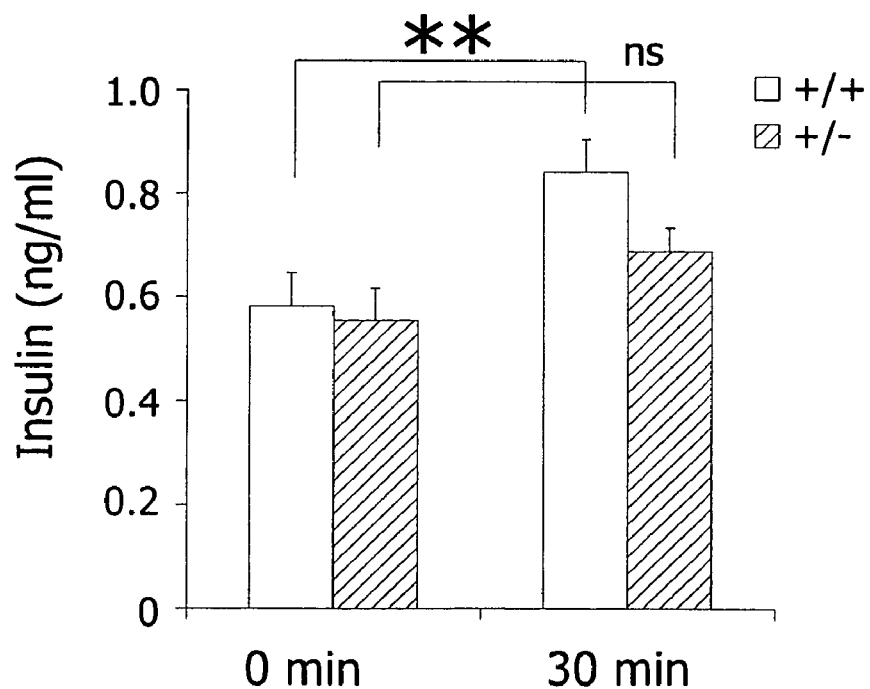
Figure 21E:
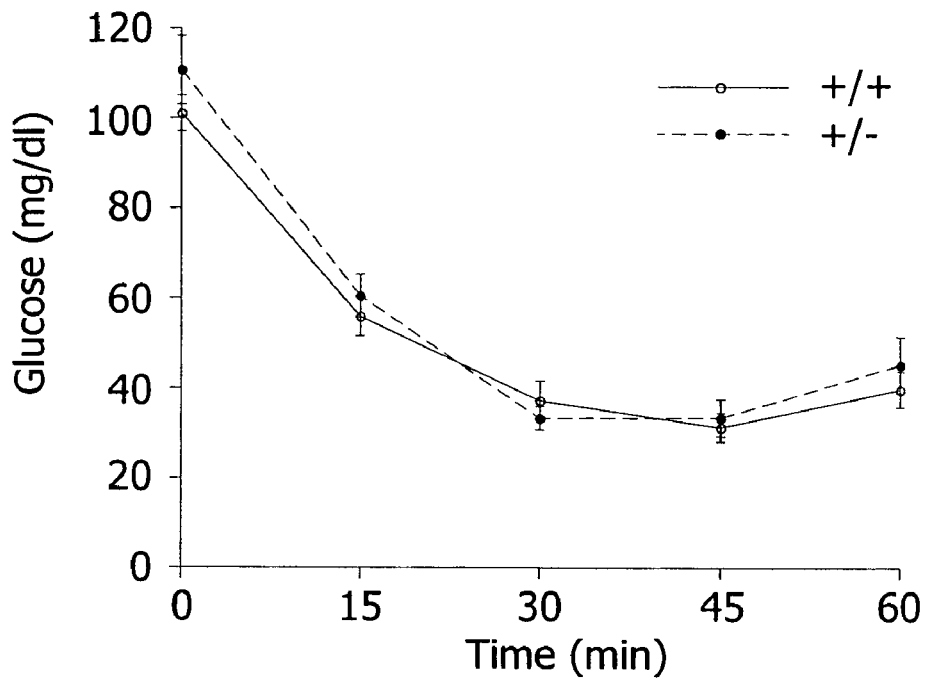

Interestingly, Nampt$^{+/-}$ female mice showed modestly impaired glucose tolerance compared to Nampt$^{+/+}$ mice (see FIG. 21C), while males did not show this phenotype (data not shown). Plasma insulin levels in Nampt$^{+/-}$ and Nampt$^{+/+}$ female mice at 0 and 30 min time points in IPGTTs were also measured. While Nampt$^{+/+}$ mice increased insulin secretion in response to glucose stimulation, Nampt$^{+/-}$ mice did not show a significant increase in insulin secretion at 30 min time point (see FIG. 21D). In the ITTs, no difference was detected between Nampt$^{+/-}$ and Nampt$^{+/+}$ mice (see FIG. 21E). These results suggest that even the haplodeficiency of Nampt significantly affects glucose-stimulated insulin secretion in pancreatic β cells and causes impaired glucose tolerance in mice. Therefore, insulin secretion from primary islets in response to glucose stimulation between Nampt$^{+/-}$ and Nampt$^{+/+}$ mice was compared.

b. Glucose-Stimulated Insulin Secretion from Primary Islets

Islets were isolated by collagenase digestion. Briefly, pancreata were inflated with isolation buffer (10× HBSS, 10 mM HEPES, 1 mM MgCl$_2$, 5 mM glucose [pH 7.4]) containing 0.375 mg/ml collagenase (Sigma) via the pancreatic duct after clamping off its entry site to the duodenum. The inflated pancreas was then removed, incubated at 37° C. for 12-15 min, and shaken vigorously. Islets were separated from acinar tissue after a series of washes and passages through a 70 um nylon BD Falcon Cell Strainer (BD Biosciences).

Hand-picked islets were cultured overnight in RPMI media containing 1 μM nicotinamide, 5 mM glucose, 2 mM L-glutamine, penicillin/streptomycin, and 10% fetal bovine serum. The islets were then preincubated in oxygenated Krebs-Ringer bicarbonate buffer (KRB) (1 μM nicotinamide, 119 mM NaCl, 4.7 mM KCl, 25 mM NaHCO$_3$, 2.5 mM CaCl$_2$, 1.2 mM MgSO$_4$, 1.2 mM KH$_2$PO$_4$, and 0.25% radioimmunoassay grade BSA) supplemented with 2 mM glucose for 1 hr at 37° C. Islets of similar size were hand-picked into groups of ten islets in triplicate and incubated with 1 ml KRB buffer containing either 2 mM glucose and 20 mM glucose for 1 hr at 37° C.

Figure 21F:
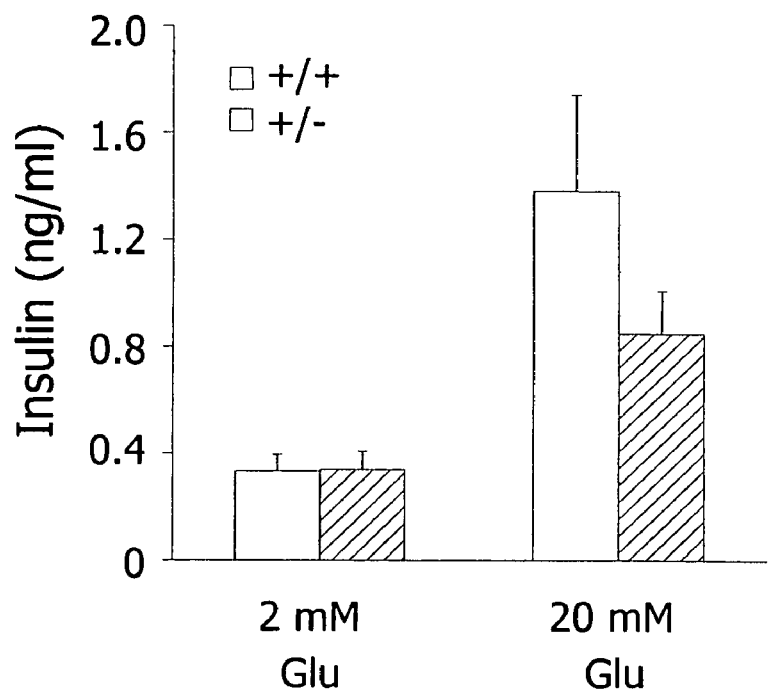

Consistent with the IPGTT results, primary islets isolated from Nampt$^{+/-}$ female mice showed reduced insulin secretion in response to 20 mM glucose compared to those from Nampt$^{+/+}$ mice (see FIG. 21F).

The results obtained from the Nampt$^{+/-}$ mice largely contradict those reported by Fukuhara et al., (Science, (2005) 307, 426-430). First, no significant increases were detected in fed and fasted glucose levels in Nampt$^{+/-}$ mice compared to those in Nampt$^{+/+}$ mice. Second, while Nampt$^{+/-}$ male mice were reported to show marginally impaired glucose tolerance by Fukuhara et al., Nampt$^{+/-}$ females, instead of males, showed moderately but significantly impaired glucose tolerance in the Example 17 IPGTTs. Third, importantly, while there was no assessment of glucose-stimulated insulin secretion by Fukuhara et al., these experiments found that both Nampt$^{+/-}$ mice and islets have a defect in glucose-stimulated insulin secretion. Given that extracellular Nampt/PBEF/visfatin also functions as a robust NAD biosynthetic enzyme extracellularly and also that the Nampt haplodeficiency affects insulin secretion in mice and islets, these results totally contradict the interpretation and the conclusion made by Fukuhara et al., basically raising a serious question against the physiological relevance of the reported insulin-mimetic activity of visfatin.

EXAMPLE 18

Figure 22A:
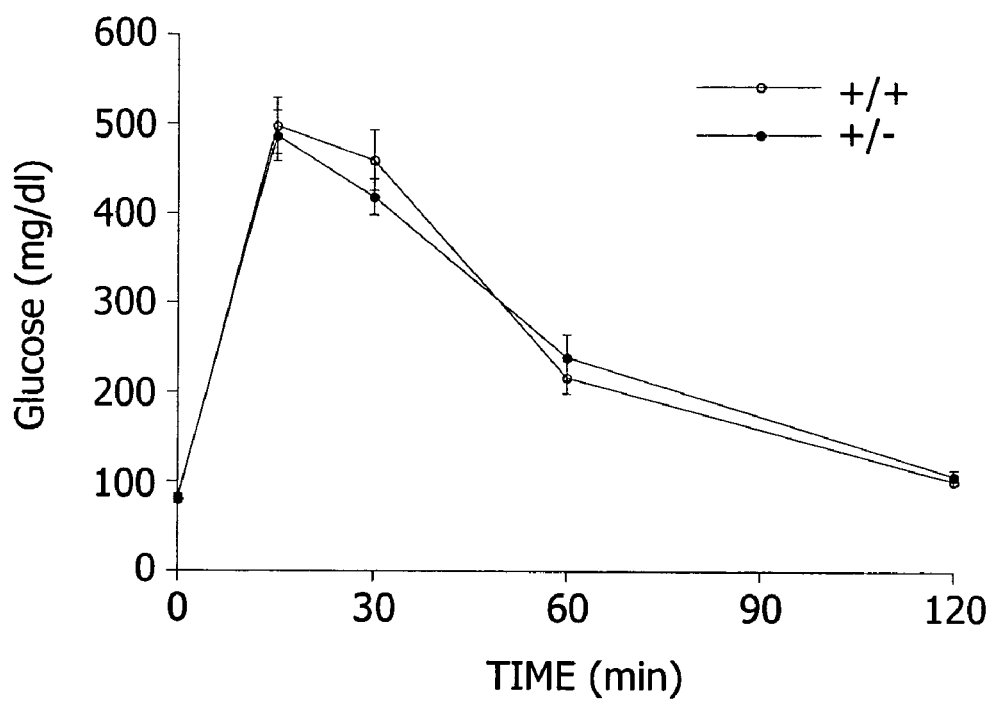
FIGS. 22A, 22B, and 22C are a series of graphs showing that NMN administration can correct the Nampt+/− phenotypes in intraperitoneal glucose tolerance tests (IPGTTs).
Figure 22B:
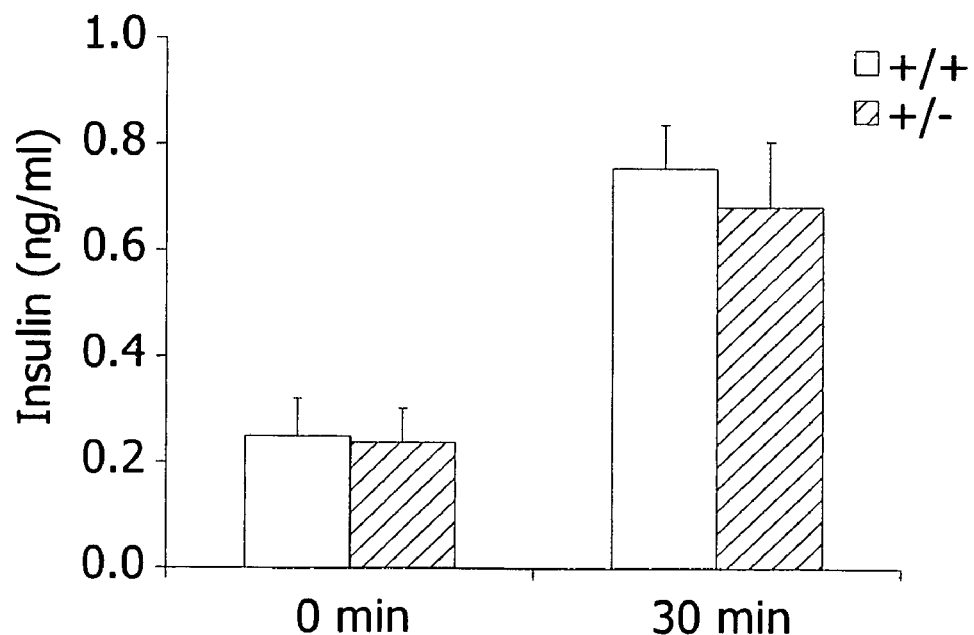
Figure 22C:
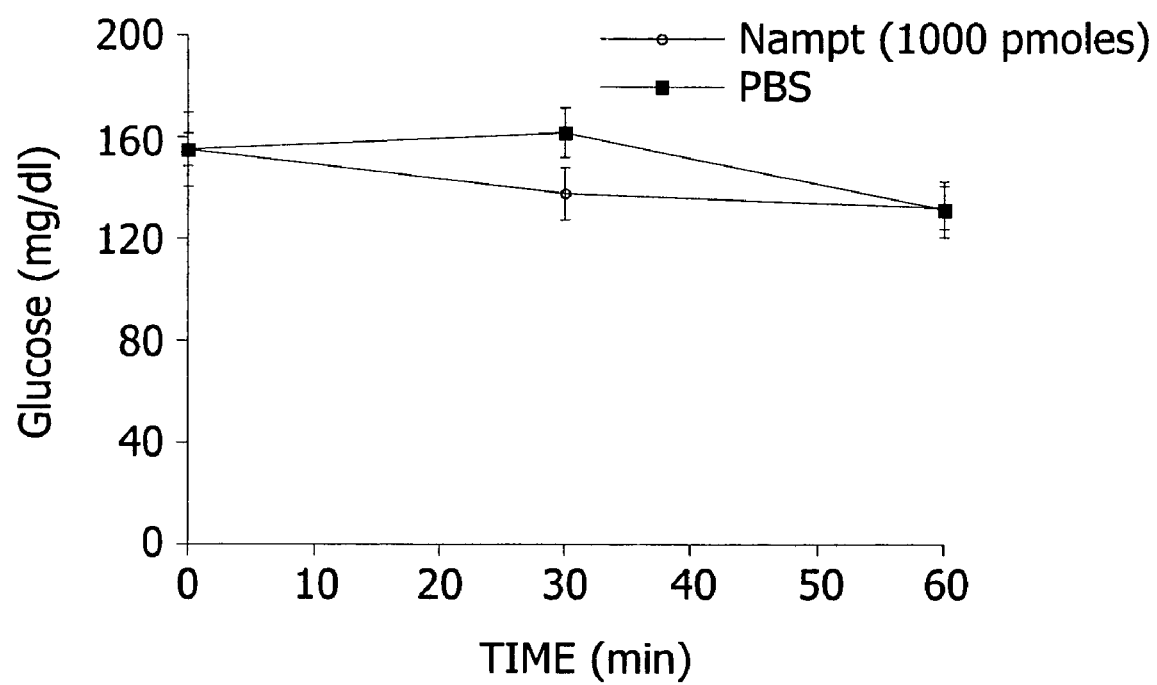

Correction of the NAMPT$^{+/-}$ Phenotypes in IPGTTs by the Administration of NMN If the NAD biosynthetic activity of Nampt is responsible for the phenotypes observed in Nampt$^{+/-}$ mice, the administration of NMN, a product of the Nampt enzymatic reaction, should be able to correct their problems. To test this possibility, the same Nampt$^{+/-}$ mice that were used for IPGTTs were injected with NMN at a dose of 500 mg/kg body weight intraperitoneally ~14 hrs prior to IPGTTs. As a control, PBS was injected to the mice ~14 hrs before conducting previous IPGTTs. Interestingly, after NMN administration, Nampt$^{+/-}$ mice no longer showed impaired glucose tolerance compared to Nampt$^{+/+}$ mice (see FIG. 22A). Additionally, Nampt$^{+/-}$ mice also showed robust insulin secretion similar to that in Nampt$^{+/+}$ mice 30 min after glucose injection (see FIG. 22B). Therefore, these results clearly show that the phenotypes observed in Nampt$^{+/-}$ mice are not due to the insulin-mimetic activity of visfatin but rather due to the NAD biosynthetic activity of Nampt. The results also suggest that NMN could be a therapeutic and/or preventive reagent for metabolic complications caused by the abnormality or the defect in Nampt-mediated systemic NAD biosynthesis. Because these findings completely contradict the conclusion by Fukuhara et al., the reproducibility of the insulin-mimetic activity of this protein was examined. Here, 1000 pmoles of the bacterially produced recombinant protein of mouse His-tagged Nampt were injected intraperitoneally to fed wild type males. Blood glucose levels were monitored with a glucometer at 0, 30, and 60 min time points after injection. Even when a 20-fold higher concentration than reported of the recombinant Nampt was injected, no significant effect on blood glucose levels was noted (see FIG. 22C).

EXAMPLE 19

Figure 23:
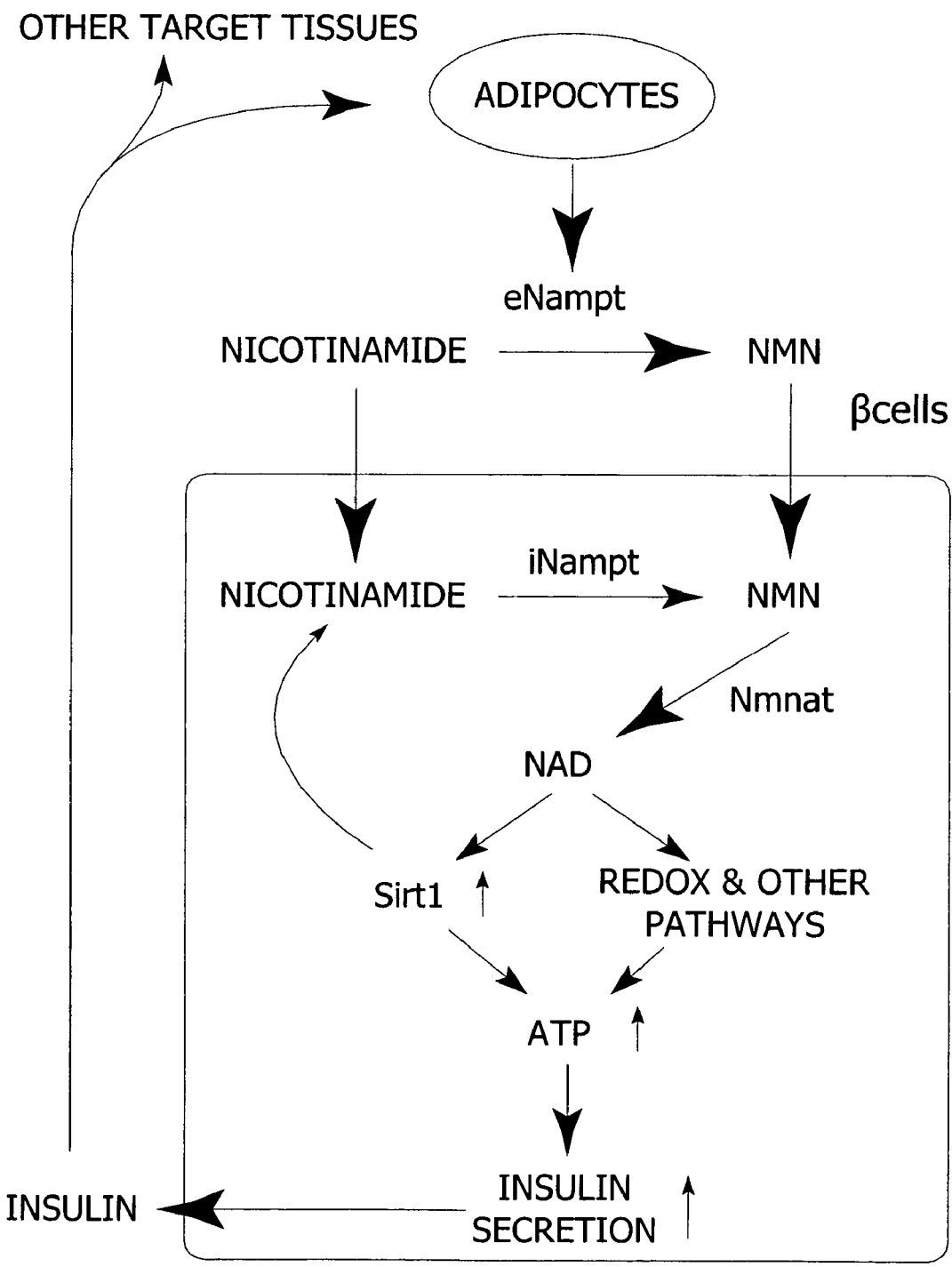
FIG. 23 is a model for the regulation of insulin secretion by Nampt-mediated systemic NAD biosynthesis in pancreatic β-cells. eNampt and iNampt are extracellular Nampt and intracellular Nampt, respectively; NMN and Nmnat are nicotinamide mononucleotide and nicotinamide mononucleotide adenyltransferase, respectively. See Example 19.

A Model of Systemic Regulation of NAD Biosynthesis by Intracellular and Extracellular NAMPT Based on the above description and Examples, a model for the systemic regulation of NAD biosynthesis can be formulated. See FIG. 23. Nicotinamide, absorbed from diet as vitamin B3, is distributed to all organs/tissues through blood circulation. Nicotinamide that gets into cells by diffusion and/or transport is converted to NMN by intracellular Nampt and then to NAD by Nmnat. At or about the same time, a significant fraction of nicotinamide is converted to NMN by extracellular Nampt in blood circulation. NMN is also distributed to organs/tissues through blood circulation and transported into cells. Once NMN is transported to the inside of cells, it is also utilized to synthesize NAD. The distribution of NMN through blood circulation may be particularly important for organs/tissues that do not have sufficient levels of intracellular Nampt to synthesize NAD from nicotinamide, such as the brain and pancreas. Pancreatic β cells appear to be one of the more sensitive cell types to alterations in systemic NAD biosynthesis because even Nampt haplodeficiency affects insulin secretion in response to glucose stimulation in mice and isolated primary islets.

Plasma extracellular Nampt levels are likely regulated by both white and brown adipose tissue. Under normal physiological conditions, white adipose tissue does not secrete high levels of extracellular Nampt, while brown adipose tissue typically does. However, in certain pathophysiological conditions that cause significant changes in adipose tissue mass, structure, or function, such as obesity and type 2 diabetes, adipose tissue might secrete more extracellular Nampt and thereby increase systemic NAD biosynthesis. This response may be particularly important to maintain β cell function in these pathophysiological conditions because peripheral insulin resistance is also worsened in these conditions so that the demands to β cells significantly increase. If so, Nampt-mediated systemic NAD biosynthesis could play an important role in maintaining β cell function in the face of increasing demands in obesity and type 2 diabetes.

In pancreatic β cells, alterations in NAD levels might change activities of important enzymes on metabolic pathways, such as glycolysis or fatty acid oxidation. The same changes in NAD might also change other NAD-dependent enzymes, such as the NAD-dependent deacetylase Sirt1 and the poly-ADP-ribose polymerase PARP. Among them, Sirt1 is a particularly interesting candidate for the following reasons. First, the second important NAD biosynthetic enzyme, Nmnat (or Nmnat-1), is exclusively localized in the nucleus (Araki et al., Science, (2004) 305, 1010-1013; Revollo et al., J. Biol. Chem., (2004) 279, 50754-50763; Schweigler et al., FEBS Lett., (2001) 492, 95-100), and the nucleus is indeed the major active site that synthesizes and consumes NAD at a high turnover (Rechsteiner et al., J. Cell. Physiol., (1974) 84, 409-422; Rechsteiner et al., Nature, (1976) 259, 695-696). Second, Sirt1 is known to function as a nuclear NAD-dependent deacetylase. In the nucleus, Sirt1 constantly requires NAD, while PARP consumes NAD only when activated by DNA damages. Lastly, it was previously demonstrated that Sirt1 promotes glucose-stimulated insulin secretion in β cells by generating pancreatic β cell-specific Sirt1-overexpressing (BESTO) mice (Moynihan et al., Cell Metab., (2005) 2, 105-117). Interestingly, the phenotypes observed in BESTO mice are completely opposite to those observed in Nampt$^{+/-}$ mice. Therefore, it is believed that Sirt1 might be a major downstream regulator that mediates the effects caused by alterations in systemic NAD biosynthesis in pancreatic β cells.

This model provides a general perspective for the physiological significance of Nampt-mediated NAD biosynthesis in glucose metabolism regulation. The model also provides important insights into how adipose tissue and pancreatic β cells communicate through this systemic NAD biosynthesis pathway under physiological and pathophysiological conditions.

EXAMPLE 20

Investigate the Role of NAMPT-Mediated Systemic NAD Biosynthesis

To investigate the role of Nampt-mediated systemic NAD biosynthesis in the pathogenesis of diet-induced obesity and type 2 diabetes, the effects of Nampt haplodeficiency and Nampt inhibition on high-fat diet (HFD)-induced diabetic symptoms will be examined by (1) feeding Nampt$^{+/-}$ mice with HFD and (2) administering FK866/APO966, a chemical inhibitor of Nampt, to HDF-fed Nampt$^{+/+}$ mice. Whether NMN administration alleviates the affects of Nampt haplodeficiency in HFD-fed Nampt$^{+/-}$ mice and/or improves the diabetic symptoms in HFD-fed Nampt$^{+/+}$ mice will also be examined.

According to the model described in Example 19, Nampt-mediated systemic NAD biosynthesis may play an important role in maintaining β cell function when demands on β cells increase in response to increasing peripheral insulin resistance. High-fat diet is one of the dietary conditions that can increase insulin resistance and eventually induce type 2 diabetes in animal models (McAuley et al., J. Lipid. Res., (2006) 47, 1668-1676). Therefore, to test the hypothesis, Nampt$^{+/-}$ mice, both males and females, will be fed with high-fat diet (HFD) and whether Nampt haplodeficiency accelerates diabetic symptoms in mice (section a. below) will be examined. To confirm that the anticipated effects of Nampt haplodeficiency on the disease progression is indeed due to the lack of the NAD biosynthetic activity of Nampt, a known chemical inhibitor named FK866 (Hasmann et al., Cancer Res., (2003) 63, 7436-7442; now renamed as APO866 by APOXIS, Switzerland) will be used for the Nampt enzymatic activity and whether FK866/APO866 can convey the same effects as Nampt haplodeficiency on the disease progression in HFD-fed Nampt$^{+/+}$ mice (section b. below) will be examined. Finally, because NMN administration corrects impaired glucose tolerance and reduced insulin secretion in Nampt$^{+/-}$ mice with regular diet (see Example 18), whether NMN administration also improve the symptoms observed in HFD-fed Nampt$^{+/-}$ and even in HFD-fed Nampt$^{+/+}$ control mice (section c. below) will be examined.

a. Examination of the Effects of Nampt Haplodeficiency on HFD-induced Obesity and Type 2 Diabetes.

A high-fat diet purchased from Harlan Teklad (TD 88137), which contains 42% calorie from fat, on wild-type C57BL/6 mice, starting at 8-12 weeks of age has previous been tested. After 3 months, these HFD-fed mice, especially males, gained more weight compared to age-matched controls fed with regular chow and showed hyperglycemia, hyperinsulinemia, and significantly impaired glucose tolerance, all of which are the characteristics of type 2 diabetes (empirically defining the diagnostic criteria for diabetes in mice, similar to those in humans: fasted blood glucose levels >120 mg/dl or blood glucose levels at 2 hr time point in IPGTT ≧200 mg/dl). Therefore, the same HFD and experimental protocol for Nampt$^{+/-}$ and Nampt$^{+/+}$ mice will be used.

20 males and 20 females for each genotype (Nampt$^{+/-}$ and Nampt$^{+/+}$) will be put on high-fat diet (TD 88137; Harlan Teklad) at 8-10 weeks of age and kept on this diet for 3 months. Then, the following multiple physiological parameters will be measured in all the mice. After the initial assessment, this HFD regimen will be continued for another 3 months and measure the same physiological parameters in the same individuals to evaluate the disease progression.

1. Blood Glucose and Insulin Levels

Fed glucose and insulin levels will be measured in the morning, while fasted glucose and insulin levels will be measured after 15 hours of overnight fasting. Glucose levels will be determined using the Accu-Chek II glucometer (Roche Diagnostics) with blood collected from the tail vein. For determining insulin levels, blood will be collected from the tail vein into chilled heparinized capillary tubes, and plasma will be separated by centrifugation and stored at −80° C. Insulin levels will be determined on 10 μl aliquots using mouse insulin ELISA kits (ALPCO Diagnostics, NH) with mouse insulin standards.

2. Leptin and Adiponectin Measurements

Blood leptin and adiponectin levels will be measured by using leptin (Mouse/Rat) and adiponectin (Mouse) ELISA kits (ALPCO Diagnostics, NH). As well as HFD-fed mice, these hormone levels in age-matched Nampt$^{+/-}$ and Nampt$^{+/+}$ mice fed with regular chow will also be measured.

3. Lipid Measurements

Cholesterol and triglycerides will be measured using reagents from Thermo Electron Corporation (Waltham, Mass.). Non-esterified free fatty acid levels will be measured using reagents from Wako Chemicals USA, Inc. (Richmond, Va.).

4. Intraperitoneal Glucose Tolerance Test (IPGTT) and Insulin Tolerance Test (ITT)

For IPGTTs, mice will be subjected to an overnight fast (14 hrs) followed by an intraperitoneal glucose injection (3 g dextrose/kg body weight) with a 0.5 ml insulin syringe attached to a 27 or 28 gauge needle. Blood glucose will be monitored with an Accu-Chek glucometer at 0, 15, 30, 60 and 120 min after injection. For ITTs, mice will be subjected to a 6-hr fast followed by intraperitoneal insulin injection (0.75 U kg$^{-1}$). Insulin (HumulinR, Eli Lilly, Indianapolis, Ind.) is diluted 1:500 with 0.9% NaCl. Blood glucose will be monitored with the glucometer at 0, 20, 40 and 60 min after injection. If a mouse shows a signs of seizure, the ITT will be terminated and dextrose injected to rescue it from hypoglycemic shock.

b. Examination of the Effects of FK866/APO866, the Nampt Chemical Inhibitor, on HFD-Induced Obesity and Type 2 Diabetes FK866 is a low molecular weight compound originally identified from an antitumor drug screening by a group in Fujisawa GmbH (now Astellas Pharma, Inc.) (Hasmann et al., Cancer Res., (2003) 63, 7436-7442). FK866 acts as a highly specific inhibitor of Nampt ($K_i$ of 0.4 nM) (Hasmann et al., Cancer Res., (2003) 63, 7436-7442), and the crystal structure of the Nampt-FK866 complex has recently been determined (Khan et al., Nat. Struct. Mol. Biol., (2006) 13, 582-588; Kim et al., J. Mol. Biol., (2006) 362, 66-77). The antitumor effect of FK866 has also been tested in an in vivo mouse mammary carcinoma model (Muruganandham et al., Clin. Cancer Res., (2005) 11, 3503-3515). Therefore, FK866 is a very useful reagent to examine the importance of the NAD biosynthetic activity of Nampt pharmacologically. Currently, Phase I-II trials of FK866 (now renamed as APO866) are being conducted for lymphoma, leukemia, and melanoma.

30 males and 30 females of wild-type B6 mice with the same high-fat diet described in section a. of this Example will be fed for 3 months. Then each sex group will be divided into two groups. To one group of 15 mice, eight total intraperitoneal injections of FK866/APO866 at a dose of 25 mg/kg body weight per injection will be administered with 12-hour interval between injections (the first dose will be given in the morning). This drug treatment protocol was employed in the in vivo mouse mammary carcinoma study and found to be effective to inhibit NAD biosynthesis without any obvious toxicity (Muruganandham et al., Clin. Cancer Res., (2005) 11, 3503-3515). To the other group of 15 mice, equal volumes of the solvent (regular saline and 60% propylene glycol) will be administered, following the same protocol. Right after the last dose, all the mice will be put in fasting and 12-14 hrs later subjected to the measurements of physiological parameters described in section a. of this Example.

c. Examination of the Effects of NMN Administration on the Symptoms Observed in HFD-Fed $Nampt^{+/-}$ and $Nampt^{+/+}$ Mice As described in Example 18, the administration of NMN at a dose of 500 mg/kg body weight corrected impaired glucose tolerance and reduced glucose-stimulated insulin secretion in $Nampt^{+/-}$ mice (see FIGS. 22A, 22B, and 22C). Therefore, it will be of great interest to examine whether NMN administration also alleviates the effects of Nampt haplodeficiency in HFD-fed $Nampt^{+/-}$ mice and even improves the symptoms in HFD-fed $Nampt^{+/+}$ mice. This particular dose of NMN has already been confirmed not cause any obvious toxicity in B6 mice. NMN administration causes an acute increase in blood glucose within 2 hrs, probably due to the rapid release of calcium and eicosanoid in the liver (Broetto-Biazon et al., Eur. J. Pharmacol., (2004) 484, 291-301). Therefore, physiological tests will be conducted ~14 hrs after NMN injection, as described in Example 18.

30 males and 30 females for each genotype ($Nampt^{+/-}$ and $Nampt^{+/+}$) will be fed with the same high-fat diet described in section a. of this Example for 3 months. Then each sex group of HFD-fed $Nampt^{+/-}$ and $Nampt^{+/+}$ mice will be divided into two groups. To one group of 15 mice, NMN at a dose of 500 mg/kg body weight will be administered intraperitoneally for five consecutive days. To the other groups of 15 mice, equal volumes of PBS will be injected intraperitoneally. Injection will be conducted at night, and right after the last injection, all the mice will be put in fasting and ~14 hrs later subjected to IPGTTs. Plasma samples will be collected at 0 and 30 min time points during IPGTTs to measure plasma insulin levels.

EXAMPLE 21

Further Investigation of the Role of NAMPT-Mediated Systemic NAD Biosynthesis

To further elaborate the role of Nampt-mediated NAD biosynthesis in pancreatic β cell function, functional characterization of pancreata and primary islets of $Nampt^{+/-}$ and $Nampt^{+/+}$ mice will be examined, including the measurements of insulin secretion, insulin contents, ATP production, $Ca^{2+}$ signaling, and apoptosis in response to various stimuli and dietary conditions. To elucidate a downstream mediator(s), the mammalian NAD-dependent deacetylase Sirt1 will be chosen as a candidate and expression of Sirt1 target genes between $Nampt^{+/-}$ and $Nampt^{+/+}$ islets will be compared by quantitative real-time RT-PCR.

The results from $Nampt^{+/-}$ mice and islets experiments suggest that Nampt-mediated NAD biosynthesis plays an important role in the regulation of insulin secretion in pancreatic β cells. Therefore, it may be important to elucidate how Nampt-mediated NAD biosynthesis affects insulin secretion in response to various nutritional stimuli and dietary conditions and what downstream regulators mediate these effects. Therefore, thorough functional characterization of pancreata and primary islets of $Nampt^{+/-}$ mice compared to those of $Nampt^{+/+}$ mice (section a. below) will be conducted. As reasoned in Example 19, one particularly interesting candidate of major downstream mediators is the mammalian NAD-dependent deacetylase Sirt1. Therefore, this possibility will be addressed by comparing the expression of Sirt1 target genes between primary islets from $Nampt^{+/-}$ and $Nampt^{+/+}$ mice (section b. below).

a. The Functional Characterization of Pancreata and Primary Islets of $Nampt^{+/-}$ Mice 1. Measurement of Insulin Secretion from in situ Perfused Pancreata $Nampt^{+/-}$ and $Nampt^{+/+}$ mice will be fed with regular chow or HFD. Pancreata will be perfused via the aorta at the celiac artery in a humidified, temperature-controlled chamber, as described previously (Johnson et al., J. Clin. Invest., (2003) 111, 1147-1160). The perfusate consists of oxygenated Krebs-Ringer bicarbonate buffer (KRB), containing 119 mM NaCl, 4.7 mM KCl, 25 mM $NaHCO_3$, 2.5 mM $CaCl_2$, 1.2 mM $MgSO_4$, 1.2 mM $KH_2PO_4$, and 0.25% radioimmunoassay-grade BSA with either 2 or 25 mM glucoseor 25 mM KCl. The perfusion will be maintained at a constant rate of 1 ml/min using Minipuls 3 peristaltic pumps. Prior to sample collection, the pancreas will be perfused with 2 mM glucose/KRB for 45 minutes. The effluent will then be collected at 1, 2, or 5 minute intervals. The insulin concentration of each fraction will be determined by radioimmunoassay. The area under the curve (AUC) at each time interval will be calculated to determine the amount of insulin secreted during glucose and KCl stimulation, and the Wilcoxon matched pairs test will be employed for statistical analyses.

2. Measurement of Total Pancreatic Insulin Contents

For $Nampt^{+/-}$ and $Nampt^{+/+}$ mice fed with regular chow or HFD, total pancreatic insulin content will be measured after acid-ethanol extraction of the whole pancreas, as described previously (Ma et al., J. Clin. Invest., (2004) 114, 339-348). Extraction will be repeated twice, and the supernatants will be pooled and stored at −20° C. The insulin concentration will be measured by radioiummunoassay.

3. Measurement of Insulin Secretion, Insulin Content, and ATP Production in Primary Islets in Response to Glucose, Free Fatty Acid, and KCl Primary islets will be isolated by collagenase digestion from $Nampt^{+/-}$ and $Nampt^{+/+}$ mice fed with regular chow (Moynihan et al., Cell Metab., (2005) 2, 105-117). Briefly, pancreata will be inflated with isolation buffer (10× HBSS, 10 mM HEPES, 1 mM $MgCl_2$, 5 mM glucose, pH 7.4) containing 0.375 mg/ml collagenase (Sigma) via the pancreatic duct after clamping off its entry site to the duodenum. The inflated pancreas will then be removed, incubated at 37° C. for 12-15 minutes, and shaken vigorously. Islets will be separated from acinar tissue after a series of washes and passages through a 70 μm nylon BD Falcon Cell Strainer (BD Biosciences).

Handpicked islets will be cultured overnight in RPMI media containing either 5 or 11 mM glucose, 2 mM L-glutamine, 1 μM nicotinamide, penicillin/streptomycin, and 10% fetal bovine serum. To examine the effects of free fatty acid (FFA), isolated islets will be cultured for 48 hours in RPMI media with or without 0.5 mM palmitic acid or oleic acid (Sigma, MO). Media containing palmitic acid or oleic acid will be prepared as a stock solution in 5% fatty acid-free BSA (Sigma, MO) and diluted on the day of the experiment. The islets will then be preincubated in KRB buffer containing 2 mM glucose for 1 hour at 37° C. Islets of similar size will be handpicked into groups of 10 islets in triplicate and incubated with 1 ml KRB buffer containing either 2 mM glucose, 20 mM glucose, (free fatty acid) or 20 mM KCl plus 2 mM glucose for 1 hour at 37° C. The supernatant will be stored at −20° C. prior to insulin measurements. After the insulin secretion experiments, islets will be washed twice with PBS and extracted with acid-ethanol overnight at 4° C. in order to measure insulin content. Insulin levels of all samples will be measured by radioimmunoassay.

To measure ATP levels in islets, islets will be washed twice with PBS after the insulin secretion experiments and then extracted with extraction buffer (0.1 M NaOH, 0.5 mM EDTA). After neutralizing the samples with 0.1 M HCl, ATP levels will be measured using the ATP Bioluminescent Assay Kit (Sigma) according to the manufacturer's instructions. Protein concentration of the islets will be determined, and ATP will be normalized to the protein content.

4. $Ca^{2+}$ Imaging

Primary islets isolated from $Nampt^{+/-}$ and $Nampt^{+/+}$ mice will be cultured on glass coverslips overnight prior to imaging for $Ca^{2+}$ levels, as described previously (Johnson et al., J. Clin. Invest., (2003) 111, 1147-1160). Briefly, islets will be loaded with 2 µM Fura-2 acetoxymethylester (Invitrogen, CA) for 60 min and then be perfused at a flow rate of 1 ml/min with KRB buffer without BSA at 37° C. on the stage of a Nikon inverted microscope. Changes in intracellular $Ca^{2+}$ within individual islets will be determined as the ratio of emitted fluorescence intensity acquired above 510 nm after excitation at either 340 or 380 nm.

5. Measurement of Apoptosis in Primary Islets

A PCR-based method will be employed to detect DNA ladders according to the manufacturer's protocol (ApoAlert LM-PCR Ladder Assay Kit, Clontech). Briefly, groups of 10 islets from $Nampt^{+/-}$ and $Nampt^{+/+}$ mice will be cultured separately in RPMI containing various concentrations of glucose (5, 10, and 25 mM) 0.5 mM palmitic acid or oleic acid, or 10 µM thapsigarin, a known inducer of islet apoptosis as a positive control. After 24-72 hrs, genomic DNA will be isolated (DNeasy kit (QIAGEN)), and DNA concentration will be determined by UV spectrophotometry. 200 ng of genomic DNA will be ligated to adaptors, and short cycles of PCR will be conducted to selectively amplify adaptor-ligated DNA fragments. The resulting PCR products will be separated on 2% agarose/ethidium bromide gel in 0.5× TBE buffer. DNA ladders will be quantified with BioRad DNA photodocumentation system. DNA ladder density will be normalized as a percentage of untreated, wild-type controls.

6. Treatment of $NAMPT^{+/-}$ Islets with NMN

Because the phenotypes of $Nampt^{+/-}$ mice were corrected with NMN administration (see Example 18), whether or not the phenotypes of $Nampt^{+/-}$ islets can also be corrected with NMN will also be examined. To address this possibility, primary islets isolated from $Nampt^{+/-}$ and $Nampt^{+/+}$ mice will be cultured overnight in nicotinamide-minus RPMI media containing 50 µM NMN. NMN-treated $Nampt^{+/-}$ and $Nampt^{+/+}$ islets will be subjected to the assays described above.

b. Comparison of Sirt1 Target Gene Expression between Islets from $Nampt^{+/-}$ and $Nampt^{+/+}$ Mice As described above, the mammalian NAD-dependent deacetylase Sirt1 might be one of the major downstream factors that regulate insulin secretion in response to changes in systemic NAD biosynthesis in pancreatic 13 cells. If so, Sirt1 activity might decrease in $Nampt^{+/-}$ β cells compared to that in wild-type 13 cells, which might result in the decrease in glucose-stimulated insulin secretion based on previous studies (Bordone et al., PLoS Biol., (2006) 4, e31; Moynihan et al., Cell Metab., (2005) 2, 105-117). To measure in vivo Sirt1 activity, the expression profiles of Sirt1 target genes will be examined because Sirt1 requires NAD in the nucleus so that it is not technically feasible to directly measure in vivo Sirt1 activity. For this reason, extensive microarray analyses will be conducted to find out genes whose expression is sensitive to Sirt1 activity in different cell types (Moynihan et al., Cell Metab., (2005) 2, 105-117; Revollo et al., J. Biol. Chem., (2004) 279, 50754-50763).

Recently, another microarray analysis with Illumina's microbeads-based microarrays (MouseRef-8 Expression BeadChip) was conducted to compare expression profiles between primary islets from BESTO and control mice (Moynihan et al., Cell Metab., (2005) 2, 105-117). This platform enabled the comparison of gene expression profiles with very small amounts of islet RNA. The gene expression profiles revealed that Sirt1 regulates the expression of genes involved in a variety of important functions in the β cell, including insulin granule exocytosis, cation transport, calcium binding, and carbohydrate and cholesterol metabolism (unpublished results), which provide a useful panel of genes that allows us to evaluate Sirt1 activity in pancreatic β cells. By using this panel of genes, whether Sirt1 activity decreases in $Nampt^{+/-}$ islets will be evaluated.

Total RNA samples will be purified from primary islets isolated from $Nampt^{+/-}$ and $Nampt^{+/+}$ mice using a RNeasy kit (Qiagen) according to the manufacturer's protocol. For each sample, cDNA will be synthesized from approximately 1 µg of total RNA using an Omniscript kit (Qiagen) with random hexamer primers and an RNase inhibitor (Promega) according to the manufacturer's instructions. The real-time quantitative RT-PCR will be carried out using a SYBR Green PCR Master Mix kit (Applied Biosystems) and gene-specific primers in an ABI PRISM 7700 Sequence Detection System (Applied Biosystems) as previously described (Moynihan et al., Cell Metab., (2005) 2, 105-117; Revollo et al., J. Biol. Chem., (2004) 279, 50754-50763). Briefly, cDNA template comparable to 200 ng of total RNA will be added to each well in a 96-well reaction plate, and the transcripts of each gene will be amplified in triplicate. Average $C_T$ values will be calculated, and the $\Delta C_T$ relative to GAPDH control will be computed for each gene. Subsequently, $\Delta\Delta C_T$ will be computed for each gene by subtracting the average $\Delta C_T$ for $Nampt^{+/-}$ islets from the average $\Delta C_T$ for $Nampt^{+/+}$ islets. The final fold differences will be computed as $2^{-\Delta\Delta C_T}$ for each gene. The measurements will be repeated with three independent RNA samples from three mice for each gene.

EXAMPLE 22

Further Investigation of the Role of NAMPT-Mediated Systemic NAD Biosynthesis

To examine whether nutritional, hormonal, and pharmacological stimuli modulate Nampt production/secretion in adipose tissue, white and brown adipose tissue from wild-type mice will be isolated and the production of intracellular and extracelluar versions of Nampt in response to nutrients (glucose and free fatty acids), hormones (insulin, norepinephrine, thyroid hormones, and cortisol), and peroxisome proliferator-activated receptor (PAPR) α and γ agonists will be examined. Whether Nampt haplodeficiency affects the morphology and the function of adipose tissue in $Nampt^{+/-}$ mice will also be examined by assessing size, cell number, differentiation markers, and adipokine secretion from isolated white and brown adipose tissue.

As described in previous Examples, fully differentiated HIB-1B brown adipocytes secrete a significant amount of highly active extracellular Nampt through a non-classical secretory pathway. Fully differentiated 3T3-L1 white adipocytes also secrete a marginal level of eNampt. To date, no other cell types that naturally secrete extracellular Nampt have been observed, although Chinese hamster ovary cells are capable of secreting extracellular Nampt when transfected with the Nampt gene. Therefore, adipocytes may be a major source of eNampt in vivo. Consistent with this notion, it has been reported that plasma levels of eNampt/PBEF/visfatin correlate with measures of obesity (Berndt et al., Diabetes, (2005) 54, 2911-2916) and type 2 diabetes (Chen et al., J. Clin. Endocrin. Metab., (2006) 91, 295-299), but not with visceral fat mass or waist-to-hip ratio (Berndt et al., Diabetes, (2005) 54, 2911-2916). Based on these findings, it is speculated, as described above, that white adipose tissue, as well as brown adipose tissue, might secrete more extracellular Nampt and thereby increase systemic NAD biosynthesis in certain pathophysiological conditions that cause significant changes in adipose tissue mass, structure, or function, such as obesity and type 2 diabetes. In this regard, there is a paper reporting that plasma concentrations of eNampt/PBEF/visfatin are increased by hyperglycemia and that this effect is suppressed by insulin co-infusion in humans (Haider et al., Diabetologia, (2006) 49, 1909-1914). However, the reliability of the samples used in this particular study has been disputed by another group (Pfutzner et al., Diabetologia (2006) 49, 1909-1914). Therefore, it may be important to carefully and thoroughly examine how Nampt production/secretion is regulated in adipose tissue in response to various nutritional, hormonal, and pharmacological stimuli. To address this problem, the production/secretion of Nampt in primary white and brown adipose tissue isolated from wild-type mice in response to a variety of stimuli (described above) will be examined. Additionally, the physiological importance of Nampt in the morphology and the function of adipose tissue will be further elucidated. Therefore, morphological and functional characterization of primary white and brown adipose tissue isolated from $Nampt^{+/-}$ mice will be conducted.

a. Examination of Nampt Production/Secretion in Primary White and Brown Adipose Tissues (WAT and BAT) in Response to Nutritional, Hormonal, and Pharmacological Stimuli Epididymal WAT and interscapular BAT will be isolated from 8-10 weeks-old C57BL/6 mice immediately after $CO_2$ asphyxiation. Each tissue will be minced into pieces and placed in HEPES-buffered Krebs-Ringer medium (KRH, pH 7.4) containing 0.1% BSA (Fraction V, fatty acid-free, Sigma) and 2 mM glucose. Erythrocytes and other blood cells will be removed by centrifuging tissues at 1,000 g for 10 min at room temperature. After pre-incubating in the same KRH buffer for 1 h, WAT and BAT tissues will be incubated at 37° C. in the presence of each of the following stimulants. The levels of extracellular Nampt in culture supernatants will be determined by Western blotting with a anti-Nampt antibody or by using mouse visfatin ELISA kit (CY-8065, MBL International, MA). The total secretion of extracellular Nampt per hour will be normalized to a total amount of tissue protein. The levels of intracellular Nampt in WAT and BAT will also be determined after treatments by Western blotting.

1. Nutritional Stimulants

The effects of glucose and free fatty acids (palmitic acid and oleic acid) will be examined. For glucose, 5, 10, and 20 mM glucose will be added to KRH buffer. For free fatty acids, a stock solution of palmitic acid or oleic acid pre-bound to BSA will be added to KRH buffer at 0.5 or 2 mM as a final concentration. Tissues will be incubated in each condition for 4 hrs.

2. Hormonal Stimulants

Insulin, norepinephrine, thyroid hormones, and cortisol, all play important roles in the regulation of adipose tissue function. For example, leptin secretion is stimulated by insulin and cortisol, while it is inhibited by epinephrine, norepinephrine, and T3 (Fried et al., J. Nutr., (2000) 130, 3127S-3131S; Medina-Gomez et al., Biochim. Biophys. Acta, (2004) 1682, 38-47). Insulin (XX-YY), norepinephrine (ZZ-AA), T3 (FF-GG) and T4 (DD-JJ), and cortisol (EE-FF) will be added to KRH buffer, and tissues will be incubated in each condition for PP-QQ hrs.

3. Pharmacological Stimulants

The effects of peroxisome proliferator-activated receptor (PAPR) α and γ agonists on Nampt production/secretion may also be significant. PPARα is reported to play an important role in the regulation of cholesterol and triacylglycerol homeostasis in WAT (Islam et al., Biochim. Biophys. Acta, (2005) 1734, 259-268). The activation of PPARα by its agonist, Wy-14,643, increases adiponectin receptor expression in both WAT and BAT (Tsuchida et al., Diabetes, (2005) 54, 3358-3370). PPARγ stimulates fatty acid storage in adipose tissue by up-regulating the expression of numerous genes involved in lipid metabolism and uptake (Fatehi-Hassanabad et al., Nutr. Metab., (2005) 2, 1). PPARγ also negatively regulates the expression of several adipokine genes, including TNFα and leptin (Fatehi-Hassanabad et al., Nutr. Metab., (2005) 2, 1). Therefore, the activation of PPARγ by its agonists, such as thiazolidinediones (TZDs), stimulates lipid storage and reduces the secretion of adipokines that cause insulin resistance. To examine the effects of these PPARα and γ agonists, Wy-14,643 (PPARα agonist, BIOMOL) and troglitazone (PPARγ agonist, BIOMOL) will be added to KRH buffer at 30 µM and 100 µM, respectively. Tissues will be cultured in the presence of each agonist for 1-12 hrs (optimal incubation time will be determined by examining multiple time points).

b. Morphological and Functional Characterization of Primary White and Brown Adipose Tissues Isolated from $Nampt^{+/-}$ Mice Size, cell number, differentiation markers, and adipokine secretion from isolated white and brown adipose tissues will be compared between $Nampt^{+/-}$ and $Nampt^{+/+}$ mice.

1. Cell Size and Number

Epididymal WAT will be osmium fixed, and osmium fixed cells will be mounted on microscope slides in 50% glycerol. Adipocyte diameter will be estimated as described by Chen and Farese (Chen et al., J. Lipid Res., (2002) 43, 986-989. Briefly, sections will be viewed at 10× magnification with a Nikon Eclipse TE2000-U microscope in epi-flourescence using an EXFO-Xcite-TM120 PC Illumination System and a Photometrics Cool SNAPcf monochrome camera (Roper Scientific, Tuscon, Ariz.). Morphometery will be conducted with MetaMorph v6.2r6 (Universal Imaging Corp) at the resolution of 0.45 µm/pixel. Measurements will be loaded into Microsoft Excel (Microsoft, Redmond, Wash.) to calculate mean cell size. Osmium fixed cells will also be counted with a Beckman-Coulter counter.

2. Differentiation Markers

Total RNA will be purified from epididymal WAT and interscapular BAT from Nampt$^{+/-}$ and Nampt$^{+/+}$ mice, as described in section D2b. The real-time quantitative RT-PCR will be carried out using a SYBR Green PCR Master Mix kit (Applied Biosystems) and gene-specific primers in an ABI PRISM 7700 Sequence Detection System (Applied Biosystems) as described previously (Moynihan et al., Cell Metab., (2005) 2, 105-117; Revollo et al., J. Biol. Chem., (2004) 279, 50754-50763).

3. Adipokine Secretion

The secretion of leptin, TNF-α, and adiponectin will be measured in epididymal WAT and interscapular BAT from Nampt$^{+/-}$ and Nampt$^{+/+}$ mice.

What is claimed is:

1. A process for regulating the concentration of blood glucose in a mammal, the process comprising administering to the mammal a blood glucose concentration-regulating amount of nicotinamide mononucleotide (NMN) or a salt or prodrug thereof.

2. The process as set forth in claim 1 wherein the blood glucose concentration-regulating amount comprises at least about 10 mg of nicotinamide mononucleotide (NMN) per kg body weight of the mammal.

3. The process as set forth in claim 1 wherein the blood glucose concentration-regulating amount is from about 10 mg of nicotinamide mononucleotide (NMN) per kg body weight of the mammal to about 1,000 mg of nicotinamide mononucleotide (NMN) per kg body weight of the mammal.

4. The process as set forth in claim 1 wherein the blood glucose concentration-regulating amount is from about 50 mg of nicotinamide mononucleotide (NMN) per kg body weight of the mammal to about 500 mg of nicotinamide mononucleotide (NMN) per kg body weight of the mammal.

5. The process as set forth in claim 2 wherein the blood glucose concentration regulation comprises increasing the blood glucose concentration, decreasing the blood glucose concentration, maintaining the blood glucose concentration, and combinations thereof.

* * * * *

```
                        SEQUENCE LISTING

<160> NUMBER OF SEQ ID NOS: 19

<210> SEQ ID NO 1
<211> LENGTH: 491
<212> TYPE: PRT
<213> ORGANISM: Mus musculus

<400> SEQUENCE: 1

Met Asn Ala Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Val Arg Lys Val Lys Tyr Glu Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Glu Val Tyr Arg Glu His Phe Gln Asp Asp Val Phe
                85                  90                  95

Asn Glu Arg Gly Trp Asn Tyr Ile Leu Glu Lys Tyr Asp Gly His Leu
            100                 105                 110

Pro Ile Glu Val Lys Ala Val Pro Glu Gly Ser Val Ile Pro Arg Gly
        115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Ile
    210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
            260                 265                 270

Pro Val Ser Val Val Ser Asp Ser Tyr Asp Ile Tyr Asn Ala Cys Glu
        275                 280                 285

Lys Ile Trp Gly Glu Asp Leu Arg His Leu Ile Val Ser Arg Ser Thr
    290                 295                 300
```

```
Glu Ala Pro Leu Ile Ile Arg Pro Asp Ser Gly Asn Pro Leu Asp Thr
305                 310                 315                 320

Val Leu Lys Val Leu Asp Ile Leu Gly Lys Lys Phe Pro Val Thr Glu
            325                 330                 335

Asn Ser Lys Gly Tyr Lys Leu Leu Pro Pro Tyr Leu Arg Val Ile Gln
        340                 345                 350

Gly Asp Gly Val Asp Ile Asn Thr Leu Gln Glu Ile Val Glu Gly Met
    355                 360                 365

Lys Gln Lys Lys Trp Ser Ile Glu Asn Val Ser Phe Gly Ser Gly Gly
370                 375                 380

Ala Leu Leu Gln Lys Leu Thr Arg Asp Leu Leu Asn Cys Ser Phe Lys
385                 390                 395                 400

Cys Ser Tyr Val Val Thr Asn Gly Leu Gly Val Asn Val Phe Lys Asp
            405                 410                 415

Pro Val Ala Asp Pro Asn Lys Arg Ser Lys Lys Gly Arg Leu Ser Leu
        420                 425                 430

His Arg Thr Pro Ala Gly Asn Phe Val Thr Leu Glu Glu Gly Lys Gly
    435                 440                 445

Asp Leu Glu Glu Tyr Gly His Asp Leu Leu His Thr Val Phe Lys Asn
    450                 455                 460

Gly Lys Val Thr Lys Ser Tyr Ser Phe Asp Glu Val Arg Lys Asn Ala
465                 470                 475                 480

Gln Leu Asn Ile Glu Gln Asp Val Ala Pro His
            485                 490

<210> SEQ ID NO 2
<211> LENGTH: 29
<212> TYPE: DNA
<213> ORGANISM: Artificial sequence
<220> FEATURE:
<223> OTHER INFORMATION: Primer for Polymerase Chain Reaction (PCR)

<400> SEQUENCE: 2
ttagaattca gcccattttt ctccttgct                                        29

<210> SEQ ID NO 3
<211> LENGTH: 30
<212> TYPE: DNA
<213> ORGANISM: Artificial sequence
<220> FEATURE:
<223> OTHER INFORMATION: Primer for Polymerase Chain Reaction (PCR)

<400> SEQUENCE: 3
ttagaattca cataacaacc cggccacatg                                       30

<210> SEQ ID NO 4
<211> LENGTH: 27
<212> TYPE: DNA
<213> ORGANISM: Artificial Sequence
<220> FEATURE:
<223> OTHER INFORMATION: Primer for Polymerase Chain Reaction (PCR)

<400> SEQUENCE: 4
ttagaattct ggaggactag ggccgtt                                          27

<210> SEQ ID NO 5
<211> LENGTH: 28
<212> TYPE: DNA
<213> ORGANISM: Artificial Sequence
<220> FEATURE:
<223> OTHER INFORMATION: Primer for Polymerase Chain Reaction (PCR)
```

<400> SEQUENCE: 5
ttagaattct gccctgtgtc acagagtg                                                                28

<210> SEQ ID NO 6
<211> LENGTH: 69
<212> TYPE: DNA
<213> ORGANISM: Artificial Sequence
<220> FEATURE:
<223> OTHER INFORMATION: Nampt-FLAG (tm) reverse primer for Polymerase
      Chain Reaction (PCR)

<400> SEQUENCE: 6
taatgaattc tacttatcgt cgtcatcctt gtaatctcct ccatgaggtg ccacgtcctg             60
ctcgatgtt                                                                     69

<210> SEQ ID NO 7
<211> LENGTH: 501
<212> TYPE: PRT
<213> ORGANISM: Artificial Sequence
<220> FEATURE:
<223> OTHER INFORMATION: Nampt-FLAG (tm) protein

<400> SEQUENCE: 7

```
Met Asn Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Val Arg Lys Val Lys Tyr Glu Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Glu Val Tyr Arg Glu His Phe Gln Asp Asp Val Phe
                85                  90                  95

Asn Glu Arg Gly Trp Asn Tyr Ile Leu Glu Lys Tyr Asp Gly His Leu
            100                 105                 110

Pro Ile Glu Val Lys Ala Val Pro Glu Gly Ser Val Ile Pro Arg Gly
        115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Ile
    210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
```

```
                    260                 265                 270
Pro Val Ser Val Ser Asp Ser Tyr Asp Ile Tyr Asn Ala Cys Glu
        275                 280                 285
Lys Ile Trp Gly Glu Asp Leu Arg His Leu Ile Val Ser Arg Ser Thr
290                 295                 300
Glu Ala Pro Leu Ile Ile Arg Pro Asp Ser Gly Asn Pro Leu Asp Thr
305                 310                 315                 320
Val Leu Lys Val Leu Asp Ile Leu Gly Lys Lys Phe Pro Val Thr Glu
                325                 330                 335
Asn Ser Lys Gly Tyr Lys Leu Leu Pro Pro Tyr Leu Arg Val Ile Gln
            340                 345                 350
Gly Asp Gly Val Asp Ile Asn Thr Leu Gln Glu Ile Val Glu Gly Met
        355                 360                 365
Lys Gln Lys Lys Trp Ser Ile Glu Asn Val Ser Phe Gly Ser Gly Gly
            370                 375                 380
Ala Leu Leu Gln Lys Leu Thr Arg Asp Leu Leu Asn Cys Ser Phe Lys
385                 390                 395                 400
Cys Ser Tyr Val Val Thr Asn Gly Leu Gly Val Asn Val Phe Lys Asp
                405                 410                 415
Pro Val Ala Asp Pro Asn Lys Arg Ser Lys Lys Gly Arg Leu Ser Leu
            420                 425                 430
His Arg Thr Pro Ala Gly Asn Phe Val Thr Leu Glu Glu Gly Lys Gly
        435                 440                 445
Asp Leu Glu Glu Tyr Gly His Asp Leu Leu His Thr Val Phe Lys Asn
450                 455                 460
Gly Lys Val Thr Lys Ser Tyr Ser Phe Asp Glu Val Arg Lys Asn Ala
465                 470                 475                 480
Gln Leu Asn Ile Glu Gln Asp Val Ala Pro His Gly Gly Asp Tyr Lys
                485                 490                 495
Asp Asp Asp Asp Lys
            500

<210> SEQ ID NO 8
<211> LENGTH: 32
<212> TYPE: DNA
<213> ORGANISM: Artificial Sequence
<220> FEATURE:
<223> OTHER INFORMATION: Primer for Polymerase Chain Reaction (PCR)

<400> SEQUENCE: 8
cctgttactg agaactcaaa aggctacaag tt                              32

<210> SEQ ID NO 9
<211> LENGTH: 32
<212> TYPE: DNA
<213> ORGANISM: Artificial Sequence
<220> FEATURE:
<223> OTHER INFORMATION: Primer for Polymerase Chain Reaction (PCR)

<400> SEQUENCE: 9
ctgagaaaga acatctgaaa aacatacttt cg                              32

<210> SEQ ID NO 10
<211> LENGTH: 29
<212> TYPE: DNA
<213> ORGANISM: Artificial Sequence
<220> FEATURE:
<223> OTHER INFORMATION: Primer for Polymerase Chain Reaction (PCR)
```

```
<400> SEQUENCE: 10
aaatatgctt tgactgcccc tttcagtat                              29

<210> SEQ ID NO 11
<211> LENGTH: 259
<212> TYPE: DNA
<213> ORGANISM: Mus musculus

<400> SEQUENCE: 11
cctgttactg agaactcaaa aggctacaag ttgctgccac cttatcttag agtcattcaa    60
ggagatggcg tggatatcaa tactttacaa gaggtgtgtg ttttacatga atgtcccaat   120
catgaaatcc ccattcttga aacagctttt tattcataaa cagcctgtta aattttaagt   180
gcaattgtga gtctaattta aaatatttat aatggcaaat ccggaaccga agtatgttt    240 ttcagatgtt ctttctcag                                               259

<210> SEQ ID NO 12
<211> LENGTH: 28
<212> TYPE: DNA
<213> ORGANISM: Artificial Sequence
<220> FEATURE:
<223> OTHER INFORMATION: Primer for Polymerase Chain Reaction (PCR)

<400> SEQUENCE: 12
taccgcacag atgcgtaagg agaaaata                              28

<210> SEQ ID NO 13
<211> LENGTH: 215
<212> TYPE: DNA
<213> ORGANISM: Mus musculus

<400> SEQUENCE: 13
taccgcacag atgcgtaagg agaaaatacc gcatcaggcg ccattcgcca ttcaggctgc    60
gcaactgttg ggaagggcga tcggtgcggg cctcttcgct attacgccag ctggcgaaag   120
ggggatgtgc tgcaaggcga ttaagttggg taacgccagg gttttagaa ataatagtac    180 cttagaatac tgaaaggggc agtcaaagca tattt                             215

<210> SEQ ID NO 14
<211> LENGTH: 32
<212> TYPE: DNA
<213> ORGANISM: Artificial Sequence
<220> FEATURE:
<223> OTHER INFORMATION: Primer for Polymerase Chain Reaction (PCR)

<400> SEQUENCE: 14
catttaatgt tgatgaaagc tggctacagg aa                         32

<210> SEQ ID NO 15
<211> LENGTH: 32
<212> TYPE: DNA
<213> ORGANISM: Artificial Sequence
<220> FEATURE:
<223> OTHER INFORMATION: Primer for Polymerase Chain Reaction (PCR)

<400> SEQUENCE: 15
gaaatcgctg atttgtgtag tcggtttatg ca                         32

<210> SEQ ID NO 16
<211> LENGTH: 8
<212> TYPE: PRT
<213> ORGANISM: Artificial Sequence
```

```
<220> FEATURE:
<223> OTHER INFORMATION: Invented

<400> SEQUENCE: 16

Asp Tyr Lys Asp Asp Asp Asp Lys
1               5

<210> SEQ ID NO 17
<211> LENGTH: 8
<212> TYPE: PRT
<213> ORGANISM: Artificial Sequence
<220> FEATURE:
<223> OTHER INFORMATION: Invented

<400> SEQUENCE: 17

Asp Leu Tyr Asp Asp Asp Asp Lys
1               5

<210> SEQ ID NO 18
<211> LENGTH: 1572
<212> TYPE: DNA
<213> ORGANISM: Mus musculus

<400> SEQUENCE: 18
agcccatttt tctccttgct cgcagccgcg ccgggcagct cgtggcgcgg cgtctccgct      60
ccggcccgag atgaatgctg cggcagaagc cgagttcaac atcctgctgg ccaccgactc     120
gtacaaggtt actcactata acaataccc acccaacaca agcaaagttt attcctactt     180
tgaatgccgt gaaagaaga cagaaaactc caaagtaagg aaggtgaaat acgaggaaac     240
agtattttat ggggttgcagt acattcttaa taagtactta aaaggtaaag tagtgaccaa     300
agagaaaatc caggaggcca aagaagtgta cagagaacat ttccaagatg atgtctttaa     360
cgaaagagga tggaactaca tccttgagaa atacgatggt catctcccga ttgaagtaaa     420
ggctgttccc gagggctctg tcatccccag agggaacgtg ctgttcacag tggaaaacac     480
agacccagag tgctactggc ttaccaattg gattgagact attcttgttc agtcctggta     540
tccaattaca gtggccacaa attccagaga acagaagaaa atactggcca atatttgtt     600 agaaacctct ggtaacttag atggtctgga atacaagtta catgactttg gttacagagg     660
agtctcttcg caagagactg ctggcatagg ggcatctgct catttggtta actttaaagg     720
aacagatact gtggcgggaa ttgctctaat taaaaaatac tatgggacaa agatcctgt     780 tccaggctat tctgttccag cagcagagca cagtaccata acggcttggg ggaaagacca     840
tgagaaagat gcttttgaac acatagtaac acagttctca tcagtgcctg tgtctgtggt     900
cagcgatagc tatgacattt ataatgcgtg tgagaaaata tggggtgaag acctgagaca     960
tctgatagta tcgagaagta cagaggcacc actaatcatc agacctgact ctggaaatcc    1020
tcttgacact gtattgaagg tcttagatat tttaggcaag aagtttcctg ttactgagaa    1080
ctcaaaaggc tacaagttgc tgccaccta tcttagagtc attcaaggag atggcgtgga    1140
tatcaatact ttacaagaga ttgtagaggg aatgaaacaa agaagtgga gtatcgagaa    1200 tgtctccttc ggttctggtg gcgctttgct acagaagtta acccgagacc tcttgaattg    1260
ctccttcaag tgcagctatg ttgtaaccaa tggccttggg gttaatgtgt ttaaggaccc    1320
agttgctgat cccaacaaaa ggtcaaaaaa gggccggtta tctttacata ggacaccagc    1380
ggggaacttt gttacacttg aagaaggaaa aggagacctt gaggaatatg gccatgatct    1440
tctccatacg gttttcaaga atgggaaggt gacaaaaagc tactcatttg atgaagtcag    1500
```

| | |
|---|---|
| aaaaaatgca cagctgaaca tcgagcagga cgtggcacct cattaggctt catgtggccg | 1560 |
| ggttgttatg tg | 1572 |

<210> SEQ ID NO 19
<211> LENGTH: 1506
<212> TYPE: DNA
<213> ORGANISM: Mus musculus

<400> SEQUENCE: 19

| | |
|---|---|
| atgaatgctg cggcagaagc cgagttcaac atcctgctgg ccaccgactc gtacaaggtt | 60 |
| actcactata acaataccc acccaacaca agcaaagttt attcctactt tgaatgccgt | 120 |
| gaaaagaaga cagaaaactc caagtaagg aaggtgaaat acgaggaaac agtattttat | 180 |
| gggttgcagt acattcttaa taagtactta aaaggtaaag tagtgaccaa agagaaaatc | 240 |
| caggaggcca agaagtgta cagagaacat tccaagatg atgtctttaa cgaaagagga | 300 |
| tggaactaca tccttgagaa atacgatggt catctcccga ttgaagtaaa ggctgttccc | 360 |
| gagggctctg tcatccccag agggaacgtg ctgttcacag tggaaaacac agacccagag | 420 |
| tgctactggc ttaccaattg gattgagact attcttgttc agtcctggta tccaattaca | 480 |
| gtggccacaa attccagaga acagaagaaa atactggcca atatttgtt agaaacctct | 540 |
| ggtaacttag atggtctgga atacaagtta catgactttg ttacagagg agtctcttcg | 600 |
| caagagactg ctggcatagg ggcatctgct catttggtta actttaaagg aacagatact | 660 |
| gtggcgggaa ttgctctaat taaaaaatac tatgggacaa agatcctgt tccaggctat | 720 |
| tctgttccag cagcagagca cagtaccata acggcttggg ggaaagacca tgagaaagat | 780 |
| gcttttgaac acatagtaac acagttctca tcagtgcctg tgtctgtggt cagcgatagc | 840 |
| tatgacattt ataatgcgtg tgagaaaata tggggtgaag acctgagaca tctgatagta | 900 |
| tcgagaagta cagaggcacc actaatcatc agacctgact ctggaaatcc tcttgacact | 960 |
| gtattgaagg tcttagatat tttaggcaag aagtttcctg ttactgagaa ctcaaaaggc | 1020 |
| tacaagttgc tgccaccta tcttagagtc attcaaggag atggcgtgga tatcaatact | 1080 |
| ttacaagaga ttgtagaggg aatgaaacaa agaagtgga gtatcgagaa tgtctccttc | 1140 |
| ggttctggtg gcgctttgct acagaagtta acccgagacc tcttgaattg ctccttcaag | 1200 |
| tgcagctatg ttgtaaccaa tggccttggg gttaatgtgt ttaaggaccc agttgctgat | 1260 |
| cccaacaaaa ggtcaaaaaa gggccggtta tctttacata ggacaccagc ggggaacttt | 1320 |
| gttacacttg aagaaggaaa aggagaccct gaggaatatg ccatgatct tctccatacg | 1380 |
| gttttcaaga atgggaaggt gacaaaaagc tactcatttg atgaagtcag aaaaaatgca | 1440 |
| cagctgaaca tcgagcagga cgtggcacct catggaggag attacaagga tgacgacgat | 1500 |
| aagtag | 1506 |